(12) United States Patent
Butcher et al.

(10) Patent No.: US 9,096,598 B2
(45) Date of Patent: Aug. 4, 2015

(54) AZAINDOLES AS JANUS KINASE INHIBITORS

(71) Applicant: Merck Sharp & Dohme Corp., Rahway, NJ (US)

(72) Inventors: John W. Butcher, Berlin, MA (US); David Witter, Norfolk, MA (US); Christopher Dinsmore, Newton, MA (US); June Kim, West Chester, PA (US); John Hendrix, San Francisco, CA (US); Raksha Archarya, Bedford, MA (US); Sean P. Ahearn, Somerville, MA (US); Joon Jung, Newton, MA (US); Alexey Rivkin, Emeryville, CA (US); Philip Jones, Houston, TX (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/349,377

(22) PCT Filed: Sep. 28, 2012

(86) PCT No.: PCT/US2012/057695
§ 371 (c)(1),
(2) Date: Apr. 3, 2014

(87) PCT Pub. No.: WO2013/052355
PCT Pub. Date: Apr. 11, 2013

(65) Prior Publication Data
US 2014/0303142 A1    Oct. 9, 2014

Related U.S. Application Data

(60) Provisional application No. 61/542,542, filed on Oct. 3, 2011.

(51) Int. Cl.
| C07D 401/10 | (2006.01) |
| A61K 31/437 | (2006.01) |
| C07D 471/04 | (2006.01) |
| C07D 519/00 | (2006.01) |

(52) U.S. Cl.
CPC ............ C07D 471/04 (2013.01); C07D 519/00 (2013.01)

(58) Field of Classification Search
CPC .......................... C07D 401/10; A61K 31/437
USPC ........ 546/113; 514/300, 210.18, 242, 252.04, 514/253.04; 544/182, 238, 127, 362
See application file for complete search history.

(56) References Cited

U.S. PATENT DOCUMENTS

| 7,361,763 B2 * | 4/2008 | Arnold et al. ................. 546/113 |
| 7,361,764 B2 * | 4/2008 | Arnold et al. ................. 546/113 |
| 7,582,637 B2 * | 9/2009 | Arnold et al. ............ 514/253.04 |
| 2005/0261331 A1 | 11/2005 | Nielsen et al. |
| 2009/0306056 A1 | 12/2009 | Arnold et al. |

FOREIGN PATENT DOCUMENTS

| WO | 2006015123 | * | 2/2006 |
| WO | 2008005457 | * | 1/2008 |
| WO | 2008124849 | * | 10/2008 |

* cited by examiner

*Primary Examiner* — Niloofar Rahmani
(74) *Attorney, Agent, or Firm* — Patricia A. Shatynski; Catherine D. Fitch

(57) ABSTRACT

The instant invention provides compounds of formula I which are JAK inhibitors, and as such are useful for the treatment of JAK-mediated diseases such as rheumatoid arthritis, asthma, COPD and cancer.

6 Claims, No Drawings

AZAINDOLES AS JANUS KINASE INHIBITORS

BACKGROUND OF THE INVENTION

Studies of interferon (IFN)-induced receptor mediated gene expression led to the initial discovery of a Janus kinase (JAK) signaling pathway, which has been shown to be a common signaling pathway used by many cytokines and growth factors. The mammalian JAK family of intracellular tyrosine kinases, has four members; JAK1, JAK2, JAK3 and Tyk2. JAKs range in size from 120 to 140 kDa and contain seven conserved JAK homology (JH) domains which define this kinase super family.

Prototypically, the binding of a cytokine to its cell surface receptor results in receptor dimerization and subsequent activationphosphorylation of JAK tyrosine kinases which are constitutively associated with the receptor. Specific tyrosine residues on the receptor are then phosphorylated by activated JAKs and serve as docking sites for a family of latent cytoplasmic transcription factors known as Signal Transducers and Activators of Transcription (STATS). STATS are phosphorylated by JAKs, dimerize, then translocate to the nucleus where they bind specific DNA elements and activate gene transcription. Many pro-inflammatory cytokines (IL-6, IL-12, IL-15, IL-23, GM-CSF and IFN-γ) which are implicated in autoimmune diseases mediate their activity through the JAK kinases. As a consequence, these enzymes have long been considered attractive drug targets. The essential role of JAKs in mediating the biological effects of cytokines has been confirmed by natural mutations in humans and targeted disruption in mice. Humans with a genetic loss of JAK3 have a severe combined immunodefiency (SCID) phenotype due to a developmental block in T and NK cell development and nonfunctional B-cells. Humans lacking Tyk2 are susceptible to microbial infection, have a Th2 bias with Hyper-IgE syndrome and defective cytokine signaling (IL-6, 10, 12 and 23). Signaling can be restored by transfection of the wild type kinase.

Animal KO models of the JAK family of kinases have demonstrated significant phenotypes. JAK1 KO animals exhibit defective responses to class 2 cytokines (IL-10 family), those utilizing the common gamma chain $\gamma_c$ (IL-2, IL-4 etc) and gp130 receptor subunits (IL-6, LIF, OSM), resulting in perinatal lethality due to developmental, neurological and lymphoid defects. JAK2 KO mice exhibit defective erythropoiesis caused by a block in EPO signaling, resulting in embryonic lethality. JAK3 KO mice are viable but exhibit a SCID phenotype with nonfunctional T-cells and a lack of B and NK-cells (similar to human mutation). Tyk2 KO animals manifest modest viral susceptibility, reduced IL-12 responses, resistance to arthritis and enhanced Th2 cell-mediated allergic inflammation.

A considerable body of literature has accumulated that link the JAK/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I and pharmaceutically acceptable salts thereof:

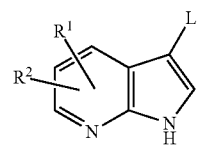

wherein L is chosen from:

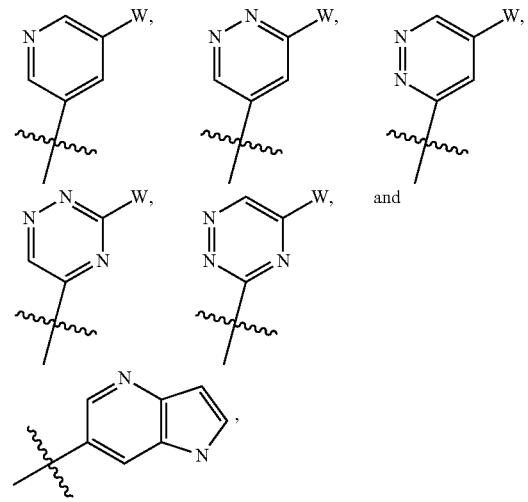

wherein L is substituted with 0, 1, 2, or 3 independently chosen $R^5$;

W is chosen from $C_{1-10}$ alkylamino, a ($C_{1-10}$)heteroalkyl containing 1, 2, or 3 atoms independently selected from N, O or S, a 3-15 member saturated, unsaturated or partially saturated monocyclic or bicyclic ring system containing 0, 1, 2, 3, or 4 atoms independently selected from N, O, or S, and —$NR^6R^6$ wherein two $R^6$ and the nitrogen to which they are attached can optionally form a -4, -5, or -6 member saturated ring system, and wherein W is substituted with 0, 1, 2 or 3 independently chosen $R^5$;

$R^1$, $R^2$ and $R^5$ are independently chosen from:
hydrogen,
halogen,
amino,
cyano,
—COOH,
$C_{1-10}$alkoxy,
hydroxy,
hydroxy $C_{0-10}$alkyl,
$C_{1-6}$ haloalkyl,
$C_{1-10}$ alkylsulfonyl,
($C_{0-10}$ alkyl)sulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino, $C_{3-8}$ cycloalkyl $C_{1-10}$ alkylsulfonylamino,
$(C_{0-10}$ alkyl$)_{1-2}$-aminosulfonyl,
$C_{1-10}$ alkyl(oxy)$_{0-1}C_{0-10}$ alkyl,
$C_{2-10}$ alkenyl(oxy)$_{0-1}C_{0-10}$ alkyl,
aryl$C_{0-10}$ alkyl(oxy)$_{0-1}C_{0-10}$ alkyl,
$(C_{3-8})$heteroaryl$C_{0-10}$ alkyl(oxy)$_{0-1}C_{0-10}$ alkyl,
$C_{3-8}$ cycloalkyl$C_{0-10}$ alkyl(oxy)$_{0-1}C_{0-10}$ alkyl,
$(C_{3-8})$heterocycloalkyl$C_{0-10}$ alkyl(oxy)$_{0-1}C_{0-10}$ alkyl,
$(C_{1-10})$heteroalkyl$C_{0-10}$ alkyl(oxy)$_{0-1}C_{0-10}$ alkyl,
(carbonyl)$_{0-1}C_{1-10}$ alkyl,
(carbonyl)$_{0-1}C_{2-10}$ alkenyl,
(carbonyl)$_{0-1}C_{2-10}$ alkynyl,
$C_{0-10}$ alkylcarbonyl(oxy)$_{0-1}C_{0-10}$ alkyl,
$C_{1-10}$ alkyl(oxy)$_{0-1}$carbonyl$C_{0-10}$ alkyl,
$C_{2-10}$ alkenylcarbonyl,
$C_{2-10}$ alkynylcarbonyl,
$C_{0-10}$ alkyl(oxy)$_{0-1}C_{1-10}$ alkyloxy$C_{0-10}$ alkyl,
$C_{0-10}$ alkyl(oxy)$_{0-1}C_{0-10}$ alkylaminocarbonyl$C_{0-10}$ alkyl,
$C_{0-10}$ alkylaminocarbonylaryl$C_{0-10}$ alkyl,
$C_{0-10}$ alkylaminocarbonyl$C_{1-10}$ heteroalkyl,
$C_{0-10}$ alkylaminocarbonyl$(C_{3-8})$heterocycloalkyl$C_{0-10}$ alkyl,
$C_{0-10}$ alkylaminocarbonyl$(C_{3-8})$heteroaryl$C_{0-10}$ alkyl,
$C_{0-10}$ alkylaminocarbonyl$(C_{3-8})$cycloalkyl$C_{0-10}$ alkyl,
$(C_{0-10}$ alkyl$)_{1-2}$-amino$C_{1-10}$ alkyloxy$C_{0-10}$ alkyl,
$(C_{0-10}$ alkyl$)_{1-2}$aminocarbonyl$C_{0-10}$ alkyl,
$C_{1-10}$ heteroalkyl$C_{0-10}$ alkylaminocarbonyl$C_{0-10}$ alkyl,
$(C_{3-8})$heterocycloalkyl$C_{0-10}$ alkylaminocarbonyl$C_{0-10}$ alkyl,
$(C_{3-8})$heteroaryl $C_{0-10}$ alkylaminocarbonyl$C_{0-10}$ alkyl,
$C_{3-8}$ cycloalkyl $C_{0-10}$ alkylaminocarbonyl$C_{0-10}$ alkyl,
aryl $C_{0-10}$ alkylaminocarbonyl$C_{0-10}$ alkyl,
$(C_{3-8})$heterocycloalkyl$C_{0-10}$ alkylcarbonyl$C_{0-10}$ alkyl,
$C_{1-10}$ alkyl(oxy)$_{0-1}C_{0-10}$ alkyl carbonylamino$C_{0-10}$ alkyl,
$C_{1-10}$ alkenyl(oxy)$_{0-1}$ $C_{0-10}$ alkyl carbonylamino$C_{0-10}$ alkyl,
$C_{1-10}$ heteroalkyl(oxy)$_{0-1}$-carbonylamino$C_{0-10}$ alkyl,
$C_{3-8}$ cycloalkyl$C_{0-10}$ alkyl(oxy)$_{0-1}$carbonylamino$C_{0-10}$ alkyl,
aryl $C_{0-10}$ alkyl(oxy)$_{0-1}$carbonylamino$C_{0-10}$ alkyl,
$(C_{3-8})$heteroaryl $C_{0-10}$ alkyl(oxy)$_{0-1}$carbonylamino$C_{0-10}$ alkyl,
$(C_{3-8})$heterocycloalkyl $C_{0-10}$ alkyl(oxy)$_{0-1}$carbonylamino $C_{0-10}$ alkyl,
$C_{0-10}$ alkylureylenyl,
$C_{1-4}$acylamino $C_{0-10}$ alkyl,
$C_{0-10}$ alkylamino $C_{0-10}$ alkyl,
aryl$C_{0-10}$ alkylamino $C_{0-10}$ alkyl,
$C_{3-8}$ cycloalkyl$C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
$(C_{1-10}$ alkyl$)_2$aminocarbonyloxy,
nitro,
halo-aryl,
halo-heterocyclyl,
cyano-aryl,
cyano-heteroaryl,
cyano-heterocyclyl, and
perfluoro$C_{1-6}$alkoxy;
$R^6$ is independently selected from:
hydrogen,
(carbonyl)$_{0-1}C_{1-10}$ alkyl,
(carbonyl)$_{0-1}C_{2-10}$ alkenyl,
(carbonyl)$_{0-1}C_{2-10}$ alkynyl,
$C_{0-10}$ alkylcarbonyl(oxy)$_{0-1}C_{0-10}$ alkyl,
$C_{1-10}$ alkyl(oxy)$_{0-1}$carbonyl$C_{0-10}$ alkyl,
$C_{2-10}$ alkenylcarbonyl,
$C_{2-10}$ alkynylcarbonyl,
$(C_{1-10})$alkyl(oxy)$_{0-1}C_{0-10}$ alkyl,
aryl(oxy)$_{0-1}C_{0-10}$ alkyl,
$(C_{3-8})$heteroaryl(oxy)$_{0-1}C_{0-10}$ alkyl,
$C_{3-8}$ cycloalkyl(oxy)$_{0-1}C_{0-10}$ alkyl,
$(C_{3-8})$heterocycloalkyl(oxy)$_{0-1}C_{0-10}$ alkyl,
$(C_{1-10})$heteroalkyl(oxy)$_{0-1}C_{0-10}$ alkyl,
$C_{0-10}$ alkyl(oxy)$_{0-1}C_{0-10}$ alkylaminocarbonyl$C_{0-10}$ alkyl,
$C_{0-10}$ alkylaminocarbonyl$C_{1-10}$ heteroalkyl,
$C_{0-10}$ alkylaminocarbonyl$(C_{3-8})$heterocycloalkyl$C_{0-10}$ alkyl,
$C_{0-10}$ alkylaminocarbonyl$(C_{3-8})$heteroaryl$C_{0-10}$ alkyl,
$C_{0-10}$ alkylaminocarbonyl$(C_{3-8})$cycloalkyl$C_{0-10}$ alkyl,
$C_{0-10}$ alkylaminocarbonylaryl$C_{0-10}$ alkyl,
hydroxy $C_{0-10}$alkyl,
$C_{0-10}$ alkylsulfonyl,
aryl $C_{1-10}$ alkylsulfonyl,
$C_{3-8}$ heterocyclyl $C_{1-10}$ alkylsulfonyl,
$C_{3-8}$ heterocycloalkyl $C_{1-10}$ alkylsulfonyl,
$C_{3-8}$ cycloalkyl $C_{1-10}$ alkylsulfonyl, and
$C_{1-6}$ haloalkyl;
wherein $R^1$, $R^2$, $R^5$ and $R^6$ are independently substituted with 0, 1, 2, or 3, substituents $R^3$ chosen from: halogen, $C_1$-$C_{10}$ alkyl, $CF_3$, $NH_2$, $N(C_1$-$C_6$ alkyl$)_2$, $NO_2$, —$(C_{0-6})$alkylCN, —OH, —O($C_1$-$C_6$ alkyl), $C_3$-$C_{10}$ cycloalkyl, $C_2$-$C_6$ alkenyl, $C_2$-$C_6$ alkynyl, $(C_0$-$C_6$ alkyl) S(O)$_{0-2}$—, $(C_0$-$C_6$ alkyl)S(O)$_{0-2}$ $(C_0$-$C_6$ alkyl)-, $(C_0$-$C_6$ alkyl)C(O)NH—, $H_2N$—C(NH)—, —O($C_1$-$C_6$ alkyl)$CF_3$, $(C_0$-$C_6$ alkyl)C(O)—, $(C_0$-$C_6$ alkyl)OC(O)—, $(C_0$-$C_6$ alkyl)O($C_1$-$C_6$ alkyl)-, $(C_0$-$C_6$ alkyl) C(O)$_{1-2}$($C_0$-$C_6$ alkyl)-, $(C_0$-$C_6$ alkyl)OC(O)NH—, —NH($C_1$-$C_6$ alkyl)NHC(O)NH($C_1$-$C_6$ alkyl), NHC(O)OC$_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), $C_{1-10}$alkoxy, —$CO_2$($C_{0-10}$ alkyl), Oxo (=O), trifluoromethyl, trifluoroethyl, $C_{1-10}$ alkylsulfonyl, —SO$_2$N($C_{1-6}$alkyl)$_{1-2}$, —SO$_2$CF$_3$, —SO$_2$CF$_2$H, —$C_{1-10}$alkylsulfinyl, —$O_{(0-1)}$($C_{1-10}$)haloalkyl, aryl, heteroaryl, heterocyclyl, halo-aryl, halo-heterocyclyl, cyano-aryl, cyano-heteroaryl, and cyano-heterocyclyl.

Representative compounds of the instant invention include, but are not limited to, the following compounds and their pharmaceutically acceptable salts:

(2R)-2-{[5-(5-chloro-1H-pyrrolo[2,3-b]pyridin-3-yl)pyridin-3-yl]amino}-3-methyl-N-(2,2,2-trifluoroethyl)butanamide;

2-{[5-(5-fluoro-1H-pyrrolo[2,3-b]pyridin-3-yl)pyridin-3-yl]amino}-3-methyl-N-(2,2,2-trifluoroethyl)butanamide;

N~2~-[3-(5-chloro-1H-pyrrolo[2,3-b]pyridin-3-yl)-1,2,4-triazin-5-yl]-N-(2,2,2-trifluoroethyl)-D-valinamide;

7-[3-(5-chloro-1H-pyrrolo[2,3-b]pyridin-3-yl)-1,2,4-triazin-5-yl]-8-methyl-3-(trifluoromethyl)-5,6,7,8-tetrahydroimidazo[1,2-a]pyrazine;

5-chloro-3-{5-[2-(1,3-thiazol-2-yl)pyrrolidin-1-yl]-1,2,4-triazin-3-yl}-1H-pyrrolo[2,3-b]pyridine;

N~2~-[3-(5-fluoro-1H-pyrrolo[2,3-b]pyridin-3-yl)-1,2,4-triazin-5-yl]-2-methyl-N-(2,2,2-trifluoroethyl)alaninamide;

N~2~-[3-(5-cyano-1H-pyrrolo[2,3-b]pyridin-3-yl)-1,2,4-triazin-5-yl]-2-methyl-N-(2,2,2-trifluoroethyl)alaninamide;

N~2~-[3-(5-fluoro-1H-pyrrolo[2,3-b]pyridin-3-yl)-1,2,4-triazin-5-yl]-N-(2,2,2-trifluoroethyl)-D-alaninamide;

N~2~-[3-(5-cyano-1H-pyrrolo[2,3-b]pyridin-3-yl)-1,2,4-triazin-5-yl]-N-(2,2,2-trifluoroethyl)-D-alaninamide;

7-[3-(5-fluoro-1H-pyrrolo[2,3-b]pyridin-3-yl)-1,2,4-triazin-5-yl]-8-methyl-3-(trifluoromethyl)-5,6,7,8-tetrahydroimidazo[1,2-a]pyrazine;

5-fluoro-3-{5-[2-(1,3-thiazol-2-yl)pyrrolidin-1-yl]-1,2,4-triazin-3-yl}-1H-pyrrolo[2,3-b]pyridine;

3-{5-[2-(1,3-thiazol-2-yl)pyrrolidin-1-yl]-1,2,4-triazin-3-yl}-1H-pyrrolo[2,3-b]pyridine-5-carbonitrile;

3-[5-({1,1-dimethyl-2-oxo-2-[(2,2,2-trifluoroethyl)amino]ethyl}amino)-1,2,4-triazin-3-yl]-1H-pyrrolo[2,3-b]pyridine-5-carboxamide;

3-[5-({(1R)-1-methyl-2-oxo-2-[(2,2,2-trifluoroethyl)amino] ethyl}amino)-1,2,4-triazin-3-yl]-1H-pyrrolo[2,3-b]pyridine-5-carboxamide;
3-{5-[8-methyl-3-(trifluoromethyl)-5,6-dihydroimidazo[1,2-a]pyrazin-7(8H)-yl]-1,2,4-triazin-3-yl}-1H-pyrrolo[2,3-b]pyridine-5-carboxamide;
N~2~-[3-(5-fluoro-1H-pyrrolo[2,3-b]pyridin-3-yl)-1,2,4-triazin-5-yl]-N-(2,2,2-trifluoroethyl)-D-valinamide;
N~2~-[3-(5-cyano-1H-pyrrolo[2,3-b]pyridin-3-yl)-1,2,4-triazin-5-yl]-N-(2,2,2-trifluoroethyl)-D-valinamide;
3-[5-({(1R)-2-methyl-1-[(2,2,2-trifluoroethyl)carbamoyl] propyl}amino)-1,2,4-triazin-3-yl]-1H-pyrrolo[2,3-b]pyridine-5-carboxamide;
(1S,2R)-2-{[3-(5-chloro-1H-pyrrolo[2,3-b]pyridin-3-yl)-1,2,4-triazin-5-yl]amino}-N-(2,2,2-trifluoroethyl)cyclohexanecarboxamide;
N~2~-[3-(5-methoxy-1H-pyrrolo[2,3-b]pyridin-3-yl)-1,2,4-triazin-5-yl]-N-(2,2,2-trifluoroethyl)-D-valinamide;
(1S,2R)-2-{[3-(5-fluoro-1H-pyrrolo[2,3-b]pyridin-3-yl)-1,2,4-triazin-5-yl]amino}-N-(2,2,2-trifluoroethyl)cyclohexanecarboxamide;
(1S,2R)-2-{[3-(5-cyano-1H-pyrrolo[2,3-b]pyridin-3-yl)-1,2,4-triazin-5-yl]amino}-N-(2,2,2-trifluoroethyl)cyclohexanecarboxamide;
3-[5-({(1R,2S)-2-[(2,2,2-trifluoroethyl)carbamoyl] cyclohexyl}amino)-1,2,4-triazin-3-yl]-1H-pyrrolo[2,3-b] pyridine-5-carboxamide;
N~2~-[6-(5-chloro-1H-pyrrolo[2,3-b]pyridin-3-yl)pyridazin-4-yl]-N-(2,2,2-trifluoroethyl)-D-alaninamide;
N-(2,2,2-trifluoroethyl)-N~2~-{6-[5-(trifluoromethyl)-1H-pyrrolo[2,3-b]pyridin-3-yl]pyridazin-4-yl}-D-alaninamide;
5-chloro-3-{5-[2-(1,3-thiazol-2-yl)pyrrolidin-1-yl]pyridazin-3-yl}-1H-pyrrolo[2,3-b]pyridine;
N~2~-[5-(5-chloro-1H-pyrrolo[2,3-b]pyridin-3-yl)pyridin-3-yl]-2-methyl-N-(2,2,2-trifluoroethyl)alaninamide;
5-chloro-3-{5-[2-(1,3-thiazol-2-yl)pyrrolidin-1-yl]pyridin-3-yl}-1Hr-pyrrolo[2,3-b]pyridine;
N~2~-[5-(5-chloro-1H-pyrrolo[2,3-b]pyridin-3-yl)pyridin-3-yl]-N-(2,2,2-trifluoroethyl)-D-alaninamide;
N~2~-[5-(5-fluoro-1H-pyrrolo[2,3-b]pyridin-3-yl)pyridin-3-yl]-N-(2,2,2-trifluoroethyl)-D-alaninamide;
N~2~-[5-(5-methoxy-1H-pyrrolo[2,3-b]pyridin-3-yl)pyridin-3-yl]-N-(2,2,2-trifluoroethyl)-D-alaninamide;
N~2~-[5-(5-cyano-1H-pyrrolo[2,3-b]pyridin-3-yl)pyridin-3-yl]-N-(2,2,2-trifluoroethyl)-D-alaninamide;
R)-2-{[5-(5-chloro-1H-pyrrolo[2,3-b]pyridin-3-yl)pyridin-3-yl]amino}-N-(2,2,2-trifluoroethyl)cyclohexanecarboxamide;
N~2~-{5-[5-(methylsulfonyl)-1H-pyrrolo[2,3-b]pyridin-3-yl]pyridin-3-yl}-N-(2,2,2-trifluoroethyl)-D-alaninamide;
2-[6-(5-chloro-1H-pyrrolo[2,3-b]pyridin-3-yl)-1H-pyrrolo[3,2-b]pyridin-1-yl]-N-(2,2,2-trifluoroethyl)propanamide;
N~2~-[5-(5-chloro-4-fluoro-1H-pyrrolo[2,3-b]pyridin-3-yl) pyridin-3-yl]-N-(2,2,2-trifluoroethyl)-D-alaninamide;
(1S,2R)-2-{[5-(5-fluoro-1H-pyrrolo[2,3-b]pyridin-3-yl)pyridin-3-yl]amino}-N-(2,2,2-trifluoroethyl)cyclohexanecarboxamide;
(1S,2R)-2-{[5-(5-cyano-1H-pyrrolo[2,3-b]pyridin-3-yl)pyridin-3-yl]amino}-N-(2,2,2-trifluoroethyl)cyclohexanecarboxamide;
N~2~-[5-(5-chloro-1H-pyrrolo[2,3-b]pyridin-3-yl)-2-fluoropyridin-3-yl]-N-(2,2,2-trifluoroethyl)alaninamide;
3-[5-({(1R,2S)-2-[(2,2,2-trifluoroethyl)carbamoyl] cyclohexyl}amino)pyridin-3-yl]-1H-pyrrolo[2,3-b]pyridine-5-carboxamide;
N~2~-[5-(5-cyano-1H-pyrrolo[2,3-b]pyridin-3-yl)pyridin-3-yl]-N-(2,2,2-trifluoroethyl)valinamide;
3-[5-({2-methyl-1-[(2,2,2-trifluoroethyl)carbamoyl] propyl}amino)pyridin-3-yl]-1H-pyrrolo[2,3-b]pyridine-5-carboxamide;
N~2~-[5-(5-fluoro-1H-pyrrolo[2,3-b]pyridin-3-yl)pyridin-3-yl]-2-methyl-N-(2,2,2-trifluoroethyl)alaninamide;
N~2~-[5-(5-cyano-1H-pyrrolo[2,3-b]pyridin-3-yl)pyridin-3-yl]-2-methyl-N-(2,2,2-trifluoroethyl)alaninamide;
N~2~-[5-(5-methoxy-1H-pyrrolo[2,3-b]pyridin-3-yl)pyridin-3-yl]-N-(2,2,2-trifluoroethyl)valinamide;
3-[5-({(1R)-1-methyl-2-oxo-2-[(2,2,2-trifluoroethyl)amino] ethyl}amino)pyridin-3-yl]-1H-pyrrolo[2,3-b]pyridine-5-carboxamide;
3-[5-({1,1-dimethyl-2-oxo-2-[(2,2,2-trifluoroethyl)amino] ethyl}amino)pyridin-3-yl]-1H-pyrrolo[2,3-b]pyridine-5-carboxamide;
2-{[5-(5-chloro-1H-pyrrolo[2,3-b]pyridin-3-yl)pyridin-3-yl]amino}-2-cyclopropyl-N-(2,2,2-trifluoroethyl)acetamide;
N~2~-[5-(5-chloro-1H-pyrrolo[2,3-b]pyridin-3-yl)pyridin-3-yl]-3-hydroxy-N-(2,2,2-trifluoroethyl)-D-valinamide;
3-hydroxy-N~2~-[5-(5-methoxy-1H-pyrrolo[2,3-b]pyridin-3-yl)pyridin-3-yl]-N-(2,2,2-trifluoroethyl)-D-valinamide;
N~2~-[5-(5-chloro-1H-pyrrolo[2,3-b]pyridin-3-yl)pyridin-3-yl]-N-(2,2,2-trifluoroethyl)-D-valinamide;
N~2~-[5-(5-chloro-1H-pyrrolo[2,3-b]pyridin-3-yl)pyridin-3-yl]-N-(2,2,2-trifluoroethyl)-L-valinamide;
2-{[5-(5-hydroxy-1H-pyrrolo[2,3-b]pyridin-3-yl)pyridin-3-yl]amino}-3-methyl-N-(2,2,2-trifluoroethyl)butanamide;
2-{[5-(5-hydroxy-1H-pyrrolo[2,3-b]pyridin-3-yl)pyridin-3-yl]amino}-3-methyl-N-(2,2,2-trifluoroethyl)butanamide;
N~2~-{5-[5-(1-methylethoxy)-1H-pyrrolo[2,3-b]pyridin-3-yl]pyridin-3-yl}-N-(2,2,2-trifluoroethyl)-D-valinamide;
N~2~-{5-[5-(benzyloxy)-1H-pyrrolo[2,3-b]pyridin-3-yl] pyridin-3-yl}-N-(2,2,2-trifluoroethyl)valinamide;
N~2~-{5-[5-(cyclopentyloxy)-1H-pyrrolo[2,3-b]pyridine-3-yl]pyridin-3-yl}-N-(2,2,2-trifluoroethyl)valinamide;
N~2~-{5-[5-(cyclopropylmethoxy)-1H-pyrrolo[2,3-b]pyridin-3-yl]pyridin-3-yl}-N-(2,2,2-trifluoroethyl)valinamide;
N~2~-{5-[5-(2-phenylethoxy)-1H-pyrrolo[2,3-b]pyridin-3-yl]pyridin-3-yl}-N-(2,2,2-trifluoroethyl)valinamide;
N~2~-{5-[5-(2,3-dihydro-1H-inden-2-yloxy)-1H-pyrrolo[2,3-b]pyridin-3-yl]pyridin-3-yl}-N-(2,2,2-trifluoroethyl) valinamide;
N~2~-{5-[5-(tetrahydro-2H-pyran-4-yloxy)-1H-pyrrolo[2,3-b]pyridin-3-yl]pyridin-3-yl}-N-(2,2,2-trifluoroethyl) valinamide;
N~2~-(5-{5-[2-(2-oxopyrrolidin-1-yl)ethoxy]-1H-pyrrolo [2,3-b]pyridin-3-yl}pyridin-3-yl)-N-(2,2,2-trifluoroethyl) valinamide;
N~2~-{5-[5-(pyridin-3-ylmethoxy)-1H-pyrrolo[2,3-b]pyridin-3-yl]pyridin-3-yl}-N-(2,2,2-trifluoroethyl)valinamide;
N~2~-{5-[5-(2-pyridin-2-ylethoxy)-1H-pyrrolo[2,3-b]pyridin-3-yl]pyridin-3-yl}-N-(2,2,2-trifluoroethyl)valinamide;
N~2~-(5-{5-[2-(dimethylamino)ethoxy]-1H-pyrrolo[2,3-b] pyridin-3-yl}pyridin-3-yl)-N-(2,2,2-trifluoroethyl)valinamide;
N~2~-(5-{5-[3-(dimethylamino)propoxy]-1H-pyrrolo[2,3-b]pyridin-3-yl}pyridin-3-yl)-N-(2,2,2-trifluoroethyl)valinamide;
N~2~-{5-[5-(2-morpholin-4-ylethoxy)-1H-pyrrolo[2,3-b] pyridin-3-yl]pyridin-3-yl}-N-(2,2,2-trifluoroethyl)valinamide;

N~2~-(5-{5-[(1-methylpiperidin-4-yl)oxy]-1H-pyrrolo[2,3-b]pyridin-3-yl}pyridin-3-yl)-N-(2,2,2-trifluoroethyl)valinamide;

N~2~-(5-{5-[2-(4-methylpiperazin-1-yl)ethoxy]-1H-pyrrolo[2,3-b]pyridin-3-yl}pyridin-3-yl)-N-(2,2,2-trifluoroethyl)valinamide;

N~2~-(5-{5-[(1-methylpiperidin-4-yl)methoxy]-1H-pyrrolo[2,3-b]pyridin-3-yl}pyridin-3-yl)-N-(2,2,2-trifluoroethyl)valinamide;

(R)—N,N-dimethyl-3-(5-(3-methyl-1-oxo-1-(2,2,2-trifluoroethylamino) butan-2-ylamino)pyridin-3-yl)-1H-pyrrolo[2,3-b]pyridine-5-carboxamide;

N-(1-methylethyl)-3-[5-({(1R)-2-methyl-1-[(2,2,2-trifluoroethyl) carbamoyl]propyl}amino)pyridin-3-yl]-1H-pyrrolo[2,3-b]pyridine-5-carboxamide;

N-(2-methoxy-1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

N-(2-hydroxy-1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

3-[5-({(1R)-2-methyl-1-[(2,2,2-trifluoroethyl)carbamoyl]propyl}amino)pyridine-3-yl]-Netrahydro-2H-pyran-4-yl)-1H-pyrrolo[2,3-b]pyridine-5-carboxamide;

N~2~-{5-[5-(azetidin-1-ylcarbonyl)-1H-pyrrolo[2,3-b]pyridin-3-yl]pyridin-3-yl}-N-(2,2,2-trifluoroethyl)-D-valinamide;

N-(2-methylpropyl)-3-[5-({(1R)-2-methyl-1-[(2,2,2-trifluoroethyl) carbamoyl]propyl}amino)pyridin-3-yl]-1H-pyrrolo[2,3-b]pyridine-5-carboxamide;

N-methyl-3-[5-({(1R)-2-methyl-1-[(2,2,2-trifluoroethyl)carbamoyl]propyl}amino) pyridin-3-yl]-1H-pyrrolo[2,3-b]pyridine-5-carboxamide;

N-[1-dioxidotetrahydrothiophen-3-yl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

3-[5-({(1R)-2-methyl-1-[(2,2,2-trifluoroethyl)carbamoyl]propyl}amino) pyridin-3-yl]-N-(1H-pyrazol-5-ylmethyl)-1H-pyrrolo[2,3-b]pyridine-5-carboxamide;

N-methyl-3-[5-({(1R)-2-methyl-1-[(2,2,2-trifluoroethyl)carbamoyl]propyl}amino) pyridin-3-yl]-N-[1-(1H-pyrazol-5-yl)ethyl]-1H-pyrrolo[2,3-b]pyridine-5-carboxamide;

N-[(1-methyl-1H-pyrazol-4-yl)methyl]-3-[5-({(1R)-2-methyl-1-[(2,2,2-trifluoroethyl)carbamoyl]propyl}amino) pyridin-3-yl]-1H-pyrrolo[2,3-b]pyridine-5-carboxamide;

N~2~-(5-{5-[(4-hydroxypiperidin-1-yl)carbonyl]-1H-pyrrolo[2,3-b]pyridin-3-yl}pyridin-3-yl)-N-(2,2,2-trifluoroethyl)-D-valinamide;

N-[(1-hydroxycyclopropyl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

3-Methyl-2-(5-(5-sulfamoyl-1H-pyrrolo[2,3-b]pyridin-3-yl)pyridin-3-ylamino)-N-(2,2,2-trifluoroethyl)butanamide;

2-(5-(5-(N,N-dimethylsulfamoyl)-1H-pyrrolo[2,3-b]pyridin-3-yl)pyridin-3-ylamino)-3-methyl-N-(2,2,2-trifluoroethyl)butanamide;

N2-[5-(5-amino-1H-pyrrolo[2,3-b]pyridin-3-yl)pyridin-3-yl]-N-(2,2,2-trifluoroethyl)valinamide;

N2-{5-[5-(acetyl amino)-1H-pyrrolo[2,3-b]pyridin-3-yl]pyridin-3-yl}-N-(2,2,2-trifluoroethyl)valinamide;

N2-(5-{5-[(methylsulfonyl)amino]-1H-pyrrolo[2,3-b]pyridin-3-yl}pyridin-3-yl)-N-(2,2,2-trifluoroethyl)valinamide;

N2-(5-{5-[(methylsulfonyl)amino]-1H-pyrrolo[2,3-b]pyridin-3-yl}pyridin-3-yl)-N-(2,2,2-trifluoroethyl)-L-valinamide;

N2-(5-{5-[(methylsulfonyl)amino]-1H-pyrrolo[2,3-b]pyridin-3-yl}pyridin-3-yl)-N-(2,2,2-trifluoroethyl)-D-valinamide;

N2-{5-[5-(propanoylamino)-1H-pyrrolo[2,3-b]pyridin-7-ium-3-yl]pyridin-3-yl}-N-(2,2,2-trifluoroethyl)valinamide;

N~2~-(5-{5-[(hydroxyacetyl)amino]-1H-pyrrolo[2,3-b]pyridin-3-yl}pyridin-3-yl)-N-(2,2,2-trifluoroethyl)valinamide;

N~2~-(5-{5-[(methoxyacetyl)amino]-1H-pyrrolo[2,3-b]pyridin-3-yl}pyridin-3-yl)-N-(2,2,2-trifluoroethyl)valinamide;

N2-(5-{5-[(propan-2-ylcarbamoyl)amino]-1H-pyrrolo[2,3-b]pyridin-3-yl}pyridin-3-yl)-N-(2,2,2-trifluoroethyl)valinamide;

N~2~-(5-{5-[(propylcarbamoyl)amino]-1H-pyrrolo[2,3-b]pyridin-3-yl}pyridin-3-yl)-N-(2,2,2-trifluoroethyl)valinamide;

N~2~-[5-(5-{[(2,4-difluorophenyl)carbamoyl]amino}-1H-pyrrolo[2,3-b]pyridin-3-yl)pyridin-3-yl]-N-(2,2,2-trifluoroethyl)valinamide;

N-({3-[5-({2-methyl-1-[(2,2,2-trifluoroethyl)carbamoyl]propyl}amino)pyridin-3-yl]-1H-pyrrolo[2,3-b]pyridin-5-yl}carbamoyl)alanine;

N~2~-(5-{5-[(methylcarbamoyl)amino]-1H-pyrrolo[2,3-b]pyridin-3-yl}pyridin-3-yl)-N-(2,2,2-trifluoroethyl)valinamide;

Methyl {3-[5-({3-methyl-1-oxo-1-[(2,2,2-trifluoroethyl)amino]butan-2-yl}amino)pyridin-3-yl]-1H-pyrrolo[2,3-b]pyridin-5-yl}carbamate;

ethyl {3-[5-({2-methyl-1-[(2,2,2-trifluoroethyl)carbamoyl]propyl}amino) pyridin-3-yl]-1H-pyrrolo[2,3-b]pyridin-5-yl}carbamate;

1-methylethyl {3-[5-({2-methyl-1-[(2,2,2-trifluoroethyl)carbamoyl]propyl}amino)pyridin-3-yl]-1H-pyrrolo[2,3-b]pyridin-5-yl}carbamate;

N2-{5-[5-(1-methyl-1H-pyrazol-4-yl)-1H-pyrrolo[2,3-b]pyridin-3-yl]pyridin-3-yl}-N-(2,2,2-trifluoroethyl)valinamide;

N2-{5-[5-(1-methyl-1H-pyrazol-4-yl)-1H-pyrrolo[2,3-b]pyridin-3-yl]pyridin-3-yl}-N-(2,2,2-trifluoroethyl)-L-valinamide;

N2-{5-[5-(1-methyl-1H-pyrazol-4-yl)-1H-pyrrolo[2,3-b]pyridin-3-yl]pyridin-3-yl}-N-(2,2,2-trifluoroethyl)-D-valinamide;

(R)-3-methyl-2-(5-(5-((2-(pyrrolidin-1-yl)ethoxy)methyl)-1H-pyrrolo[2,3-b]pyridin-3-yl)pyridin-3-ylamino)-N-(2,2,2-trifluoroethyl)butanamide;

N~2~-{5-[5-(tert-butoxymethyl)-1H-pyrrolo[2,3-b]pyridine-3-yl]pyridin-3-yl}-N-(2,2,2-trifluoroethyl)-D-valinamide;

tert-butyl 4-[2-({3-[5-({(1R)-2-methyl-1-[(2,2,2-trifluoroethyl)carbamoyl]propyl}amino)pyridin-3-yl]-1H-pyrrolo[2,3-b]pyridin-5-yl}methoxy)ethyl]piperazine-1-carboxylate;

N~2~-(5-{5-[(2-morpholin-4-ylethoxy)methyl]-1H-pyrrolo[2,3-b]pyridin-3-yl}pyridin-3-yl)-N-(2,2,2-trifluoroethyl)-D-valinamide;

N~2~-(5-{5-[(prop-2-en-1-yloxy)methyl]-1H-pyrrolo[2,3-b]pyridin-3-yl}pyridin-3-yl)-N-(2,2,2-trifluoroethyl)-D-valinamide;

tert-butyl 4-({3-[5-({(1R)-2-methyl-1-[(2,2,2-trifluoroethyl)carbamoyl]propyl}amino)pyridin-3-yl]-1H-pyrrolo[2,3-b]pyridin-5-yl}methoxy)piperidine-1-carboxylate;

N~2~-{5-[5-(pyrrolidin-1-ylmethyl)-1H-pyrrolo[2,3-b]pyridin-3-yl]pyridin-3-yl}-N-(2,2,2-trifluoroethyl)-D-valinamide;

N~2~-{3-[5-(methoxymethyl)-1H-pyrrolo[2,3-b]pyridin-3-yl]-1,2,4-triazin-5-yl}-N-(2,2,2-trifluoroethyl)-D-valinamide;

N~2~-{5-[5-(methoxymethyl)-1H-pyrrolo[2,3-b]pyridin-3-yl]pyridin-3-yl}-N-(2,2,2-trifluoroethyl)-D-valinamide;

N-((3-(5-(3-methyl-1-oxo-1-(2,2,2-trifluoroethylamino)butan-2-ylamino)pyridin-3-yl)-1H-pyrrolo[2,3-b]pyridin-5-yl)methyl)cyclopentanecarboxamide;

N~2~-(5-{5-[(propanoylamino)methyl]-1H-pyrrolo[2,3-b]pyridin-3-yl}pyridin-3-yl)-N-(2,2,2-trifluoroethyl)valinamide;

N-({3-[5-({2-methyl-1-[(2,2,2-trifluoroethyl)carbamoyl]propyl}amino) pyridin-3-yl]-1-pyrrolo[2,3-b]pyridin-5-yl}methyl)cyclohexanecarboxamide;

N~2~-[5-(5-{[(2E)-but-2-enoylamino]methyl}-1H-pyrrolo[2,3-b]pyridin-3-yl)pyridin-3-yl]-N-(2,2,2-trifluoroethyl)valinamide;

N~2~-(5-{5-[(acetylamino)methyl]-1H-pyrrolo[2,3-b]pyridin-3-yl}pyridin-3-yl)-N-(2,2,2-trifluoroethyl)valinamide;

N~2~-[5-(5-{[(cyclopropylcarbonyl)amino]methyl}-1H-pyrrolo[2,3-b]pyridin-3-yl)pyridin-3-yl]-N-(2,2,2-trifluoroethyl)valinamide;

N~2~-{5-[5-({[(4-methyl-1,3-oxazol-5-yl)carbonyl]amino}methyl)-1H-pyrrolo[2,3-b]pyridin-3-yl]pyridin-3-yl}-N-(2,2,2-trifluoroethyl)valinamide;

N~2~-[5-(5-{[(3-methylbut-2-enoyl)amino]methyl}-1H-pyrrolo[2,3-b]pyridin-3-yl)pyridin-3-yl]-N-(2,2,2-trifluoroethyl)valinamide;

N~2~-(5-{5-[(butanoylamino)methyl]-1H-pyrrolo[2,3-b]pyridin-3-yl}pyridin-3-yl)-N-(2,2,2-trifluoroethyl)valinamide;

N-(2,2,2-trifluoroethyl)-N~2~-[5-(5-{[(3,3,3-trifluoropropanoyl)amino]methyl}-1H-pyrrolo[2,3-b]pyridin-3-yl)pyridin-3-yl]valinamide; and N~2~-[5-(5-{[(pyrrolidin-1-ylcarbonyl)amino]methyl}-1H-pyrrolo[2,3-b]pyridin-3-yl)pyridin-3-yl]-N-(2,2,2-trifluoroethyl)valinamide.

The invention also encompasses pharmaceutical compositions containing a compound of formula I, and methods for treatment or prevention of JAK mediated diseases using compounds of formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

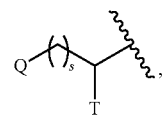

wherein s is an integer equal to zero, 1 or 2, the structure is

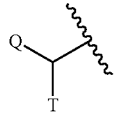

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

"Halo-aryl" refers to an aryl group as described above in which one or more hydrogen atoms have been replaced by a halogen group.

"Cyano-aryl" refers to an aryl group as described above in which one atom has been replaced by a cyano group.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

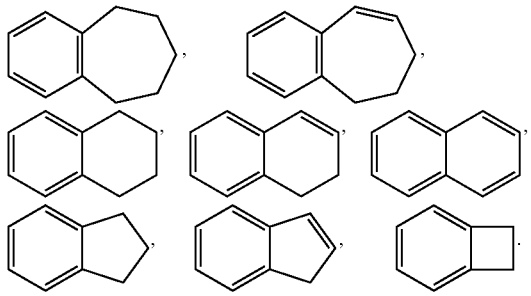

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Cyanoalkyl" refers to an alkyl group as described above in which one hydrogen atom has been replaced by a cyano group. Examples include $CH_2CN$, $CH_2CH_2CN$ and $CH(CN)CH_3$.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes $-CF_3$, $-CF_2CF_3$, $CHFCH_3$, and the like.

"Heterocycle" or "heterocyclic" represents a monocyclic or bicyclic 4-10 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. Examples of heterocycle include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl and the like.

Saturated heterocyclics form a subset of the heterocycles; i.e., the terms "saturated heterocyclic and $(C_{3-8})$heterocycloalkyl" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

"Heteroaryl" or "heteroaromatic" as used herein represents a 5-10 membered aromatic ring system containing one ring (monocyclic) or two fused rings (bicyclic), and 1-4 heteroatoms independently selected from O, S and N.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsatuated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

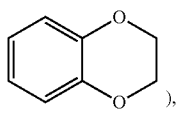), imidazo(2,1-b)(1,3)thiazole, (i.e.,

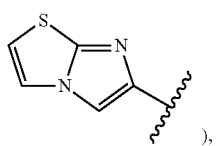 [SMILES: *c1cn2ccsc2n1]), and benzo-1,3-dioxolyl (i.e.,

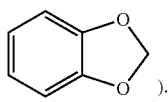).

In certain contexts herein,

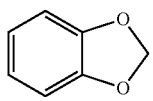

is alternatively referred to as phenyl having as a substituent methylenedioxy attached to two adjacent carbon atoms.

"Cyano-heteroaryl" and "cyano-heterocyclyl" refer to a heteroaryl and a heterocyclyl group, respectively, as described above in which one atom has been replaced by a cyano group.

"Halo-heteroaryl" and "halo-heterocyclyl" refer to a heteroaryl and a heterocyclyl group, respectively, as described above in which one or more atoms have been replaced by a halogen group.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

The term "ureylenyl" refers to: —NH—CO—NH—.

Non-limiting examples of azaindoles include: 4-azaindolyl (1H-pyrrolo[3,2-b]pyridinyl), 5-azaindolyl, 6-azaindolyl, and 7-azaindolyl. Non-limiting examples of diazaindoles include: purinyl, isoindazoylyl (benzpyrazolyl), 4-azabenzimidazole, 5-azabenzimidazole, 6-azabenzimidazole, and 7-azabenzimidazole.

Structural representations of compounds having substituents terminating with a methyl group may display the terminal methyl group either using the characters "$CH_3$", e.g. "—$CH_3$" or using a straight line representing the presence of the methyl group, e.g. "—", i.e.,

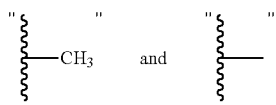

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

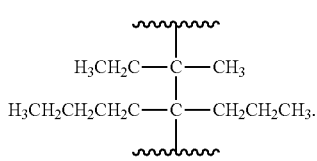

One embodiment of the invention is a compound of formula I:

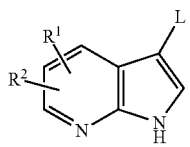

I or a pharmaceutically acceptable salt thereof; wherein L is chosen from:

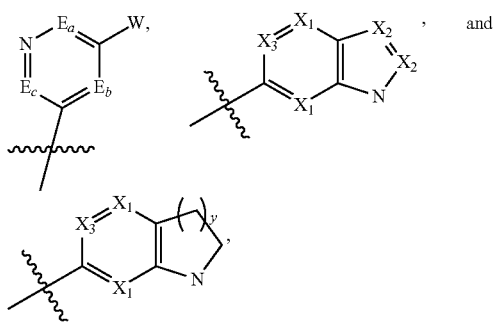

wherein $E_a$, $E_b$, and $E_c$, are each independently C or N, and $X_1$, $X_2$, and $X_3$ are each independently C or N, provided that when $E_a$ and $E_c$ are each C then $E_b$ must be C, wherein L is optionally substituted with 1, 2, or 3 independently chosen $R^5$;

W is chosen from $C_{1-10}$ alkylamino, a $(C_{1-10})$heteroalkyl containing 1, 2, or 3 atoms independently selected from N, O or S, a 3-15 member saturated, unsaturated or partially saturated monocyclic or bicyclic ring system containing 0, 1, 2, 3, or 4 atoms independently selected from N, O, or S, —$NR^6R^6$ wherein two $R^6$ and the nitrogen to which they are attached can optionally form a -4, -5, or -6 member saturated ring system, and wherein W is substituted with 0, 1, 2 or 3 independently chosen $R^5$;

y is 0, 1, 2 or 3;

$R^1$, $R^2$ and $R^5$ are independently chosen from: hydrogen, halogen, amino, cyano, —COOH, $C_{1-10}$alkoxy, hydroxy, hydroxy $C_{0-10}$alkyl, $C_{1-6}$ haloalkyl, $C_{1-10}$ alkylsulfonyl, $(C_{0-10}$ alkyl)sulfonylamino, aryl $C_{1-10}$ alkylsulfonylamino, $C_{3-8}$ heterocyclyl $C_{1-10}$ alkylsulfonylamino, $C_{3-8}$ heterocycloalkyl $C_{1-10}$ alkylsulfonylamino, $C_{3-8}$ cycloalkyl $C_{1-10}$ alkylsulfonylamino, $(C_{0-10}$ alkyl$)_{1-2}$aminosulfonyl, $C_{1-10}$ alkyl(oxy)$_{0-1}C_{0-10}$ alkyl, $C_{2-10}$ alkenyl(oxy)$_{0-1}C_{0-10}$ alkyl, aryl$C_{0-10}$ alkyl (oxy)$_{0-1}C_{0-10}$ alkyl, $(C_{3-8})$heteroaryl$C_{0-10}$ alkyl(oxy)$_{0-1}$ $C_{0-10}$ alkyl, $C_{3-8}$ cycloalkyl$C_{0-10}$ alkyl(oxy)$_{0-1}C_{0-10}$ alkyl, $(C_{3-8})$heterocycloalkyl$C_{0-10}$ alkyl(oxy)$_{0-1}C_{0-10}$ alkyl, $(C_{1-10})$heteroalkyl$C_{0-10}$ alkyl(oxy)$_{0-1}C_{0-10}$ alkyl, (carbonyl)$_{0-1}C_{1-10}$ alkyl, (carbonyl)$_{0-1}C_{2-10}$ alkenyl, (carbonyl)$_{0-1}C_{2-10}$ alkynyl, $C_{0-10}$ alkylcarbonyl(oxy)$_{0-1}$ $C_{0-10}$ alkyl, $C_{1-10}$ alkyl(oxy)$_{0-1}$carbonyl$C_{0-10}$ alkyl, $C_{2-10}$ alkenylcarbonyl, $C_{2-10}$ alkynylcarbonyl, $C_{0-10}$ alkyl(oxy)$_{0-1}C_{1-10}$ alkyloxy$C_{0-10}$ alkyl, $C_{0-10}$ alkyl (oxy)$_{0-1}C_{0-10}$ alkylaminocarbonyl$C_{0-10}$ alkyl, $C_{0-10}$ alkylaminocarbonylaryl$C_{0-10}$ alkyl, $C_{0-10}$ alkylaminocarbonyl$C_{1-10}$ heteroalkyl, $C_{0-10}$ alkylaminocarbonyl $(C_{3-8})$heterocycloalkyl$C_{0-10}$ alkyl, $C_{0-10}$ alkylaminocarbonyl$(C_{3-8})$heteroaryl$C_{0-10}$ alkyl, $C_{0-10}$ alkylaminocarbonyl$(C_{3-8})$cycloalkyl$C_{0-10}$ alkyl, $(C_{0-10}$ alkyl)$_{1-2}$-amino$C_{1-10}$ alkyloxy$C_{0-10}$ alkyl, $(C_{0-10}$ alkyl)$_{1-2}$-aminocarbonyl$C_{0-10}$ alkyl, $C_{1-10}$ heteroalkyl$C_{0-10}$alkylaminocarbonyl$C_{0-10}$ alkyl, $(C_{3-8})$heterocycloalkyl$C_{0-10}$ alkylaminocarbonyl$C_{0-10}$ alkyl, $(C_{3-8})$heteroaryl $C_{0-10}$ alkylaminocarbonyl$C_{0-10}$ alkyl, $C_{3-8}$ cycloalkyl $C_{0-10}$ alkylaminocarbonyl$C_{0-10}$ alkyl, aryl $C_{0-10}$ alkylaminocarbonyl$C_{0-10}$ alkyl, $(C_{3-8})$heterocycloalkyl$C_{0-10}$ alkylcarbonyl$C_{0-10}$ alkyl, $C_{1-10}$ alkyl(oxy)$_{0-1}C_{0-10}$ alkyl carbonylamino$C_{0-10}$ alkyl, $C_{1-10}$ alkenyl(oxy)$_{0-1}C_{0-10}$ alkyl carbonylamino$C_{0-10}$ alkyl, $C_{1-10}$ heteroalkyl(oxy)$_{0-1}$carbonylamino$C_{0-10}$ alkyl, $C_{3-8}$ cycloalkyl $C_{0-10}$ alkyl(oxy)$_{0-1}$carbonylamino$C_{0-10}$ alkyl, aryl $C_{0-10}$ alkyl(oxy)$_{0-1}$-carbonylamino$C_{0-10}$ alkyl, $(C_{3-8})$heteroaryl $C_{0-10}$ alkyl(oxy)$_{0-1}$carbonylamino$C_{0-10}$ alkyl, $(C_{3-8})$heterocycloalkyl $C_{0-10}$ alkyl (oxy)$_{0-1}$ carbonylamino$C_{0-10}$ alkyl, $C_{0-10}$ alkylureylenyl, $C_{1-4}$acylamino $C_{0-10}$ alkyl, $C_{0-10}$ alkylamino $C_{0-10}$ alkyl, aryl$C_{0-10}$ alkylamino $C_{0-10}$ alkyl, $C_{3-8}$ cycloalkyl $C_{0-10}$ alkylamino $C_{0-10}$ alkyl, $C_{3-8}$ heterocyclyl $C_{0-10}$ alkylamino $C_{0-10}$ alkyl, $C_{3-8}$ heterocycloalkyl $C_{0-10}$ alkylamino $C_{0-10}$ alkyl, $(C_{1-10}$ alkyl)$_2$aminocarbonyloxy, nitro, halo-aryl, halo-heterocyclyl, cyano-aryl, cyano-heteroaryl, cyano-heterocyclyl, and perfluoro $C_{1-6}$ alkoxy;

$R^6$ is independently selected from: hydrogen, (carbonyl)$_{0-1}$ $C_{1-10}$ alkyl, (carbonyl)$_{0-1}C_{2-10}$ alkenyl, (carbonyl)$_{0-1}$ $C_{2-10}$ alkynyl, $C_{0-10}$ alkyl(oxy)$_{0-1}$carbonyl$C_{0-10}$ alkyl, $C_{1-10}$ alkyl(oxy)$_{0-1}$carbonyl$C_{0-10}$ alkyl, $C_{2-10}$ alkenylcarbonyl, $C_{2-10}$ alkynylcarbonyl, $(C_{1-10})$alkyl(oxy)$_{0-1}$ $C_{0-10}$ alkyl, aryl(oxy)$_{0-1}C_{0-10}$ alkyl, $(C_{3-8})$heteroaryl (oxy)$_{0-1}C_{0-10}$ alkyl, $C_{3-8}$ cycloalkyl(oxy)$_{0-1}C_{0-10}$ alkyl, $(C_{3-8})$heterocycloalkyl(oxy)$_{0-1}C_{0-10}$ alkyl, $(C_{1-10})$heteroalkyl(oxy)$_{0-1}C_{0-10}$ alkyl, $C_{0-10}$ alkyl(oxy)$_{0-1}C_{0-10}$ alkylaminocarbonyl$C_{0-10}$ alkyl $C_{0-10}$ alkylaminocarbonyl$C_{1-10}$ heteroalkyl, $C_{0-10}$ alkylaminocarbonyl$(C_{3-8})$ heterocycloalkyl$C_{0-10}$ alkyl, $C_{0-10}$ alkylaminocarbonyl $(C_{3-8})$heteroaryl$C_{0-10}$ alkyl, $C_{0-10}$alkylaminocarbonyl $(C_{3-8})$cycloalkyl$C_{0-10}$ alkyl, $C_{0-10}$ alkylaminocarbonylaryl$C_{0-10}$ alkyl, hydroxy $C_{0-10}$alkyl, $C_{0-10}$ alkylsulfonyl, aryl $C_{1-10}$ alkylsulfonyl, $C_{3-8}$ heterocyclyl $C_{1-10}$ alkylsulfonyl, $C_{3-8}$ heterocycloalkyl $C_{1-10}$ alkylsulfonyl, $C_{3-8}$ cycloalkyl $C_{1-10}$ alkylsulfonyl, and $C_{1-6}$ haloalkyl;

wherein $R^1$, $R^2$, $R^5$ and $R^6$ are independently substituted with 0, 1, 2, or 3, substituents $R^3$ chosen from: halogen, $C_1$-$C_{10}$ alkyl, $CF_3$, $NH_2$, $N(C_1$-$C_6$ alkyl$)_2$, $NO_2$, —$(C_{0-6})$alkylCN, —OH, —O($C_1$-$C_6$ alkyl), $C_3$-$C_{10}$ cycloalkyl, $C_2$-$C_6$ alkenyl, $C_2$-$C_6$ alkynyl, $(C_0$-$C_6$ alkyl$)$ $S(O)_{0-2}$—, $(C_0$-$C_6$ alkyl$)S(O)_{0-2}$ $(C_0$-$C_6$ alkyl$)$-, $(C_0$-$C_6$ alkyl$)C(O)NH$—, $H_2N$—$C(NH)$—, —$O(C_1$-$C_6$ alkyl$)CF_3$, $(C_0$-$C_6$ alkyl$)C(O)$—, $(C_0$-$C_6$ alkyl$)$ $OC(O)$—, $(C_0$-$C_6$ alkyl$)O(C_1$-$C_6$ alkyl$)$-, $(C_0$-$C_6$ alkyl$)$ $C(O)_{1-2}(C_0$-$C_6$ alkyl$)$-, $(C_0$-$C_6$ alkyl$)OC(O)NH$—, —NH $(C_1$-$C_6$ alkyl$)NHC(O)NH(C_1$-$C_6$ alkyl$)$, $NHC(O)OC_1$-$C_6$ alkyl, —$NH(C_1$-$C_6$ alkyl$)NHSO_2(C_1$-$C_6$ alkyl$)$, —$(C_0$-$C_6$ alkyl$)NHSO_2(C_1$-$C_6$ alkyl$)$, $C_{1-10}$alkoxy, —$CO_2(C_{0-10}$ alkyl$)$, Oxo (=O), trifluoromethyl, trifluoroethyl, $C_{1-10}$ alkylsulfonyl, —$SO_2N(C_{1-6}$alkyl$)_{1-2}$, —$SO_2CF_3$, —$SO_2CF_2H$, —$C_{1-10}$ alkylsulfinyl, —$O_{(0-1)}(C_{1-10})$haloalkyl, aryl, heteroaryl, heterocyclyl, halo-aryl, halo-heterocyclyl, cyano-aryl, cyano-heteroaryl, and cyano-heterocyclyl.

In one embodiment of the compounds of formula I, L is

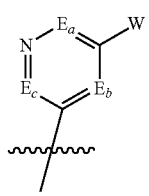

wherein $E_a$, $E_b$, and $E_c$, are each independently C or N provided that when $E_a$ and $E_c$ are each C then $E_b$ must be C.

In one embodiment of the compounds of formula I, L is

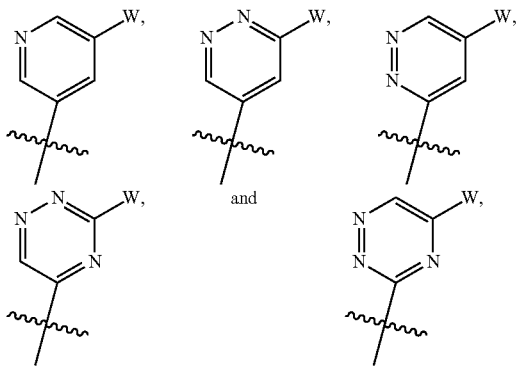

wherein L is substituted with 0, 1, 2, or 3 independently chosen $R^5$.

In another embodiment, L is

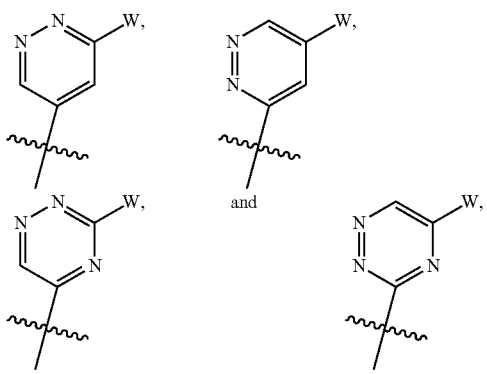

wherein L is substituted with 0, 1, 2, or 3 independently chosen $R^5$.

In a variant of this embodiment, L is

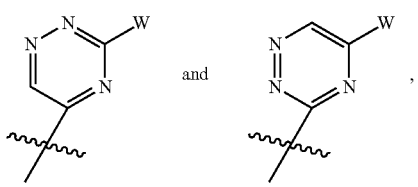

wherein L is substituted with 0, 1, 2, or 3 independently chosen $R^5$.

In another embodiment, L is

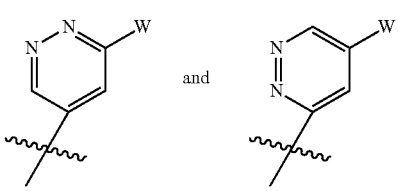

wherein L is substituted with 0, 1, 2, or 3 independently chosen $R^5$.

In yet another embodiment, L is chosen from:

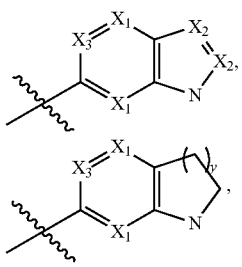

wherein $X_1$, $X_2$, and $X_3$ are each independently C or N, y is 0, 1, 2 or 3 and L is optionally substituted with 1, 2, or 3 independently chosen $R^5$.

In a variant of this embodiment, L is chosen from:

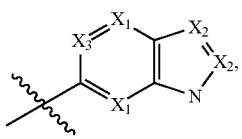

wherein $X_1$, $X_2$, and $X_3$ are each independently C or N and L is optionally substituted with 1, 2, or 3 independently chosen $R^5$.

In a variant of this embodiment, L is

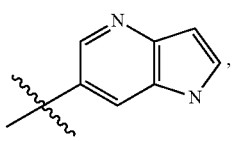

wherein L is optionally substituted with 1, 2, or 3 independently chosen $R^5$.

In another variant, L is chosen from:

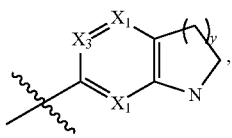

wherein $X_1$, $X_2$, and $X_3$ are each independently C or N, y is 0, 1, 2 or 3, and L is optionally substituted with 1, 2, or 3 independently chosen $R^5$.

In one embodiment, L is chosen from 1,3,5-triazin-2-yl, pyridin-3-yl, pyridazin-4-yl, pyridazin-3-yl, and 1,2,4-triazin-3-yl.

In one embodiment, L is selected from: 1H-indol-6-yl, 1H-benzo[d]imidazole, 1H-indazole, 1H-benzo[d][1,2,3]triazole, 1H-pyrrolo[2,3-b]pyridine-3-yl, 5H-pyrrolo[3,2-c]pyridazine, 7H-imidazo[4,5-c]pyridazine, 1H-pyrazolo[4,3-c]pyridazine, 1H-[1,2,3]triazolo[4,5-c]pyridazine, 1H-pyrrolo[3,2-b]pyridine, 1H-imidazo[4,5-b]pyridine, 1H-pyrazolo[4,3-b]pyridine, 1H-[1,2,3]triazolo[4,5-b]pyridine, 1H-3,6-pyrrolo[2,3-b]pyridine, 3H-imidazo[4,5-b]pyridine, 1H-pyrazolo[3,4-b]pyridine, 3H-[1,2,3]triazolo[4,5-b]pyridine, 5H-pyrrolo[2,3-b]pyrazine, 1H-imidazo[4,5-b]pyrazine, 1H-pyrazolo[3,4-b]pyrazine, and 1H-[1,2,3]triazolo[4,5-b]pyrazine. In another embodiment, L is selected from: 2,3,7-triazabicyclo[4.2.0]octa-1,3,5-trien-4-yl, 6,7-dihydro-5H-pyrrolo[3,2-c]pyradazine, 5,6,7,8-tetrahydropyrido[3,2-c]pyridazine, 6,7,8,9-tetrahydro-5H-pyridazino[4,3-b]azepine, 2,7-diazabicyclo[4.2.0]octa-1 (6),2,4-trien-4-yl, 1H-pyrrolo[2,3-b]pyridine-3-yl, 1,2,3,4-tetrahydro-1,5-naphthyridine, 6,7,8,9-tetrahydro-5H-pyrido[3,2-b]azepine, 2,8-diazabicyclo[4.2.0]octa-1,3,5-trien-3-yl, 1H-3,6-dihydropyrrolo[2,3-b]pyridine, 1,2,3,4-tetrahydro-1,8-naphthyridine, 6,7,8,9-tetrahydro-5H-pyrido[2,3-b]azepine, 2,5,7-triazabicyclo[4.2.0]octa-1(6),2,4-trien-4-yl; 6,7-dihydro-5H-pyrrolo[2,3-b]pyrazine, 5,6,7,8-tetrahydropyrido[2,3-b]pyrazine, 6,7,8,9-tetrahydro-5H-pyrazino[2,3-b]azepine, 7-azabicyclo[4.2.0]octa-1(6),2,4-trien-4-yl, indolin-6-yl, 1,2,3,4-tetrahydroquinoline, and 2,3,4,5-tetrahydro-1Hbenzo[b]azepine.

In one embodiment, W is chosen from $C_{1-10}$ alkylamino, a $(C_{1-10})$heteroalkyl containing 1, 2, or 3 atoms independently selected from N, O or S, and a 3-15 member saturated, unsaturated or partially saturated monocyclic or bicyclic ring system containing 0, 1, 2, 3, or 4 atoms independently selected from N, O, or S, wherein W is substituted with 0, 1, 2 or 3 independently chosen $R^5$.

In another embodiment, W is —$NR^6R^6$ wherein two $R^6$ and the nitrogen to which they are attached can optionally form a -4, -5, or -6 member saturated ring system, and wherein W is substituted with 0, 1, 2 or 3 independently chosen $R^5$.

In one embodiment, $R^1$, $R^2$ and $R^5$ are independently chosen from: hydrogen, halogen, amino, cyano, hydroxy, hydroxy$C_{0-10}$alkyl, $C_{1-6}$ haloalkyl, $C_{1-10}$ alkylsulfonyl, $(C_{0-10}$ alkyl)sulfonylamino, $C_{1-10}$ alkyl $(oxy)_{0-1}C_{0-10}$ alkyl, $C_{2-10}$alkenyl$(oxy)_{0-1}C_{0-10}$ alkyl, aryl$C_{0-10}$ alkyl$(oxy)_{0-1}C_{0-10}$ alkyl, $(C_{3-8})$heteroaryl$C_{0-10}$ alkyl$(oxy)_{0-1}C_{0-10}$ alkyl, $C_{3-8}$ cycloalkyl$C_{0-10}$ alkyl$(oxy)_{0-1}C_{0-10}$ alkyl, $(C_{3-8})$heterocycloalkyl$C_{0-10}$ alkyl$(oxy)_{0-1}C_{0-10}$ alkyl, $C_{0-10}$ alkyl $(oxy)_{0-1}C_{1-10}$ alkyloxy$C_{0-10}$ alkyl, $C_{0-10}$ alkyl$(oxy)_{0-1}C_{0-10}$ alkylaminocarbonyl$C_{0-10}$ alkyl, $(C_{0-10}$ alkyl$)_{1-2}$-amino$C_{1-10}$ alkyloxy$C_{0-10}$ alkyl, $(C_{0-10}$ alkyl$)_{1-2}$-aminocarbonyl$C_{0-10}$ alkyl, $(C_{3-8})$heterocycloalkyl$C_{0-10}$ alkylaminocarbonyl$C_{0-10}$ alkyl, $(C_{3-8})$heteroaryl $C_{0-10}$ alkylaminocarbonyl$C_{0-10}$ alkyl, $C_{3-8}$ cycloalkyl $C_{0-10}$ alkylaminocarbonyl$C_{0-10}$ alkyl, $C_{1-10}$ alkyl $(oxy)_{0-1}C_{0-10}$ alkyl carbonylamino$C_{0-10}$ alkyl, $C_{1-10}$ alkenyl $(oxy)_{0-1}C_{0-10}$ alkyl carbonylamino$C_{0-10}$ alkyl, $C_{3-8}$ cycloalkyl $C_{0-10}$ alkyl $(oxy)_{0-1}$carbonylamino$C_{0-10}$ alkyl, $(C_{3-8})$heteroaryl $C_{0-10}$ alkyl$(oxy)_{0-1}$carbonylamino$C_{0-10}$ alkyl, and $C_{0-10}$ alkylureylenyl, wherein $R^1$, $R^2$ and $R^5$ are independently substituted with 0, 1, 2, or 3 substituents $R^3$.

In one embodiment, $R^1$, $R^2$ and $R^5$ are independently chosen from (1-methylethyl)carbamoyl, (2-methoxyethyl)carbamoyl, (2-hydroxy-ethyl)carbamoyl, (tetrahydro-2H-pyran-4-yl)carbamoyl, azetidin-1-ylcarbonyl, 2-methylpropylcarbamoyl, carbamoyl, (tetrahydrothiophen-3-yl)carbamoyl, (1H-pyrazol-5-ylmethyl)carbamoyl, (4-hydroxypiperidin-1-yl)carbonyl, cyclopropylmethylcarbamoyl, sulfamoyl, dimethylsulfamoyl, amino, acetylamino, sulfonylamino, propanoylamino, (propan-2-ylcarbamoyl) amino, (propylcarbamoyl)amino, carbamoylamino, methylcarbamate, ethylcarbamate, (1-methyethyl)carbamate, 1H-pyrazolyl, tertbutoxymethyl, (methoxyethyl)piperazinyl, 2-morpholin-4-ylethoxy)methyl, (prop-2-en-1-yloxy)methyl, piperidinylmethoxy, pyrrolidin-1-ylmethyl, methoxymethyl, cyclopentanylcarboxamidomethyl, propanoylamino) methyl, (cyclohexanecarbonylamino)methyl, but-2-enoylaminomethyl, (cyclopropylcarbonyl)aminomethyl, (1,3-oxazol-5-yl)carbonylaminomethyl, (butanoylamino)methyl, (pyrrolidin-1-ylcarbonyl)aminomethyl, halogen, cyano, carbamoyl, methoxy, trifluoroethyl, methylsulfonyl, hydroxyl, 2-methoxyethoxy, methylethoxy, benzyloxy, cyclopentyloxy, cyclopropylmethoxy, 2-phenylethoxy, 2,3-dihydro-1H-inden-2-yloxy, tetrahydro-2H-pyran-4-yloxy, 2-oxopyrrolidin-1-yl)ethoxy, pyridin-3-ylmethoxy, 2-pyridin-2-ylethoxy, 2-(dimethylamino)ethoxy, 3-(dimethylamino)propoxy, 2-morpholin-4-ylethoxy, 1-methylpiperidin-4-yl)oxy, 2-(piperazin-1-yl)ethoxy, and piperidin-4-yl) methoxy, wherein $R^1$, $R^2$ and $R^5$ are independently substituted with 0, 1, 2, or 3 substituents $R^3$.

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR^8R^9)_2$—, each occurrence of the two $R^8$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of formula I may be separated into their individual diastereoisomers by, e.g., fractional crystallization from suitable solvents, e.g., methylene chloride/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of this invention may be obtained by stereospecific synthesis using optically pure starting materials or reagents of known absolute configuration.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the general formula I may be obtained by stereospecific synthesis using optically pure starting materials, intermediates or reagents of known configuration. Absolute stereochemistry may be determined by X-ray crystallography of crystalline products or crystalline intermediates which are derivatized, if necessary, with a reagent containing a stereogenic center of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2 or JAK3. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a JAK-mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug.

These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

SCHEMES AND EXAMPLES

The abbreviations used herein have the following tabulated meanings. Abbreviations not tabulated below have their meanings as commonly used unless specifically stated otherwise.

| Abbreviation | Meaning |
|---|---|
| ACN | Acetonitrile |
| MeCN | Acetonitrile |
| BAST | bis(2-methoxyethyl)aminosulfur trifluoride |
| Chiral SFC | chiral super critical fluid chromatography |
| CO$_2$ | carbon dioxide |
| Cs$_2$CO$_3$ | cesium carbonate |
| DBU | 1,8-diazabicyclo[5.4.0]undec-7-ene |
| DCE | 1,2-dichloroethane |
| DCM | Dichloromethane |
| DIPEA | N,N-diisopropylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| mCPBA | meta-chloroperoxybenzoic acid |
| LRMS | low resolution mass spectrometry |
| MeI | Iodomethane |
| Me—THF | 2-methyltetrahydrofuran |
| MgSO4 | magnesium sulfate |
| MP—(OAc)$_3$BH | solid supported (macro porous) triacetoxyborohydride |
| MPLC | medium pressure liquid chromatography |
| NaH | sodium hydride |
| Na$_2$SO$_4$ | sodium sulfate |
| NaBH4 | sodium borohydride |
| NaHCO$_3$ | sodium bicarbonate |
| NaOMe | sodium methoxide |
| Pd$_2$(dba)$_3$ | tris(dibenzylideneacetone)dipalladium(0) |
| POCl$_3$ | phosphorus (V) oxychloride |
| PyBOP | (7-azabenzotriazol-1-yloxy)tripyrrolidinophosphonium hexafluorophosphate |
| SEM—Cl | 2-(trimethylsilyl)ethoxymethyl chloride |
| SiliaCat ® DPP-Pd | silica bound diphenylphosphine palladium (II) |
| TBAF | tetra-n-butylammonium fluoride |
| TBS—Cl | tert-butyldimethylsilyl chloride |
| t-BuOH | tert-butanol |
| TEA | Triethylamine |
| TFA | trifluoroacetic acid |
| THF | Tetrahydrofuran |
| X—Phos | 2-dicyclohexylphosphino-2',4',6'-triisopropylbiphenyl |
| $^t$Bu—X—Phos | di-tert-butyl[3,4,5,6-tetramethyl-2',4',6'-tri(propan-2-yl)biphenyl-2-yl]phosphane |
| NMO | 4-methylmorpholine N-oxide |
| TPAP | tetra-n-propylammonium perruthenate (VII) |
| HCOOH | formic acid |
| K$^t$OBu | potassium tert-butoxide |
| Na$_2$S$_2$O$_5$ | sodium metabisulfite |
| NMR | nuclear magnetic reasonance |
| TLC | thin layer chromatography |
| (EtO)$_2$P(O)CH$_2$CN | diethyl (cyanomethyl)phosphonate |
| MsCl | methanesulfonyl chloride |
| TsOH | p-toluenesulfonic acid |
| KCN | potassium cyanide |
| PS | Polystryene |
| TMS | Trimethylsilane |
| CA | Commercially Available |
| BINAP | (R)-(+)-2,2'-BIS(DIPHENYLPHOSPHINO)-1,1'-BINAPHTHYL |
| MeOH | Methanol |
| NH4Cl | Ammomium chloride |
| MTBE | Methyl t-butyl ether |
| KOH | Potassium hydroxide |
| KHSO4 | Potassium hydrogen sulfate |
| NaOH | Sodium hydroxide |
| DME | Dimethoxyethane |
| THF | Tetrahydrofuran |
| Tetrakis | TETRAKIS(TRIPHENYLPHOSPHINE)PALLADIUM(0) |

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention hereinabove.

Those skilled in the art will readily understand that known variations of the conditions and processes of the following preparative procedures can be used to prepare these compounds. The invention will now be illustrated in the following non-limiting Examples in which, unless otherwise stated: all reactions were stirred (mechanically, stir bar/stir plate, or shaken) and conducted under an inert atmosphere of nitrogen or argon unless specifically stated otherwise. All temperatures are degrees Celsius unless otherwise noted. Ambient temperature is 15-25° C.

Most compounds were purified by reverse-phase preparative HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only. All end products were analyzed by NMR and LCMS. Intermediates were analyzed by NMR and/or TLC and/or LCMS.

General Scheme 1:

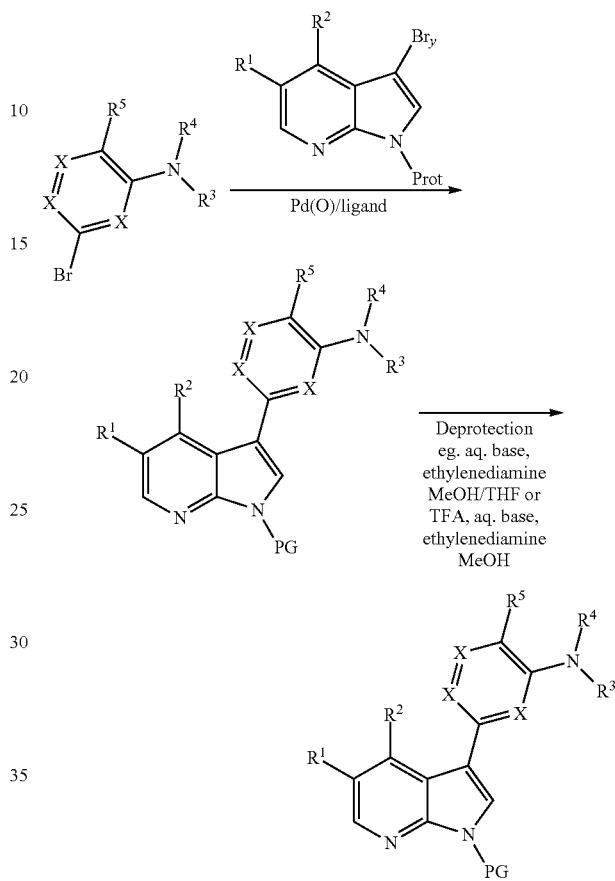

General Scheme 2:

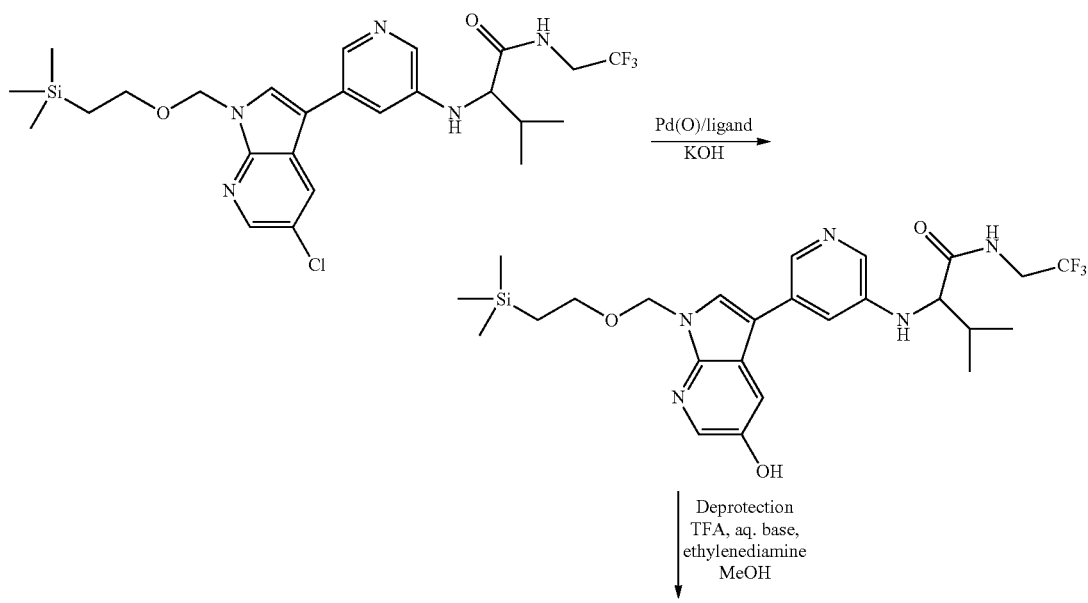

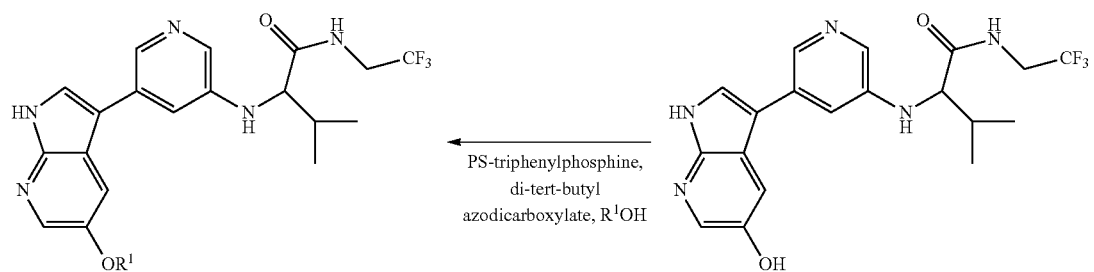
General Scheme 3:
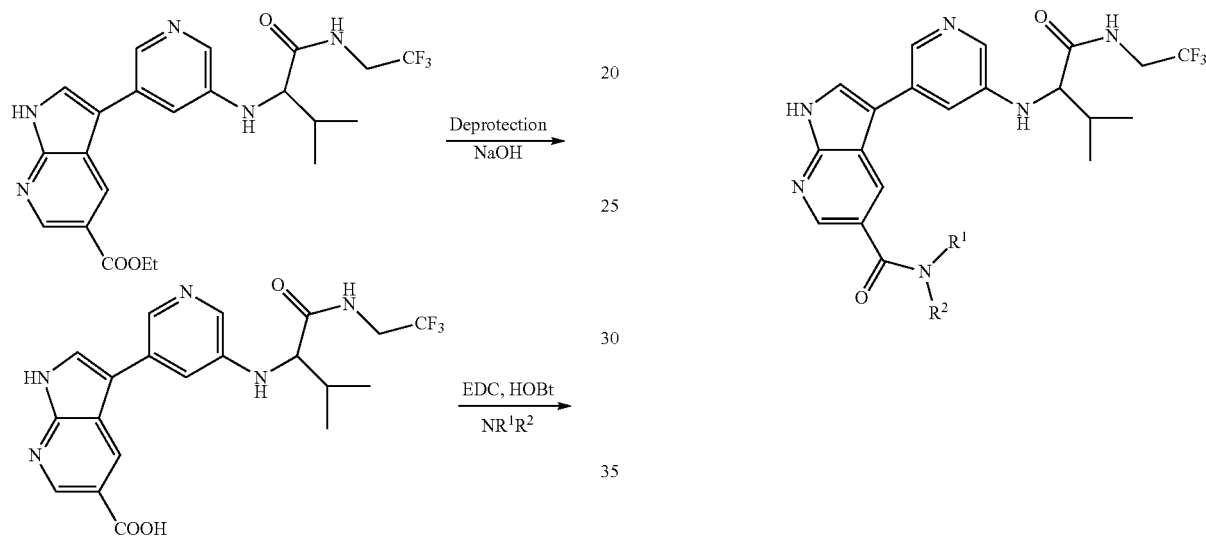
General Scheme 4:
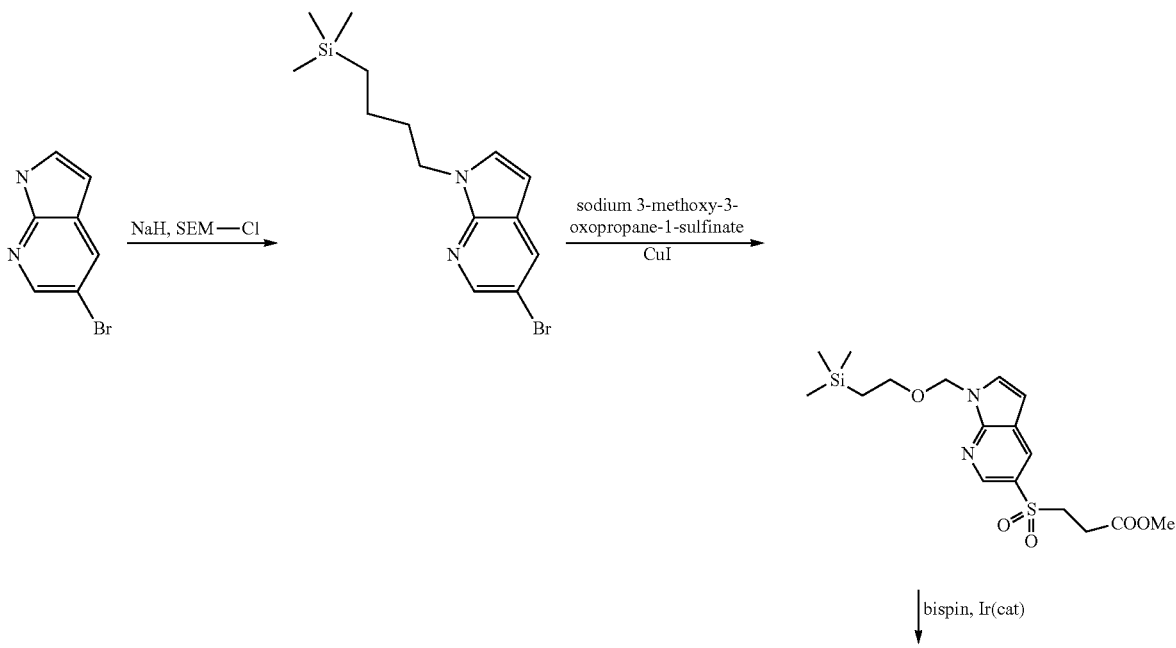

33 34
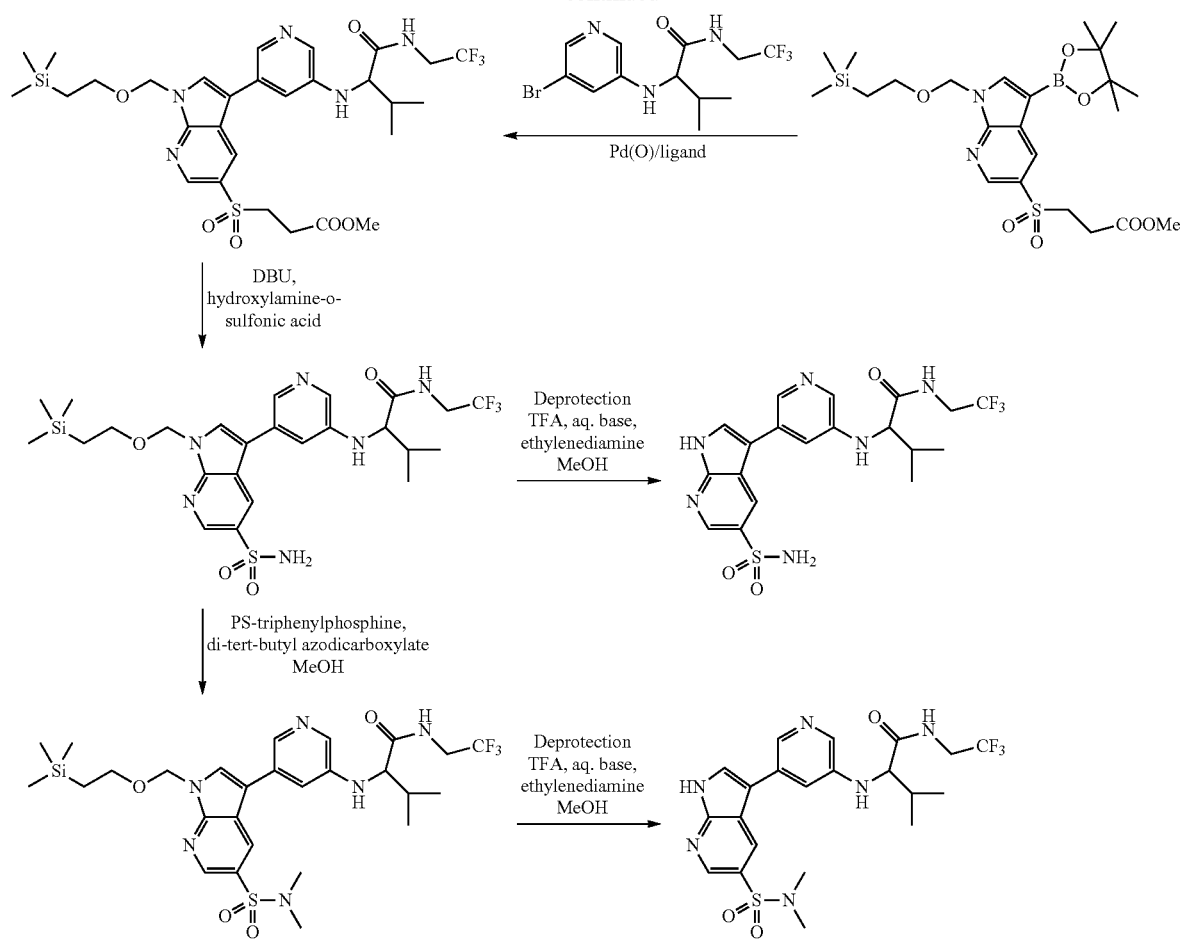
General Scheme 5:
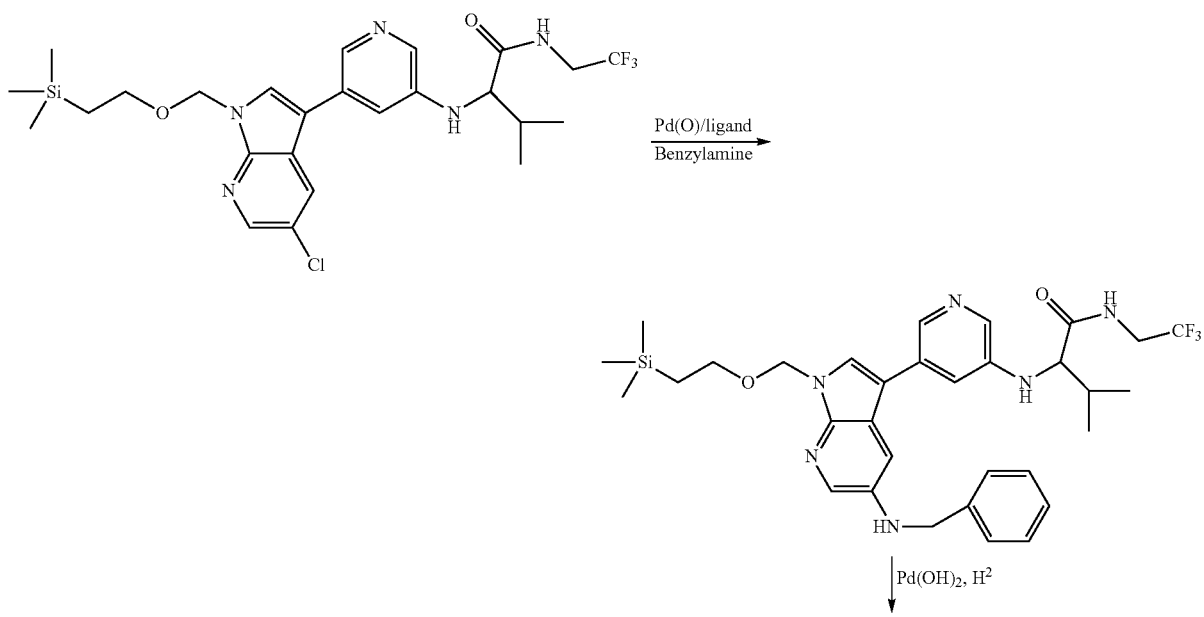

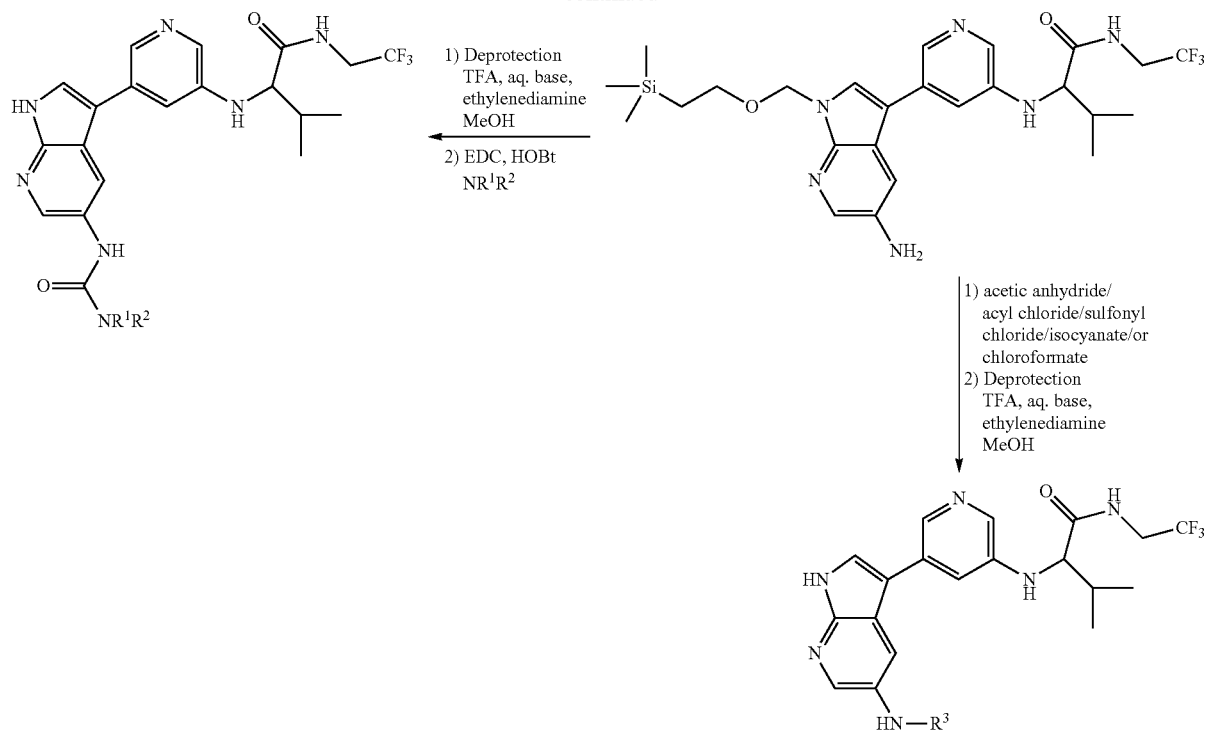
General Scheme 6:
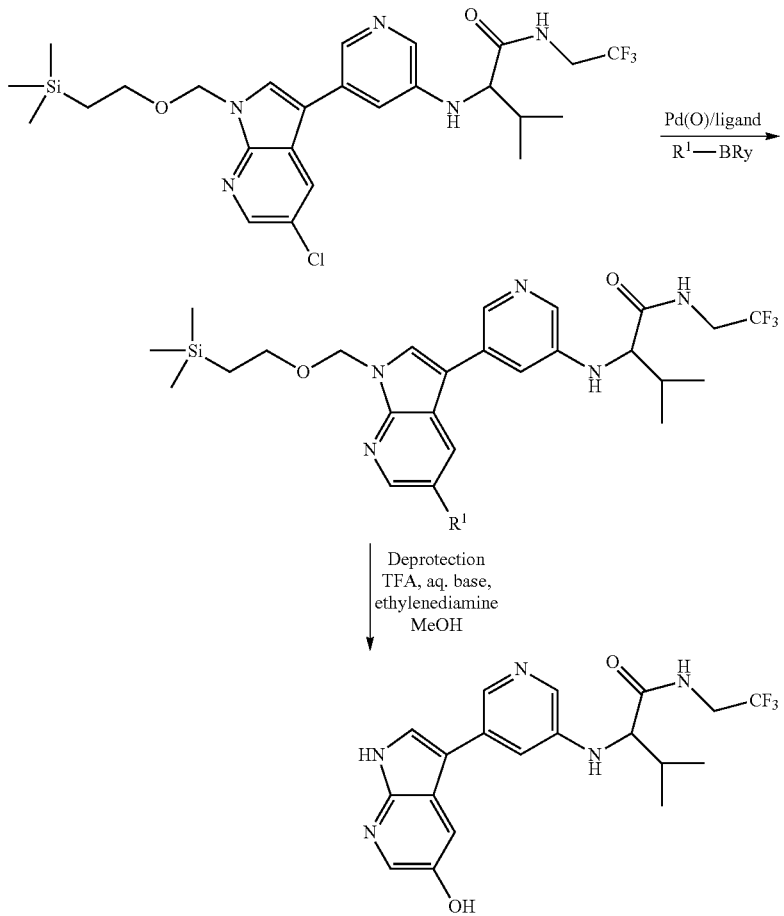

General Scheme 7:
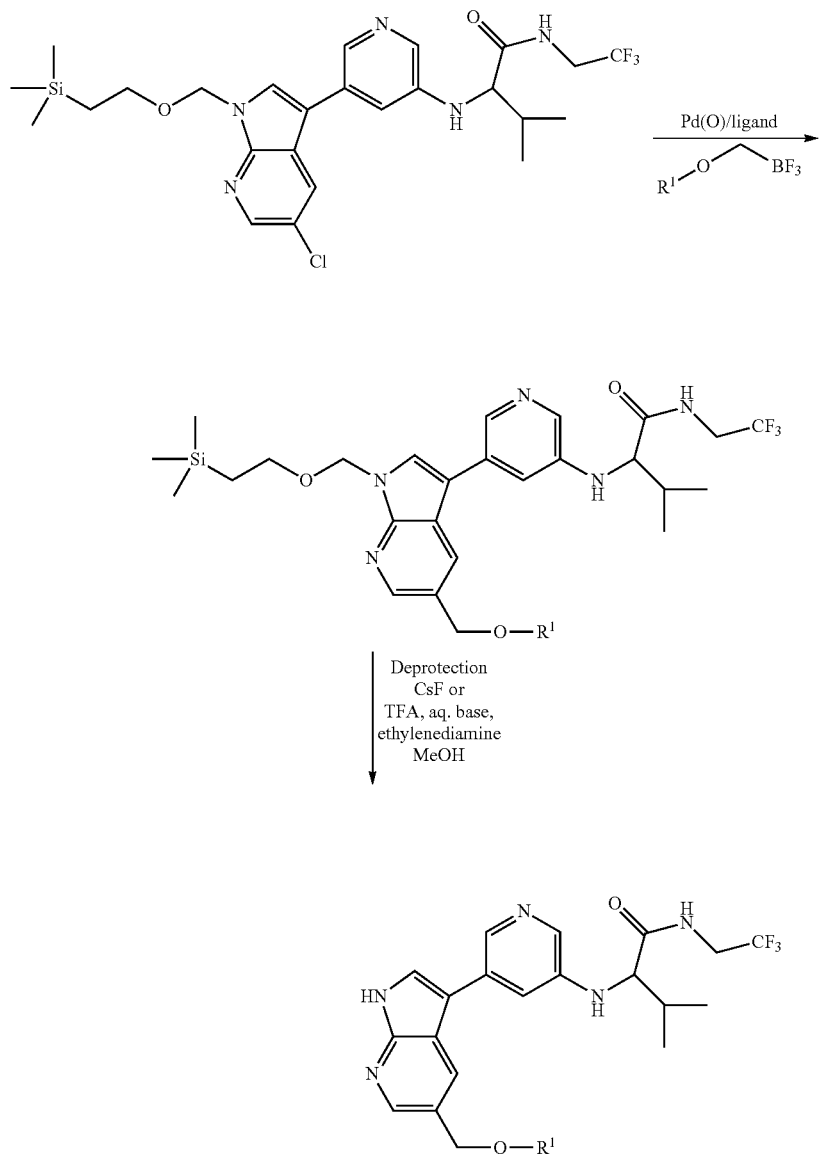
General Scheme 8:
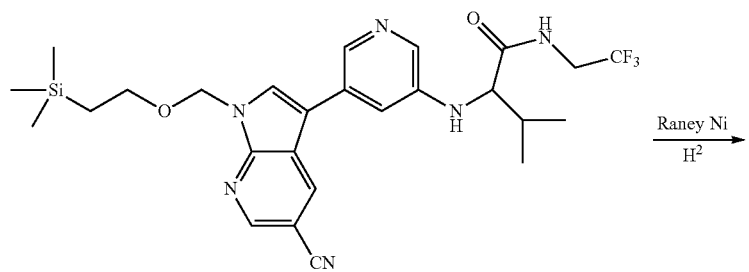

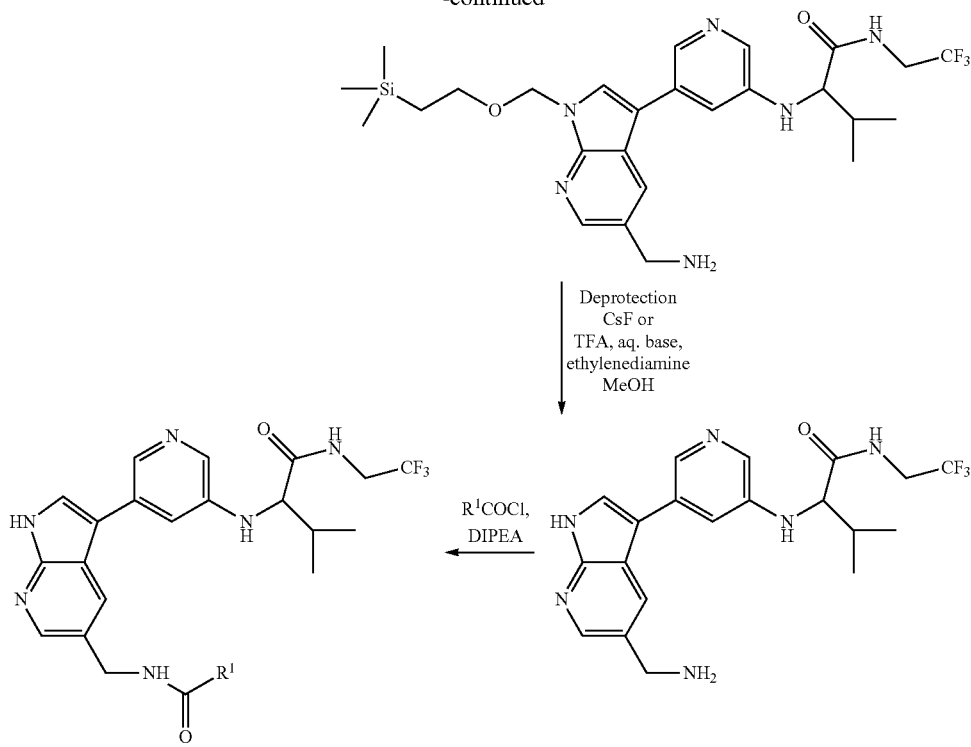

Pyridine Series Intermediates (R)-2-(5-bromopyridin-3-ylamino)-N-(2,2,2-trifluoroethyl)propanamide (I-1)

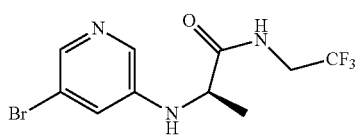

In a microwave vial equipped with a magnetic stirrer, 3,5-Dibromopyridine (Aldrich Chemical) (1 g, 4.22 mmol), (R)-2-amino-N-(2,2,2-trifluoroethyl)propanamide hydrochloride (0.872 g, 4.22 mmol), Potassium carbonate (2.334 g, 16.89 mmol) were added followed by DMSO (6.03 ml, 0.7M). The reaction mixture was stirred and purged under nitrogen for 10 minutes, then Copper (I) Iodide (0.08 g, 0.422 mmol) was added and the reaction mixture was heated in an oil bath at 120° C. for 2 hours. The cooled reaction mixture was then partitioned between Isopropanol (IPA): Chloroform (1:3) and Water, the aqueous layer was extracted with twice with IPA: Chloroform mixture. The combined organic layers were extracted with water, dried over anhydrous magnesium sulfate, filtered and concentrated to give the crude sample. Purification on silica (100 g SNAP Biotage column) using 0-5% Methanol/Dichloromethane gave (R)-2-(5-bromopyridin-3-ylamino)-N-(2,2,2-trifluoroethyl)propanamide, I-1, (1.03 g, 74.8% yield) LRMS (ESI) m/z 325.9 [(M+H)$^+$; calcd for $C_{10}H_{11}BrF_3N_3O$: 326.01]

Intermediate 1-2

2-[(5-bromopyridin-3-yl)amino]-3-methyl-N-(2,2,2-trifluoroethyl)butanamide (I-2)

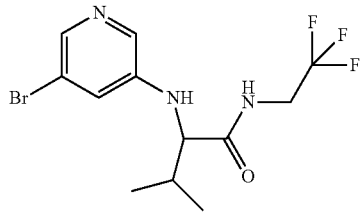

Step 1: tert-butyl 2-[(5-bromopyridin-3-yl)amino]-3-methylbutanoate (I-2a)

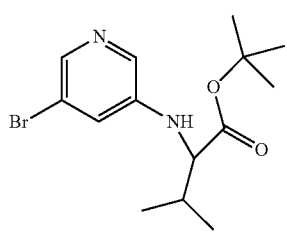

To a nitrogen degassed mixture of 3,5-dibromopyridine (5.0 g, 21.11 mmol), D-Valine t-butylester HCl (Aldrich Chemical, 4.43 g, 21.11 mmol) and sodium tert-butoxide (6.09 g, 63.3 mmol), in Toluene (200 ml) was added BINAP (2.63 g, 4.22 mmol) followed by tris(dibenzylideneacetone)-dipalladium(0) (Strem Chemical, 1.933 g, 2.111 mmol). The reaction was sealed and heated at 90° C. for 1 hr. The reaction was cooled, quenched into brine (100 mL), aqueous KHSO$_4$ (20 mL) and ethyl acetate (200 mL). Aqueous sodium bicarbonate was added to adjust the pH to 8.0 and the organic layer removed. The aqueous layer was washed with ethyl acetate (100 mL). The combined organic extracts were washed with brine (100 mL), dried over sodium sulfate, filtered thru a pad of silica and the filtrate concentrated to oil. The oil was chromatographed on silica eluting with 5-30% ethyl acetate/hex to give 4.8 gm of compound I-2a, 69%.

LRMS (ESI) m/z 329.1 [(M+H)$^+$; calcd for C$_{14}$H$_{21}$BrN$_2$O$_2$: 329.1].

Step 2 2-[(5-bromopyridin-3-yl)amino]-3-methylbutanoic acid dihydrochloride (I-2b)

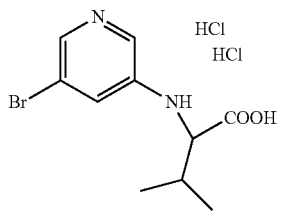

To a solution of I-2a (1.46 g, 4.43 mmol) in dichloromethane (20 ml) was added TFA (20 ml) and the mixture allowed to stir at RT for 6 hr. The reaction was concentrated to give a dark oil. The oil was azeotroped with dichloroethane (100 mL) and the resulting oil dissolved in diethyl ether (100 mL). The solution was treated with 1N HCL/ether (13.3 mL, 5 eq.) to give a light yellow solid. The mixture was concentrated to give a solid. The solid was slurried in diethyl ether (100 mL), sonicated and then filtered under nitrogen to give 1.42 gm, of I-2b, (93%). LRMS (ESI) m/z 273.0 [(M+H)$^+$; calcd for C10H13BrN2O2: 273.0].

Step 3 2-[(5-bromopyridin-3-yl)amino]-3-methyl-N-(2,2,2-trifluoroethyl)butanamide (I-2)

To a mixture of I-2b (3.0 g, 8.67 mmol), 2,2,2-trifluoroethylamine (CA) (1.022 mL, 13.00 mmol), HOBT (1.991 g, 13.00 mmol) and DIPEA (6.06 mL, 34.7 mmol) in DMF (20 mL) was added EDC (2.493 g, 13.00 mmol). The reaction was stirred at RT for 2 hrs and quenched into aqueous KHSO$_4$ (100 mL) and ethyl acetate (100 mL). The pH of the mixture was adjusted to 5.2 with additional aqueous KHSO$_4$. The organic layer was removed, washed with aqueous sodium bicarbonate ((100 mL) followed by brine (50 mL). The aqueous extracts were washed with ethyl acetate (50 mL) and combined organics dried over sodium sulfate, filtered and concentrated to an oil. The oil was chromatographed on silica (100 gm) using 25-80% ethyl acetate/hexanes to give the desired product as an off white solid (3.0 g). The solid was slurried in diethyl ether (50 ml), sonicated and diluted with hexanes (100 mL). Filtration under nitrogen gave 2.9 g, 98% white solid, I-2.

LRMS (ESI) m/z 354.1 [(M+H)$^+$; calcd for C$_{12}$H$_{15}$BrF$_3$N$_3$O: 354.0].

Intermediate I-3

(R)-2-(5-bromopyridin-3-ylamino)-3-methyl-N-(2,2,2-trifluoroethyl)butanamide (I-3)

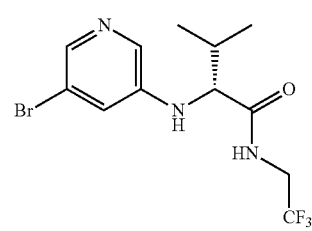

Step 1 (R)-tert-butyl 3-methyl-1-oxo-1-(2,2,2-trifluoroethylamino)butan-2-ylcarbamate (I-3a)

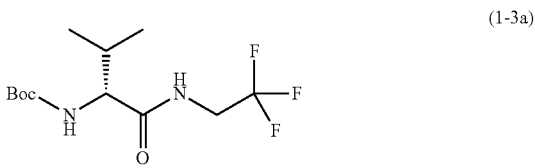 [SMILES: CC(C)[C@@H](NC(=O)OC(C)(C)C)C(=O)NCC(F)(F)F]

A mixture of (R)-2-(tert-butoxycarbonylamino)-3-methylbutanoic acid (Aldrich, 10.0 g, 46.0 mmole), 2,2,2 trifluoroethyl amine hydrochloride (Aldrich Chemical) (7.48 g, 55.2 mmole), EDC (10.6 g, 55.2 mmole), HOBT (9.16 g, 60.0 mmole) and DIPEA (24.1 mL, 138 mmole) in dichloromethane (200 mL) was allowed to stir overnite at room temperature. The mixture was diluted with ethyl acetate (200 mL) washed with 1N HCl, (50 mL) followed by aq. sodium bicarbonate (200 mL) and then brine (100 mL). The organic was dried over sodium sulfate, filtered and concentrated in vacuo to give 12.81 g of solid.

LRMS (ESI) m/z 299.4 [(M+H)$^+$; calcd for C$_{12}$H$_{21}$F$_3$N$_2$O$_3$: 299.3]

Step 2 (R)-2-amino-3-methyl-N-(2,2,2-trifluoroethyl)butanamide hydrochloride (I-3b)

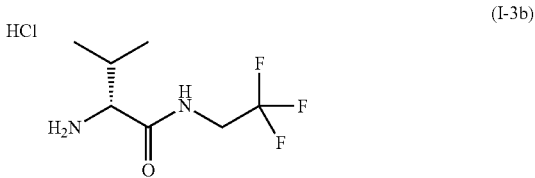

(R)-tert-butyl 3-methyl-1-oxo-1-(2,2,2-trifluoroethylamino)butan-2-ylcarbamate I-3a (12.81 g, 42.9 mmol) was dissolved in DCM (30 ml), and TFA (12 ml, 156 mmol) slowly added. The reaction was allowed to stir at room temperature for 2 hr. The mixture was concentrated in vacuo to an oil. The oil was dissolved in DCM and washed with aq. sodium bicarbonate (50 mL) dried over sodium sulfate, filtered and concentrated to an oil. The oil was dissolved in ethyl acetate, cooled to 0° C. and treated with 1N HCL in diethyl ethere to give upon filtration 10.0 gm solid.

LRMS (ESI) m/z 199.2 [(M+H)$^+$; calcd for C$_7$H$_{14}$F$_3$N$_2$O$_3$: 199.2]

Step 3 (R)-2-(5-bromopyridin-3-ylamino)-3-methyl-N-(2,2,2-trifluoroethyl)butanamide (I-3)

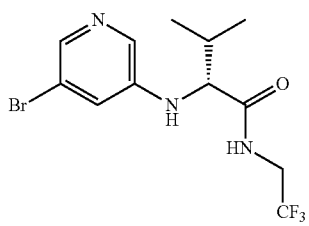

In a round bottomed flask equipped with a magnetic stirrer, (R)-2-amino-3-methyl-N-(2,2,2-trifluoroethyl)butanamide hydrochloride (1-3b) (20 g, 85 mmol), 3,5-Dibromopyridine (30.3 g, 128 mmol), Potassium carbonate (35.3 g, 256 mmol) were suspended in DMSO (71 ml, 1.2M) and reaction mixture was purged with nitrogen for 20 minutes, then Copper(I) Iodide (0.974 g, 5.1 mmol) was added and the reaction mixture was slowly heated to 120° C. overnight. The cooled reaction mixture was then partitioned between Isopropanol (IPA):Chloroform (1:3) and Water, the aqueous layer was extracted with three times with IPA:Chloroform mixture. The combined organic layers were extracted with 1M solution of EDTA disodium salt, dried over anhydrous magnesium sulfate, filtered and concentrated to give the crude sample. Purification on a silica gel column using a gradient 0-40% ethyl acetate:hexane gave an orange solid which was taken up in ethyl acetate and concentrated to an oil, hexane was added dropwise while stirring, a white solid crystallized which was filtered, washed with hexane and dried under vacuum to give 14 g, (46.4%) the title compound, I-3, as a white solid.

LRMS (ESI) m/z 356.1 [(M+H)$^+$; calcd for $C_{12}H_{15}BrF_3N_3O$: 354.05]

Intermediate I-4

2-[(5-bromopyridin-3-yl)amino]-2-methyl-N-(2,2,2-trifluoroethyl)propanamide (I-4)

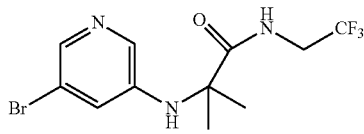

Step 1 2-[(5-bromopyridin-3-yl)amino]-2-methylpropanenitrile (I-4a)

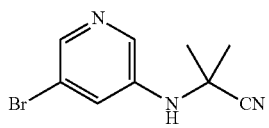

3-Amino-5-bromopyridine (Aldrich, 5.0 g, 28.9 mmol), acetone (6.37 ml, 87 mmol), Zinc chloride (0.5 M in THF) (11.56 ml, 5.78 mmol) were combined in acetonitrile (150 ml) and cooled to 0° C. The reaction was stirred for 10 min and trimethylsilylcyanide (10.46 ml, 78 mmol) was added dropwise. The reaction was heated to 85° C. in an oil bath with a reflux condensor. The reaction was monitored by LCMS and at 2 hrs the reaction was 80% complete. The reaction was cooled to room temperature and additional acetone (1.2 mL) and trimethylsilylcyanide (3 mL) added. The reaction was allowed to stir 18 hrs at 85° C. The reaction mixture was concentrated to reduce the volume by 50% and mixture poured into brine (100 mL). The pH was adjusted to 7.5 with aq. NaHCO$_3$ and the product extracted with ethyl acetate (2×100 mL). The combined organic extracts were washed with brine, dried over Na$_2$SO$_4$, and resulting solution filtered thru a pad of silica. The filtrate was concentrated and the residue purified by silica gel chromatography, Biotage SNAP 100 g, eluting with EtOAc/isohexane (0-100%) to give 6.42 g, 93% yield of the desired product as an off-white solid, I-4a.

LRMS (ESI) m/z 240.0 [(M+H)$^+$; calcd for $C_9H_{10}BrN_3$: 240.0].

Step 2 2-[(5-bromopyridin-3-yl)amino]-2-methylpropanoic acid (I-4b)

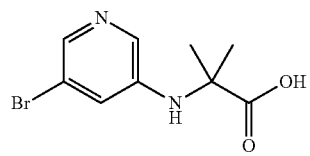

2-[(5-bromopyridin-3-yl)amino]-2-methylpropanenitrile I-4a (4.0 g, 16.66 mmol) was treated with 12 M HCl (120 ml, 1440 mmol) and resulting mixture heated to 100° C. overnight in sealed tube. LCMS indicates desired product with no other intermediates seen. Reaction mixture was concentrated in vacuo to give a yellow foam/solid. The solid was dissolved in water (50 ml) and pH adjusted to 6.5 with 4N NaOH. Solids precipitated from the mixture. The mixture was cooled to 0° C., aged 30 minutes and solids filtered, washed with water (10 mL) and sucked dry to give 2.75 g of an off white solid, I-4b. Filtrate pH adjusted to 5.2 with aq. KHSO$_4$ and an additional crop filtered to give another 0.65 g. Total 3.4 gm, 85%.

LRMS (ESI) m/z 259.0 [(M+H)$^+$; calcd for $C_9H_{11}BrN_2O_2$: 259.0].

Step 3 2-[(5-bromopyridin-3-yl)amino]-2-methyl-N-(2,2,2-trifluoroethyl)propanamide (I-4)

To a mixture of 2-[(5-bromopyridin-3-yl)amino]-2-methylpropanoic acid I-4b (2.0 g, 7.72 mmol), 2,2,2-trifluoroethylamine (1.214 mL, 15.44 mmol), HOBT (1.773 g, 11.58 mmol) and DIPEA (2.70 mL, 15.44 mmol) in DMF (20 mL) was added EDC (2.220 g, 11.58 mmol). The mixture was allowed to stir at RT for 18 hr. The reaction was quenched into water (100 mL) and ethyl acetate (100 mL) and aq. KHSO$_4$ added to adjust the pH to 6.5. Organic layer removed, washed with aqueous NaHCO$_3$ (50 mL) and then brine (50 mL). The aqueous extracts were washed with ethyl acetate (50 mL). Organics combined, dried over sodium sulfate, filtered thru a pad of silica and concentrated to give a solid 2.9 gms. Solid slurried in ether, sonicated and filtered to give 2.4 g, (91%) title compound, I-4, as a white solid.

LRMS (ESI) m/z 339.8 [(M+H)$^+$; calcd for $C_{11}H_{13}BrF_3N_3O$: 340.0].

Intermediate I-5

(Cis)-2-[(5-bromopyridin-3-yl)amino]-N-(2,2,2-trifluoroethyl)cyclohexanecarboxamide (I-5)

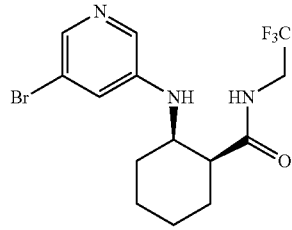

I-5

Step 1 tert-butyl{(cis)-2-[(2,2,2-trifluoroethyl)carbamoyl]cyclohexyl}carbamate (I-5a)

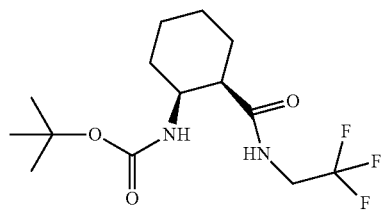

I-5a

To a mixture of cis-2-tertbutoxycarbonylamino-cyclohexanecarboxylic acid (Acros, 2 g, 8.22 mmol), 2,2,2-trifluoroethylamine (0.969 mL, 12.33 mmol), HOBT (1.888 g, 12.33 mmol) and DIPEA (4.31 mL, 24.66 mmol) in DMF (10 mL) was added EDC (2.364 g, 12.33 mmol) and the mixture allowed to stir at RT for 1 hr. The reaction was quenched into 10% aq. KHSO$_4$ (100 mL) and product extracted with ethyl acetate (100 mL). Organic washed with aq. NaHCO$_3$ (50 mL) and then brine (50 mL). Aqueous extracts backwashed with ethyl acetate (50 mL) and organic extracts combined, dried over sodium sulfate, filtered and concentrated to give 2.55 gm of a white solid, I-5a. $^1$H NMR (600 MHz, CDCl3) δ 6.18 (m, 1H), 5.07 (m, 1H), 3.75-4.0 (m 3H), 2.62 (m, 1H), 1.3-2.0 (br m, 8H), 1.40 (s, 9H).

Step 2 (cis)-2-amino-N-(2,2,2-trifluoroethyl)cyclohexanecarboxamide Hydrochloride (I-5b)

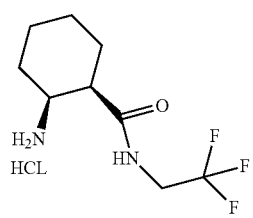

I-5b

To tert-butyl {(cis)-2-[(2,2,2-trifluoroethyl)carbamoyl]cyclohexyl}carbamate, I-5a (2.55 g, 7.86 mmol) in Dioxane (10 ml) was added 4 M HCl/Dioxane (19.66 ml, 79 mmol) and the mixture allowed to stir at RT for 60 min. The reaction was concentrated in vacuo and resulting solid slurried with diethyl ether (100 mL). Re-concentration of the mixture and re-slurry of the solid with ether/hexane gave a free flowing solid. Final concentration of the mixture gave a white solid, I-5b, (2.1 gm) which was stored under nitrogen.

LRMS (ESI) m/z 225.2 [(M+H)$^+$; calcd for C$_9$H$_{15}$F$_3$N$_2$O: 225.1].

Step 3 (Cis)-2-[(5-bromopyridin-3-yl)amino]-N-(2,2,2-trifluoroethyl)cyclohexane carboxamide (I-5)

To a nitrogen degassed mixture of 3,5-dibromopyridine (8.5 g, 35.9 mmol), (cis)-2-amino-N-(2,2,2-trifluoroethyl)cyclohexanecarboxamide hydrochloride, I-5b, (9.35 g, 35.9 mmol), potassium carbonate (19.84 g, 144 mmol) and L-proline (0.826 g, 7.18 mmol), in DMSO (70 ml) was added copper(i) iodide (Strem® crushed) (0.683 g, 3.59 mmol). The reaction was sealed and heated at 80° C. for 64 hrs. Reaction was quenched into water (500 mL) and resulting solid product filtered and then slurry washed with water (50 mL). The wet solid was dissolved in ethyl acetate (400 mL), dried over sodium sulfate, filtered thru pad of silica to remove baseline material and filtrate concentrated to give 7.4 gm tan solid. Solid slurried in ~50 mL diethyl ether for 15 min, filtered washed with hexane and solid sucked dry under nitrogen to give 5.73 gm product, I-5. LRMS (ESI) m/z 380.1 [(M+H)$^+$; calcd for C$_{14}$H$_{17}$BrF$_3$N$_3$O: 380.1].

Intermediate I-6

7-(5-bromopyridin-3-yl)-8-methyl-3-(trifluoromethyl)-5,6,7,8-tetrahydroimidazo[1,2-a]pyrazine (I-6)

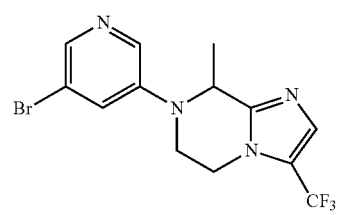

I-6

To a nitrogen degassed mixture of 3,5-dibromopyridine (294 mg, 1.242 mmol), 8-methyl-3-(trifluoromethyl)-5,6,7,8-tetrahydroimidazo[1,2-a]pyrazine hydrochloride (CA, 100 mg, 0.414 mmol) and sodium t-butoxide (119 mg, 1.242 mmol), in Toluene (2 ml) was added BINAP (51.5 mg, 0.083 mmol) and tris(dibenzylideneacetone)dipalladium(0) (37.9 mg, 0.041 mmol). The reaction was sealed and heated at 90° C. for ½ hrs. LCMS (215 nM) showed the reaction complete. The reaction was cooled, quenched into water (10 mL) and aqueous. KHSO$_4$ (2 mL) and ethyl acetate (25 mL) added. Aqueous NaHCO$_3$ was added to adjust pH to 7.5 and the ethyl acetate layer removed. Aqueous layer washed with ethyl acetate (25 mL) and organic extracted combined, washed with brine (10 mL), dried over sodium sulfate and concentrated to an oil. Oil chromatographed on silica using 25-70% ethyl acetate/hexanes to give 71 mg product, I-6, as a foam.

LRMS (ESI) m/z 361.0 [(M+H)$^+$; calcd for C$_{13}$H$_{12}$BrF$_3$N$_4$: 361.0].

Intermediate I-7

3-bromo-5-[2-(1,3-thiazol-2-yl)pyrrolidin-1-yl]pyridine (I-7)

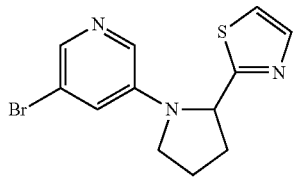

To a nitrogen degassed mixture of 3,5-dibromopyridine (4.61 g, 19.45 mmol), 2-(pyrrolidin-2-yl)thiazole (CA, 1.0 g, 6.48 mmol) and sodium t-butoxide (1.246 g, 12.97 mmol), in Toluene (20 ml) was added binap (0.807 g, 1.297 mmol) and tris(dibenzylideneacetone)di-palladium(0) (0.594 g, 0.648 mmol). The reaction was sealed and heated at 90° C. for 30 min. The reaction was cooled, quenched into water (100 mL), aqueous $KHSO_4$ (20 mL) and ethyl acetate (200 mL) added. Aqueous $NaHCO_3$ was added to adjust pH basic and ethyl acetate layer removed. Aqueous extract washed with ethyl acetate (50 mL) and the organic extracts washed with brine (50 mL), dried over sodium sulfate and concentrated to oil. The oil was chromatographed on silica using 25-75% ethyl acetate/hexanes to give 1.6 g foam of 1-7.

LRMS (ESI) m/z 310.0 [(M+H)$^+$; calcd for $C_{12}H_{12}BrN_3S$: 310.0].

Intermediate 8

2-[(5-bromopyridin-3-yl)amino]-2-cyclopropyl-N-(2,2,2-trifluoroethyl)acetamide (1-8)

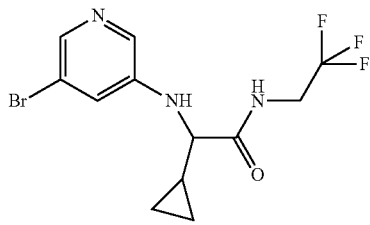

2-[(5-bromopyridin-3-yl)amino]-2-cyclopropyl-N-(2,2,2-trifluoroethyl)acetamide 1-8 was prepared in a manner similar to that utilized to prepare 2-[(5-bromopyridin-3-yl)amino]-3-methyl-N-(2,2,2-trifluoroethyl)butanamide.

LRMS (ESI) m/z 352.0 [(M+H)$^+$; calcd for $C_{12}H_{13}BrF_3N_3O$: 352.0].

Pyrazine Series Intermediates

Intermediate I-9 tert-butyl (2R)-2-[(6-chloropyrazin-2-yl)amino]propanoate (1-9)

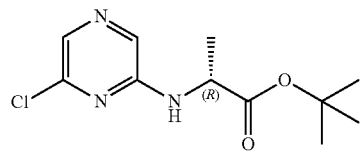

To a reaction vessel was added 2,6-dichloropyrazine (CA, 492 mg, 3.30 mmol), D-Alanine tert-butyl ester hydrochloride (Aldrich Chemical) (500 mg, 2.75 mmol), DMSO (3 mL) and DIPEA (1.923 mL, 11.01 mmol). The resulting solution was heated to 120° C. for 18 hrs. The reaction mixture was cooled and diluted with ethyl acetate (30 mL). The organic layer was washed with aqueous sodium hydrogen carbonate followed by aq. brine. The aqueous layers were back extracted with ethyl acetate and the combined organic layers dried with sodium sulfate, filtered and concentrated to give an oil. The residue was purified by silica gel chromatography on Biotage 50 g SNAP column, eluting with EtOAc/Hexane (10-60%) to give the product, I-9, as a yellow oil. (663 mg, 93%) LRMS (ESI) m/z 258.1 [(M+H)$^+$; calcd for $C_{11}H_{16}ClN_3O_2$: 258.1].

The following compounds, Intermediates I-10 through I-14, depicted in Table 1 were prepared in a similar manner to the above procedures by substitution of the appropriate starting materials.

TABLE 1

| Compound Number | Chemical Structure | IUPAC Name | LRMS (ESI) m/z (M + H)$^+$ |
|---|---|---|---|
| I-10 | 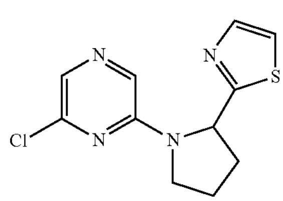 [SMILES: Clc1cncc(N2CCCC2c2nccs2)n1] | 2-chloro-6-[2-(1,3-thiazol-2-yl)pyrrolidin-1-yl]pyrazine | 267.0 |

TABLE 1-continued

| Compound Number | Chemical Structure | IUPAC Name | LRMS (ESI) m/z (M + H)+ |
|---|---|---|---|
| I-11 | 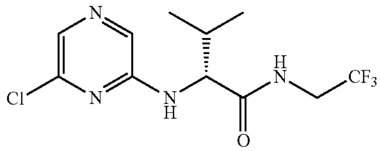 [SMILES: CC(C)[C@@H](Nc1cncc(Cl)n1)C(=O)NCC(F)(F)F] | (2R)-2-[(6-chloropyrazin-2-yl)amino]-3-methyl-N-(2,2,2-trifluoroethyl)butanamide | 311.0 |
| I-12 | 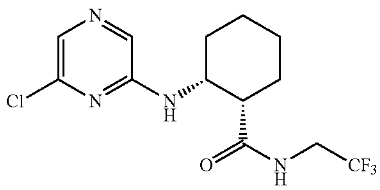 [SMILES: O=C(NCC(F)(F)F)[C@H]1CCCC[C@H]1Nc1cncc(Cl)n1] | (1S,2R)-2-[(6-chloropyrazin-2-yl)amino]-N-(2,2,2-trifluoroethyl)cyclohexanecarboxamide | 337.0 |
| I-13 | 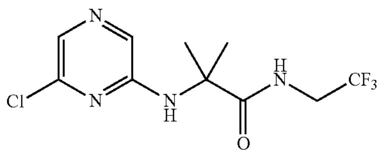 [SMILES: CC(C)(Nc1cncc(Cl)n1)C(=O)NCC(F)(F)F] | 2-[(6-chloropyrazin-2-yl)amino]-2-methyl-N-(2,2,2-trifluoroethyl)propanamide | 297.1 |
| I-14 | 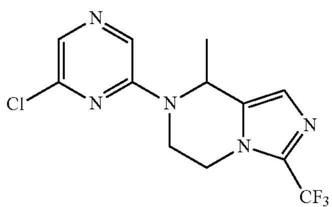 [SMILES: CC1c2cnc(C(F)(F)F)n2CCN1c1cncc(Cl)n1] | 7-(6-chloropyrazin-2-yl)-8-methyl-3-(trifluoromethyl)-5,6,7,8-tetrahydroimidazo[1,5-a]pyrazine | 318.1 |

Triazine Series Intermediates

Intermediate I-15

2-[(3-chloro-1,2,4-triazin-5-yl)amino]-2-methyl-N-(2,2,2-trifluoroethyl) propanamide (I-15)

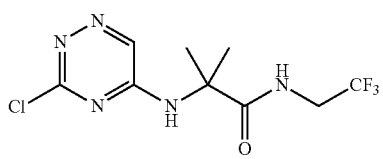

I-15

Step 1 3,5-dichloro-1,2,4-triazine (I-15a)

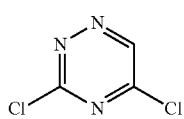

I-15a 1,2,4-triazine-3,5-diol (Aldrich, 2.0 g, 17.68 mmol) was added to a microwave vial flushed with nitrogen. N,N-dimethylaniline (4.0 ml, 31.9 mmol) and POCl3 (20.0 ml, 215 mmol) were then added. The vessel was sealed and irradiated in a microwave at 90° C. for 25 min. The reaction mixture was extracted with hexanes (2×300 ml) and the combined hexane extracts were then passed through a plug of sodium sulfate and celite. The filtrate was concentrated to afford the product as an orange/yellow solid, I-15a, (846 mg, 31.9%). Material used as is without further characterization.

Step 2 2-[(3-chloro-1,2,4-triazin-5-yl)amino]-2-methyl-N-(2,2,2-trifluoroethyl) propanamide (I-15)

To a Dioxane (12.0 ml) solution of 3,5-dichloro-1,2,4-triazine I-15a (846 mg, 5.64 mmol) was added 2-amino-2-methyl-N-(2,2,2-trifluoroethyl) propanamide hydrochloride (1,242 mg, 5.64 mmol) followed by diisopropylethylamine (2.96 ml, 16.92 mmol). Dichloromethane (2 mL) was added and the reaction stirred for 2 hours at room temp. The reaction was diluted with dichloromethane and poured into saturated sodium bicarbonate. A precipitate formed. The solid was filtered washed with dichloromethane and then dried under reduced pressure to afford the product I-15 (1.02 g, 60.3%). LRMS (ESI) m/z 297.9 [(M+H)+; calcd for: $C_9H_{11}ClF_3N_5O$: 298.1].

The Intermediate I-16, shown in Table 2, was prepared in a similar manner to the above procedures by substitution of the appropriate starting material.

TABLE 2

| Intermediate Number | Chemical Structure | IUPAC Name | LRMS (ESI) m/z (M + H)+ |
|---|---|---|---|
| I-16 | 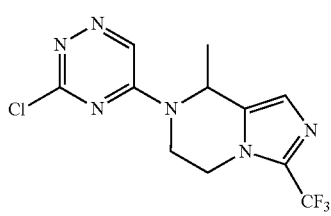 | (2R)-2-[(3-chloro-1,2,4-triazin-5-yl)amino]-N-(2,2,2-trifluoroethyl)propanamide | 283.9 |

Intermediate 17

7-(3-chloro-1,2,4-triazin-5-yl)-8-methyl-3-(trifluoromethyl)-5,6,7,8-tetrahydroimidazo[1,5-a]pyrazine (I-17)

To a Dioxane (12.0 ml) solution of 3,5 dichloro-1,2,4-triazine (780 mg, 5.20 mmol) was added 8-methyl-3-(trifluoromethyl)-5,6,7,8-tetrahydroimidazo[1,5-a]pyrazine hydrochloride (CA, 1257 mg, 5.20 mmol) followed by diisopropylethylamine (2.73 ml, 15.60 mmol). Dichloromethane (2 mL) was added to solubilize the reaction. The reaction was stirred for 2 hrs at RT and then diluted with DCM. The reaction was washed with saturated sodium bicarbonate then brine, dried with sodium sulfate and concentrated to anoil. Purification of the oil on Biotage Normal Phase system (DCM:MeOH, 0-9% B) to afford the product as a solid, 1-17, (1.2 g, 71.7%). LRMS (ESI) m/z 319.1 [(M+H)+; calcd for $C_{11}H_{10}ClF_3N_6$: 319.1].

The following compounds, Intermediates I-18 through I-20, shown in Table 3, were prepared in a similar manner to the above procedures by substitution of the appropriate starting materials.

TABLE 3

| Intermediate Number | Chemical Structure | IUPAC Name | LRMS (ESI) m/z (M + H)+ |
|---|---|---|---|
| I-18 | 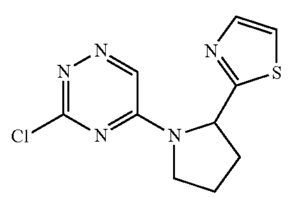 [SMILES: Clc1nncc(N2CCCC2c2nccs2)n1] | 3-chloro-5-[2-(1,3-thiazol-2-yl)pyrrolidin-1-yl]-1,2,4-triazine | 268.0 |
| I-19 | 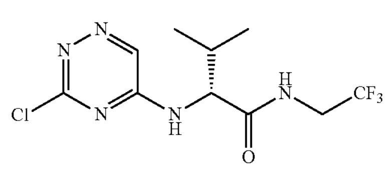 [SMILES: CC(C)[C@@H](Nc1cnnc(Cl)n1)C(=O)NCC(F)(F)F] | (2R)-2-[(3-chloro-1,2,4-triazin-5-yl)amino]-3-methyl-N-(2,2,2-trifluoroethyl)-butanamide | 312.0 |
| I-20 | 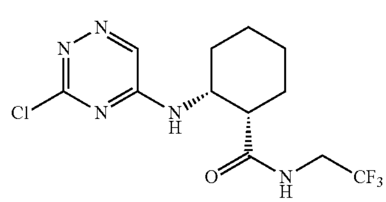 [SMILES: O=C(NCC(F)(F)F)[C@H]1CCCC[C@H]1Nc1cnnc(Cl)n1] | (1S,2R)-2-[(3-chloro-1,2,4-triazin-5-yl)amino]-N-(2,2,2-trifluoroethyl) cyclohexanecarboxamide | 338.0 |

Pyridazine Series Intermediates

Intermediate I-21

2-[(6-chloropyridazin-4-yl)amino]-2-methyl-N-(2,2,2-trifluoroethyl) propanamide (I-21)

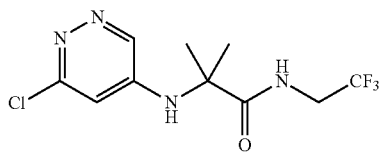

I-21

Step 1 tert-butyl 2-[(6-chloropyridazin-4-yl)amino]-2-methylporpanoate (I-21a)

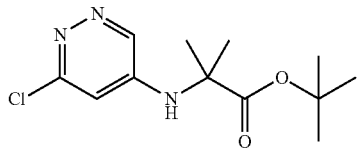

I-21a 3,5-dichloropyridazine (CA, 3.0 g, 20.14 mmol), tert-butyl 2-amino-2-methylpropanoate hydrochloride (CHEM-IM-PEX, 4.33 g, 22.15 mmol), and diisopropylethylamine (10.55 mL, 60.4 mmol) were added to DMSO (20.0 ml) in a pressure vessel. The reaction was sealed and heated for 17 hrs at 120° C. in an oil bath. The reaction was cooled concentrated in vacuo. The residue was dissolved in ethyl acetate (100 mL) and washed with saturated sodium bicarbonate. The aqueous layer was removed and back extracted with ethyl acetate (3×50 mL). The combined organic extracts were washed with brine, dried with sodium sulfate and concentrated to an oil. Purification on Biotage Normal Phase system (DCM:MeOH, 0-9% B) to afford the product I-21a (1.24 g, 22.21%).

LRMS (ESI) m/z 272.0 [(M+H)$^+$; calcd for $C_{12}H_{18}ClN_3O_2$: 272.0].

Step 2 2-[(6-chloropyridazin-4-yl)amino]-2-methylpropanoic acid dihydrochloride (I-21b)

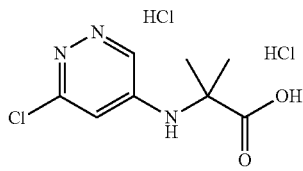

I-21b

To a solution of Tert-butyl 2-[(6-chloropyridazin-4-yl)amino]-2-methylporpanoate I-21a (1.799 g, 6.62 mmol) in DCM (16.0 ml) was added TFA (8.0 ml, 104 mmol). The reaction was stirred at RT for 17 hrs. 4M HCl in Dioxane (50 ml, 200 mmol) was added and the mixture concentrated to an oil in vacuo. Diethyl ether was added and a solid precipitated. The solid was filtered, washed with diethyl ether and dried under vacuum to afford the product I-21b as the dichloride salt (1.234 g, 62.7%).

LRMS (ESI) m/z 216.0 [(M+H)$^+$; calcd for $C_8H_{10}ClN_3O_2$: 216.0].

Step 3 2-[(6-chloropyridazin-4-yl)amino]-2-methyl-N-(2,2,2-trifluoroethyl) propanamide (I-21)

2-[(6-chloropyridazin-4-yl)amino]-2-methylpropanoic acid dihydrochloride I-21b (1.23 g, 4.26 mmol), HOBT (0.979 g, 6.39 mmol), EDC (1.226 g, 6.39 mmol), and trifluoroethyl amine hydrochloride (0.866 g, 6.39 mmol) were added to DCM (20.0 ml) followed by the addition of TEA (29.7 ml, 213 mmol). The reaction was allowed to stir at room temperature for 17 hrs. The reaction was then diluted with DCM, washed with saturated sodium bicarbonate, brine, dried with sodium sulfate and concentrated in vacuo to an oil. Purification on Biotage Normal Phase system (DCM:MeOH, 0-8% B) to afford the product I-21 as a solid. The solid was dried under vacuum (295 mg, 22.3%). LRMS (ESI) m/z 297.0 [(M+H)$^+$; calcd for $C_{10}H_{12}ClF_3N_4O$: 297.0].

Intermediate 22

(Cis)-2-[(6-chloropyridazin-4-yl)amino]-N-(2,2,2-trifluoroethyl)cyclohexanecarboxamide (I-22)

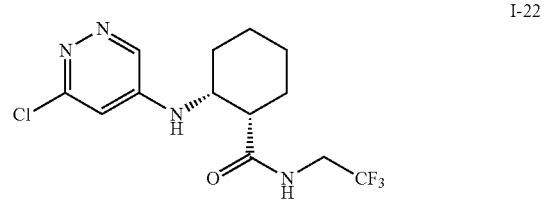 [SMILES: O=C(NCC(F)(F)F)[C@H]1CCCC[C@H]1Nc1cnnc(Cl)c1]

I-22

Step 1 Ethyl (cis)-2-[(6-chloropyridazin-4-yl)amino]cyclohexanecarboxylate (I-22a)

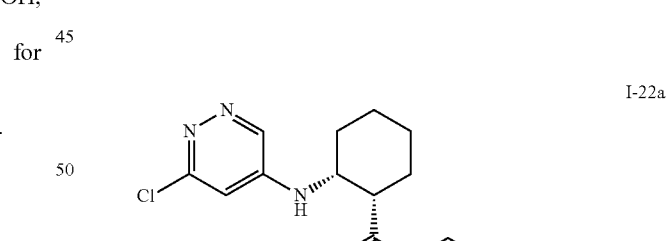

I-22a 3,5-dichloropyridazine (1.6 g, 10.74 mmol), ethyl (cis)-2-aminocyclohexanecarboxylate hydrochloride (CA, 2.454 g, 11.81 mmol), and triethylamine (5.63 mL, 32.2 mmol) were added to DMSO (10.0 ml) and heated for 5 hrs at 120° C. and then allowed to stir at room temperature for 24 hr. Solvents were removed in vacuo. The residue was dissolved in EtOAc and then poured into sat. sodium bicarb. The aqeuous layer was removed and back extracted with EtOAc. The combined organics were washed with brine, dried over sodium sulfate and concentrated to an oil. Purification on biotage again (DCM:MeOH, 0-9% B) and concentration afforded the product, I-22a, as a solid (2.207 g, 71.7%).

LRMS (ESI) m/z 284.0 [(M+H)⁺; calcd for C₁₃H₁₈ClN₃O₂: 284.0].

Step 2 (Cis)-2-[(6-chloropyridazin-4-yl)amino]cyclohexanecarboxylic acid (I-22b)

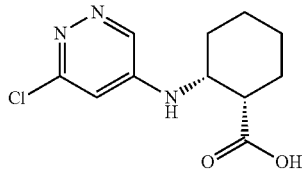

I-22b

To a solution of Ethyl (1S,2R)-2-[(6-chloropyridazin-4-yl)amino]I-22a (295 mg, 1.036 mmol) in tetrahydrofuran (3.0 ml) was added 1M NaOH (1.554 mL, 1.554 mmol). The reaction was allowed to stir for 17 hr. The reaction was then acidified with acetic acid diluted with EtOAc and washed with saturated sodium bicarbonate, brine, dried with sodium sulfate and concentrated to an oil. The solid was dried under reduced pressure for 17 hrs to afford the product, I-22b. (205 mg, 71.7%).

LRMS (ESI) m/z 257.0 [(M+H)⁺; calcd for C₁₁H₁₄ClN₃O₂: 257.0].

Step 3 (Cis)-2-[(6chloropyridazin-4-yl)amino]-N-(2,2,2-trifluoroethyl)cyclohexanecarboxamide (I-22)

(Cis)-2-[(6-chloropyridazin-4-yl)amino]cyclohexanecarboxylic acid I-22b (2.2 g, 8.60 mmol), HOBT (2.64 g, 17.21 mmol), EDC (3.30 g, 17.21 mmol) and trifluoroethyl amine hydrochloride (2.332 g, 17.21 mmol) were added to DCM (30.0 ml) followed by the addition of TEA (6.00 ml, 43.0 mmol). The slurry was allowed to stir at RT for 17 hr. The reaction was diluted with dichloromethane washed with sat. sodium bicarb., brine dried with sodium sulfate and concentrated to an oil. Purification on Biotage Normal Phase system (DCMeOH, 0-8% B) afforded the product I-22 as a solid. (1.56 g, 51.2%).

LRMS (ESI) m/z 337.0 [(M+H)⁺; calcd for C₁₃H₁₆ClF₃N₄O: 337.0].

The Intermediates I-23 through I-26, shown in Table 4, were prepared in a similar manner to the above procedures utilizing appropriate starting materials.

TABLE 4

| Intermediate Number | Chemical Structure | IUPAC Name | LRMS (ESI) m/z (M + H)⁺ |
|---|---|---|---|
| I-23 | 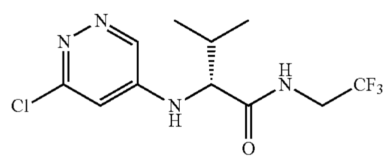 [SMILES: CC(C)[C@@H](Nc1cnnc(Cl)c1)C(=O)NCC(F)(F)F] | (2R)-2-[(6-chloropyridazin-4-yl)amino]-3-methyl-N-(2,2,2-trifluoroethyl)butanamide | 311.0 |
| I-24 | 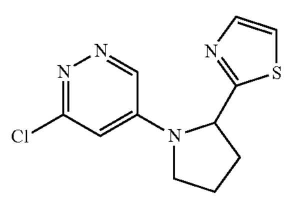 [SMILES: Clc1cc(N2CCCC2c2nccs2)cnn1] | 3-chloro-5-[2-(1,3-thiazol-2-yl)pyrrolidin-1-yl]pyridazine | 267.0 |
| I-25 | 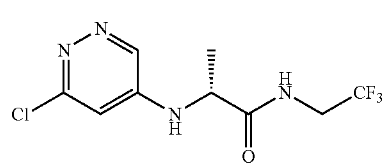 [SMILES: C[C@@H](Nc1cnnc(Cl)c1)C(=O)NCC(F)(F)F] | (2R)-2-[(6-chloropyridazin-4-yl)amino]-N-(2,2,2-trifluoroethyl)propanamide | 282.9 |
| I-26 | 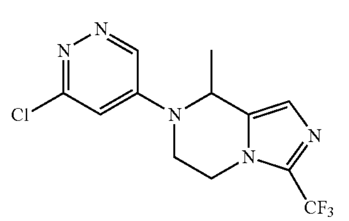 [SMILES: CC1c2cnc(C(F)(F)F)n2CCN1c1cnnc(Cl)c1] | 7-(6-chloropyridazin-4-yl)-8-methyl-3-(trifluoromethyl)-5,6,7,8-tetrahydroimidazo[1,5-a]pyrazine | 318.1 |

Intermediate 27

N²-(5-bromopyridin-3-yl)-3-hydroxy-N-(2,2,2-trifluoroethyl)-D-valinamide (I-27)

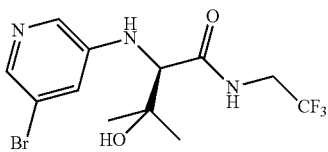

I-27

Step 1 N²-(tert-butoxycarbonyl)-3-hydroxy-N-(2,2,2-trifluoroethyl)-D-valinamide (I-27a)

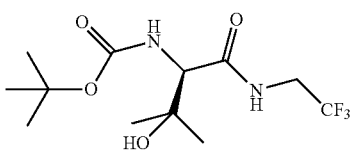

I-27a

To a vial was added (R)—N-Boc-2-amino-3-hydroxy-3-methylbutanoic acid (CA, 500 mg, 2.144 mmol), 2,2,2-trifluoroethanamine hydrochloride (581 mg, 4.29 mmol), EDC (493 mg, 2.57 mmol), and HOBT (328 mg, 2.144 mmol). The reactants were dissolved in DCM (10 mL) and then DIEA (1.497 mL, 8.57 mmol) was added. The mixture was allowed to stir at RT overnight. The mixture was diluted with ethyl acetate, washed 2× with aqueous sodium hydrogen carbonate and 1× with brine. Aqueous layers were back extracted once with ethyl acetate, combined organic layers were dried with Na2SO4, filtered and the solvent was evaporated under reduced pressure. The material I-27a was used directly in the subsequent step without purification.

Step 2 3-hydroxy-N-(2,2,2-trifluoroethyl)-D-valinamide.HCl (I-27b)

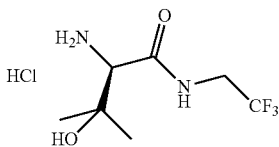

I-27b

N²-(tert-butoxycarbonyl)-3-hydroxy-N-(2,2,2-trifluoroethyl)-D-valinamide I-27b (510 mg, 1.62 mmol) was dissolved in dichloromethane (6 mL) and HCl (4M in Dioxane) (2.4 mL, 9.7 mmol) was added. The solution was stirred at RT for 1 h. Solvent evaporation gave crude title compound I-27b as the HCl salt, which was used without further purification in the subsequent step.

Step 3 N²-(5-bromopyridin-3-yl)-3-hydroxy-N-(2,2,2-trifluoroethyl)-D-valinamide (I-27)

To a mixture of 3,5-dibromopyridine (378 mg, 1.6 mmol), 3-hydroxy-N-(2,2,2-trifluoroethyl)-D-valinamide.HCl I-27b (400 mg, 1.6 mmol), potassium carbonate (882 mg, 6.38 mmol) and L-proline (36.7 mg, 0.319 mmol), in DMSO (5 mL) and degassed with nitrogen was added copper(I) iodide (STREM crushed) (30.4 mg, 0.160 mmol). The reaction was sealed and heated at 80° C. for 64 h. The reaction was quenched into water and extracted with DCM. The organic layer was washed with aq. NaHCO₃, dried over sodium sulfate, filtered and concentrated. The residue was purified on silica gel (EtOAc/hexane; 25-100%) to afford the title compound I-27. MS APCI: [M+H]⁺ m/z=371.1. ¹H NMR (600 MHz, DMSO) δ 8.57 (t, J=6.5 Hz, 1H), 8.03 (s, 1H), 7.78 (s, 1H), 7.17 (s, 1H), 6.17 (d, J=6.5 Hz, 1H), 4.77 (s, 1H), 3.85 (m, 2H), 3.80 (d, J=6.5 Hz, 1H), 1.07 (s, 3H), 1.06 (s, 3H).

EXAMPLES

Example generated via General Scheme 1:

Example 1-1

(2R)-2-{[5-(5-chloro-1H-pyrrolo[2,3-b]pyridin-3-yl)pyridin-3-yl]amino}-3-methyl-N-(2,2,2-trifluoroethyl)butanamide (1-1)

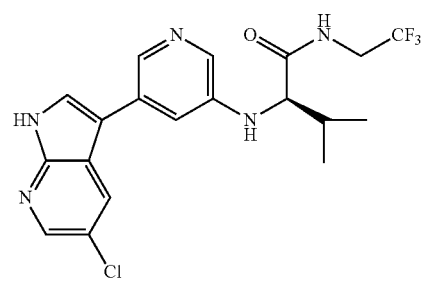

1-1

Step 1 2-{[5-(5-chloro-1-[(4-methylphenyl)sulfonyl]-1H-pyrrolo[2,3-b]pyridin-3-yl)pyridin-3-yl]amino}-3-methyl-N-(2,22-trifluoroethyl)butanamide (1-a)

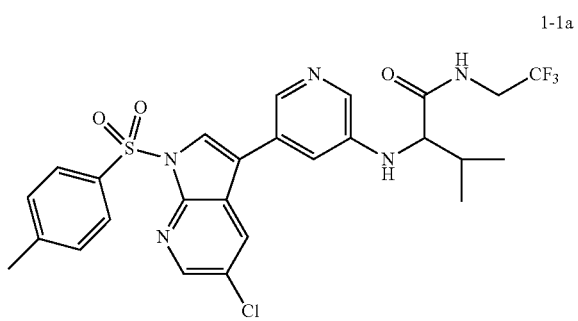 [SMILES: Cc1ccc(S(=O)(=O)n2cc(-c3cncc(NC(C(=O)NCC(F)(F)F)C(C)C)c3)c3cc(Cl)cnc32)cc1]

1-1a

To a nitrogen gas purged mixture of 5-chloro-3-bispinacolborane-1-[(4-methylphenyl)sulfonyl]-1H-pyrrolo[2,3-b]pyridine (269 mg, 0.621 mmol), 2-[(5-bromopyridin-3-yl)amino]-3-methyl-N-(2,2,2-trifluoroethyl)butanamide (200 mg, 0.565 mmol), and aqueous Na₂CO₃ (847 μl, 1.694 mmol) in dimethoxyethane (3.8 mL) was added tetrakistriphenylphosphine Pd(0) (131 mg, 0.113 mmol). The reaction mixture was heated at 100° C. in a sealed microwave vessel for 1 hr, quenched into water (10 mL) and extracted with ethyl acetate (2×20 mL). The combined organic extracts were dried with sodium sulfate, concentrated, and chromatographed on silica (50-100% ethyl acetate/hexane, 25 gm silica) to give the desired product 1-1a as a foam, 315 mg, 98%.

LRMS (ESI) m/z 580.1 [(M+H)$^+$; calcd for $C_{26}H_{25}ClF_3N_5O_3S$: 580.1].

Step 2 2-{[5-(5-chloro-1H-pyrrolo[2,3-b]pyridin-3-yl)pyridin-3-yl]amino}-3-methyl-N-(2,2,2-trifluoroethyl)butanamide (1-1b)

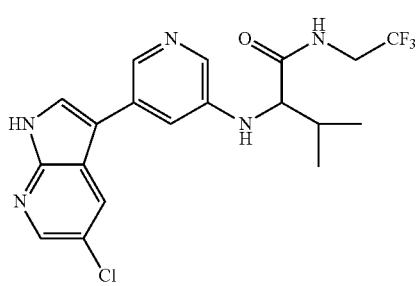

To a solution of 2-{[5-(5-chloro-1-[(4-methylphenyl)sulfonyl]-1H-pyrrolo[2,3-b]pyridin-3-yl)pyridin-3-yl]amino}-3-methyl-N-(2,2,2-trifluoroethyl)butanamide 1-1a (315 mg, 0.543 mmol) dissolved in a mixture of MeOH (3.0 ml) and THF (7 ml) was added ethylenediamine (0.183 ml, 2.72 mmol) followed by 1 M sodium hydroxide (1.086 ml, 1.086 mmol). The mixture was allowed to stir for ½ hr at room temperature. The reaction was quenched with 1N HCL (2.7 mL), concentrated to remove solvents and aqueous sodium bicarbonate (10 mL) added. The product was extracted into DCM, dried over sodium sulfate, concentrated and chromatographed on silica using 1-10% methanol/dichloromethane to give 135 mg desired product 1-1b as a foam. LRMS (ESI) m/z 426.1 [(M+H)$^+$; calcd for $C_{19}H_{19}ClF_3N_5O$: 426.1].

Step 3 (2R)-2-{[5-(5-chloro-1H-pyrrolo[2,3-b]pyridin-3-yl)pyridin-3-yl]amino}-3-methyl-N-(2,2,2-trifluoroethyl)butanamide (1-1)

The racemate 2-{[5-(5-chloro-1H-pyrrolo[2,3-b]pyridin-3-yl)pyridin-3-yl]amino}-3-methyl-N-(2,2,2-trifluoroethyl)butanamide 1-1b (230 mg) was separated by SFC chromatography (Chiral Technology AD-H 2.1×25 cm, 5 uM, 30%/70% Methanol/CO2, 65 mL/Min, 7 min run time, 220 nm) to give peak 1 (2R)-2-{[5-(5-chloro-1H-pyrrolo[2,3-b]pyridin-3-yl)pyridin-3-yl]amino}-3-methyl-N-(2,2,2-trifluoroethyl)butanamide (110 mg, RT-1.8 min) and peak 2 (2S)-2-{[5-(5-chloro-1H-pyrrolo[2,3-b]pyridin-3-yl)pyridin-3-yl]amino}-3-methyl-N-(2,2,2-trifluoroethyl)butanamide (90 mg, 4.6 min).

Peak 1 LRMS (ESI) m/z 426.1 [(M+H)$^+$; calcd for $C_{19}H_{19}ClF_3N_5O$: 426.1].

Peak 2 LRMS (ESI) m/z 426.1 [(M+H)$^+$; calcd for $C_{19}H_{19}ClF_3N_5O$: 426.1].

Example 1-2

2-{[5-(5-fluoro-1H-pyrrolo[2,3-b]pyridin-3-yl)pyridin-3-yl]amino}-3-methyl-N-(2,2,2-trifluoroethyl)butanamide (1-2)

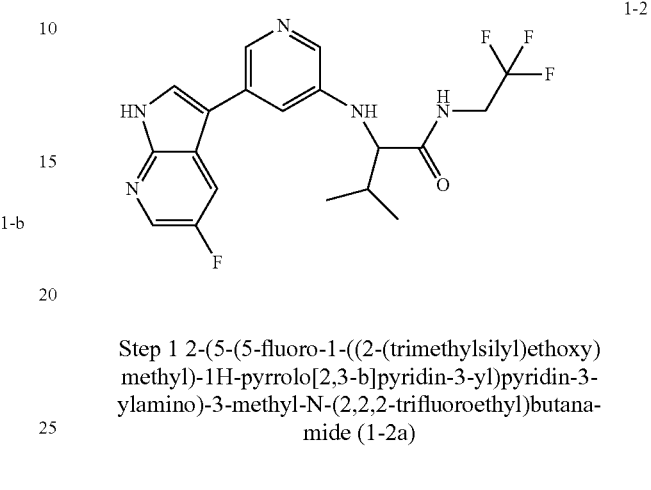

Step 1 2-(5-(5-fluoro-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide (1-2a)

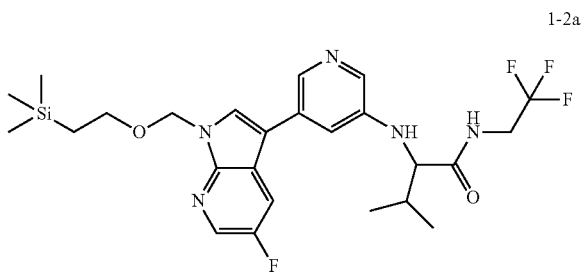 [SMILES: CC(C)C(Nc1cncc(-c2cn(COCC[Si](C)(C)C)c3ncc(F)cc23)c1)C(=O)NCC(F)(F)F]

To a nitrogen gas purged mixture of 5-fluoro-3-bispinacolborane-1-[(2-(trimethylsilyl)ethoxy)methyl]-1H-pyrrolo[2,3-b]pyridine (97 mg, 0.248 mmol), 2-[(5-bromopyridin-3-yl)amino]-3-methyl-N-(2,2,2-trifluoroethyl)butanamide I-2 (80 mg, 0.226 mmol), and $Na_2CO_3$ (0.339 ml, 0.678 mmol) in DME (1.0 ml) was added Tetrakis (52.2 mg, 0.045 mmol). The reaction mixture was heated at 100° C. in a sealed microwave vessel for 1 h. Water (10 mL) was added and the mixture was extracted with ethyl acetate (2×20 mL). The combined organic fractions were dried with sodium sulfate, and concentrated under reduced pressure. Purification of the residue on silica (25-100% ethyl acetate/hex, 25 gm silica) gave the desired product 1-2a as an oil (78 mg).

LRMS (ESI) m/z 540 [(M+H)$^+$; calcd for $C_{25}H_{33}F_4N_5O_2Si$: 540].

Step 2 2-{[5-(5-fluoro-1H-pyrrolo[2,3-b]pyridin-3-yl)pyridin-3-yl]amino}-3-methyl-N-(2,2,2-trifluoroethyl)butanamide (1-2)

2-(5-(5-fluoro-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide 1-2a (78 mg, 0.145 mmol) was dissolved in DCM (2 ml). TFA (1.114 ml, 14.45 mmol) was added and mixture allowed to stir for 1 hr. Reaction concentrated then resuspended in MeOH (4 ml) and ethylenediamine (0.020 ml, 0.289 mmol) and sodium hydroxide (10 M aqueous) (0.101 ml, 1.012 mmol) added. After 30 min the reaction was treated with HCL (1.012 ml, 1.012 mmol) concentrated in vacuo and the residue was purified by preparative HPLC Reverse phase (C-18). (5-95% Acetonitrile/ 0.1% TFA/water). Product fractions were treated with aq. NaHCO₃, concentrated and product extracted into DCM and ethyl acetate. Extracts dried over sodium sulfate, filtered and concentrated to give white solid 1-2. (40 mg).

LRMS (ESI) m/z 410.1 [(M+H)⁺; calcd for $C_{19}H_{19}F_4N_5O$: 410.2].

The following examples, 1-3 through 1-53, as shown in Table 5, were prepared in an analogous manner of that described above using materials that are commercially available or known, or that can be prepared using procedures known in the art or by generally following procedures described herein for various intermediates

TABLE 5

| Example Number | Structure | IUPAC Name | Exact Mass [M + H]+ |
|---|---|---|---|
| 1-3 | 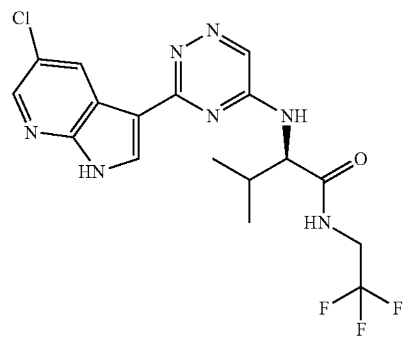 [SMILES: CC(C)[C@@H](Nc1cnnc(-c2c[nH]c3ncc(Cl)cc23)n1)C(=O)NCC(F)(F)F] | N~2~-[3-(5-chloro-1H-pyrrolo[2,3-b]pyridin-3-yl)-1,2,4-triazin-5-yl]-N-(2,2,2-trifluoroethyl)-D-valinamide | Calc'd 428.1, found 428.0 |
| 1-4 | 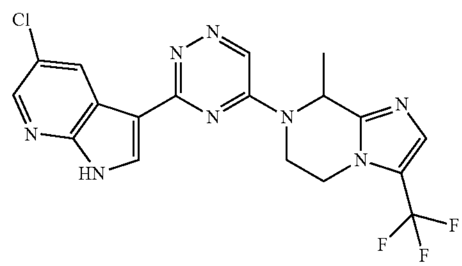 | 7-[3-(5-chloro-1H-pyrrolo[2,3-b]pyridin-3-yl)-1,2,4-triazin-5-yl]-8-methyl-3-(trifluoromethyl)-5,6,7,8-tetrahydroimidazo[1,2-a]pyrazine | Calc'd 435.1, found 435.0 |
| 1-5 | 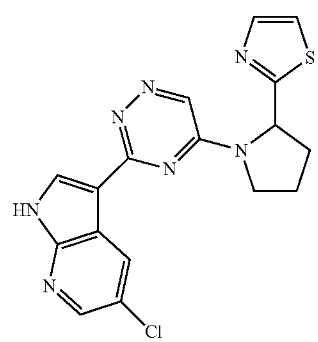 [SMILES: Clc1cnc2[nH]cc(-c3nncc(N4CCCC4c4nccs4)n3)c2c1] | 5-chloro-3-{5-[2-(1,3-thiazol-2-yl)pyrrolidin-1-yl]-1,2,4-triazin-3-yl}-1H-pyrrolo[2,3-b]pyridine | Calc'd 384.1, found 384.0 |
| 1-6 | 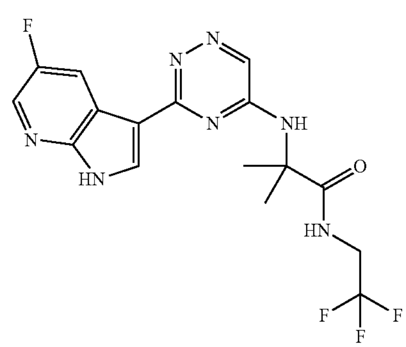 [SMILES: CC(C)(Nc1cnnc(-c2c[nH]c3ncc(F)cc23)n1)C(=O)NCC(F)(F)F] | N~2~-[3-(5-fluoro-1H-pyrrolo[2,3-b]pyridin-3-yl)-1,2,4-triazin-5-yl]-2-methyl-N-(2,2,2-trifluoroethyl)alaninamide | Calc'd 398.1, found 398.0 |

TABLE 5-continued

| Example Number | Structure | IUPAC Name | Exact Mass [M + H]+ |
|---|---|---|---|
| 1-7 | 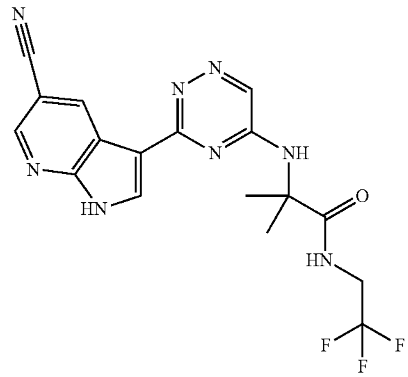 [SMILES: CC(C)(Nc1cnnc(-c2c[nH]c3ncc(C#N)cc23)n1)C(=O)NCC(F)(F)F] | N~2~-[3-(5-cyano-1H-pyrrolo[2,3-b]pyridin-3-yl)-1,2,4-triazin-5-yl]-2-methyl-N-(2,2,2-trifluoroethyl)alaninamide | Calc'd 405.1, found 405.0 |
| 1-8 | 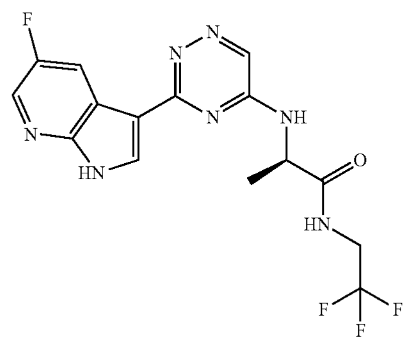 [SMILES: C[C@@H](Nc1cnnc(-c2c[nH]c3ncc(F)cc23)n1)C(=O)NCC(F)(F)F] | N~2~-[3-(5-fluoro-1H-pyrrolo[2,3-b]pyridin-3-yl)-1,2,4-triazin-5-yl]-N-(2,2,2-trifluoroethyl)-D-alaninamide | Calc'd 384.1, found 384.0 |
| 1-9 | 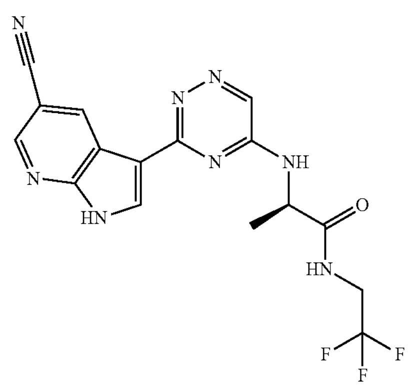 [SMILES: C[C@@H](Nc1cnnc(-c2c[nH]c3ncc(C#N)cc23)n1)C(=O)NCC(F)(F)F] | N~2~-[3-(5-cyano-1H-pyrrolo[2,3-b]pyridin-3-yl)-1,2,4-triazin-5-yl]-N-(2,2,2-trifluoroethyl)-D-alaninamide | Calc'd 391.1, found 391.0 |
| 1-10 | 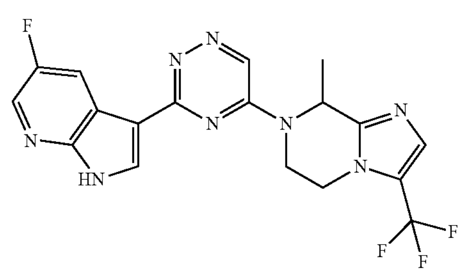 | 7-[3-(5-fluoro-1H-pyrrolo[2,3-b]pyridin-3-yl)-1,2,4-triazin-5-yl]-8-methyl-3-(trifluoromethyl)-5,6,7,8-tetrahydroimidazo[1,2-a]pyrazine | Calc'd 419.1, found 419.0 |

TABLE 5-continued

| Example Number | Structure | IUPAC Name | Exact Mass [M + H]+ |
|---|---|---|---|
| 1-11 | 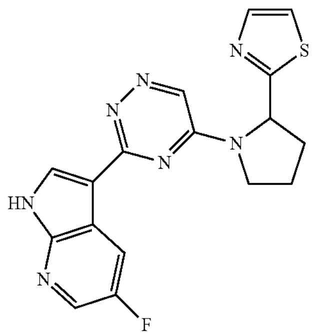 [SMILES: Fc1cnc2[nH]cc(-c3nncc(N4CCCC4c4nccs4)n3)c2c1] | 5-fluoro-3-{5-[2-(1,3-thiazol-2-yl)pyrrolidin-1-yl]-1,2,4-triazin-3-yl}-1H-pyrrolo[2,3-b]pyridine | Calc'd 368.1, found 368.0 |
| 1-12 | 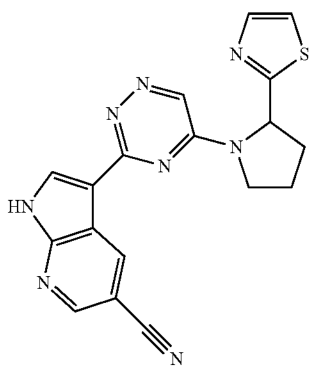 [SMILES: N#Cc1cnc2[nH]cc(-c3nncc(N4CCCC4c4nccs4)n3)c2c1] | 3-{5-[2-(1,3-thiazol-2-yl)pyrrolidin-1-yl]-1,2,4-triazin-3-yl}-1H-pyrrolo[2,3-b]pyridine-5-carbonitrile | Calc'd 375.1, found 375.0 |
| 1-13 | 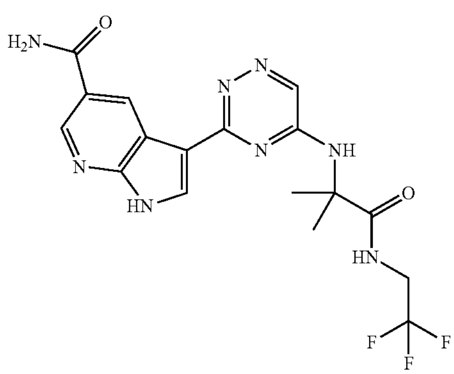 [SMILES: CC(C)(Nc1cnnc(-c2c[nH]c3ncc(C(N)=O)cc23)n1)C(=O)NCC(F)(F)F] | 3-[5-({1,1-dimethyl-2-oxo-2-[(2,2,2-trifluoroethyl)amino]ethyl}amino)-1,2,4-triazin-3-yl]-1H-pyrrolo[2,3-b]pyridine-5-carboxamide | Calc'd 423.2, found 423.3 |
| 1-14 | 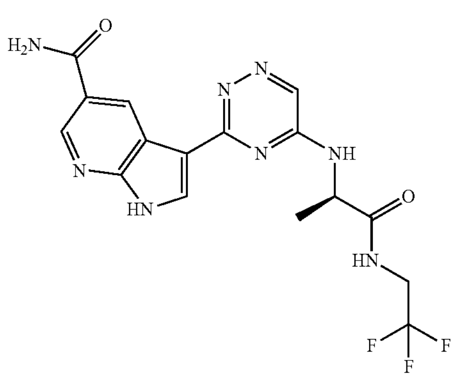 [SMILES: C[C@@H](Nc1cnnc(-c2c[nH]c3ncc(C(N)=O)cc23)n1)C(=O)NCC(F)(F)F] | 3-[5-({(1R)-1-methyl-2-oxo-2-[(2,2,2-trifluoroethyl)amino]ethyl}amino)-1,2,4-triazin-3-yl]-1H-pyrrolo[2,3-b]pyridine-5-carboxamide | Calc'd 409.1, found 409.0 |

TABLE 5-continued

| Example Number | Structure | IUPAC Name | Exact Mass [M + H]+ |
|---|---|---|---|
| 1-15 | 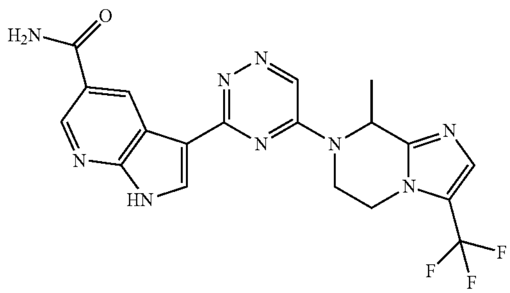 [SMILES: CC1c2ncc(C(F)(F)F)n2CCN1c1cnnc(-c2c[nH]c3ncc(C(N)=O)cc23)n1] | 3-{5-[8-methyl-3-(trifluoromethyl)-5,6-dihydroimidazo[1,2-a]pyrazin-7(8H)-yl]-1,2,4-triazin-3-yl}-1H-pyrrolo[2,3-b]pyridine-5-carboxamide | Calc'd 444.2, found 444.0 |
| 1-16 | 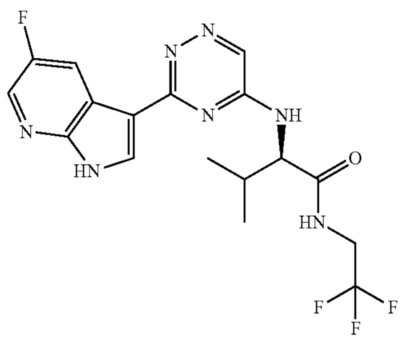 [SMILES: CC(C)[C@@H](Nc1cnnc(-c2c[nH]c3ncc(F)cc23)n1)C(=O)NCC(F)(F)F] | N~2~-[3-(5-fluoro-1H-pyrrolo[2,3-b]pyridin-3-yl)-1,2,4-triazin-5-yl]-N-(2,2,2-trifluoroethyl)-D-valinamide | Calc'd 412.2, found 412.0 |
| 1-17 | 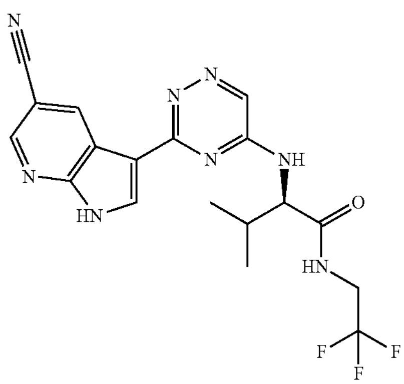 [SMILES: CC(C)[C@@H](Nc1cnnc(-c2c[nH]c3ncc(C#N)cc23)n1)C(=O)NCC(F)(F)F] | N~2~-[3-(5-cyano-1H-pyrrolo[2,3-b]pyridin-3-yl)-1,2,4-triazin-5-yl]-N-(2,2,2-trifluoroethyl)-D-valinamide | Calc'd 419.2, found 419.1 |
| 1-18 | 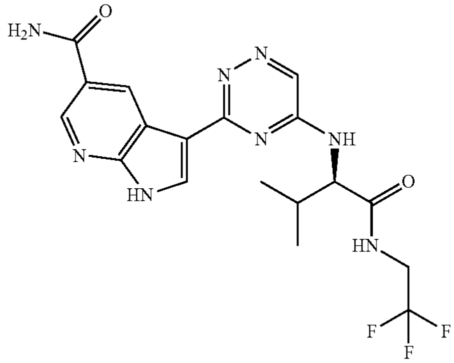 [SMILES: CC(C)[C@@H](Nc1cnnc(-c2c[nH]c3ncc(C(N)=O)cc23)n1)C(=O)NCC(F)(F)F] | 3-[5-({(1R)-2-methyl-1-[(2,2,2-trifluoroethyl)carbamoyl]propyl}amino)-1,2,4-triazin-3-yl]-1H-pyrrolo[2,3-b]pyridine-5-carboxamide | Calc'd 437.2, found 437.1 |

TABLE 5-continued

| Example Number | Structure | IUPAC Name | Exact Mass [M + H]+ |
|---|---|---|---|
| 1-19 | 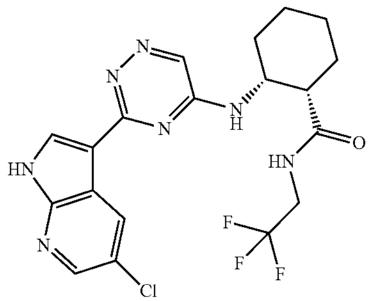 [SMILES: O=C(NCC(F)(F)F)[C@H]1CCCC[C@H]1Nc1cnnc(-c2c[nH]c3ncc(Cl)cc23)n1] | (1S,2R)-2-{[3-(5-chloro-1H-pyrrolo[2,3-b]pyridin-3-yl)-1,2,4-triazin-5-yl]amino}-N-(2,2,2-trifluoroethyl)cyclohexane-carboxamide | Calc'd 454.1, found 454.0 |
| 1-20 | 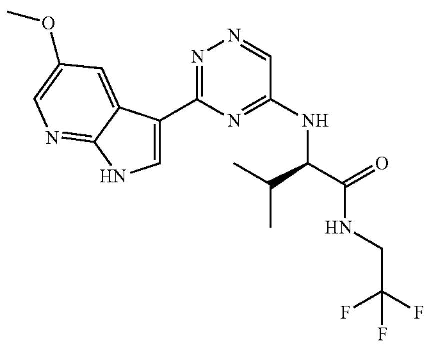 [SMILES: COc1cnc2[nH]cc(-c3nncc(N[C@@H](C(=O)NCC(F)(F)F)C(C)C)n3)c2c1] | N~2~-[3-(5-methoxy-1H-pyrrolo[2,3-b]pylidin-3-yl)-1,2,4-triazin-5-yl]-N-(2,2,2-trifluoroethyl)-D-valinamide | Calc'd 424.2, found 424.1 |
| 1-21 | 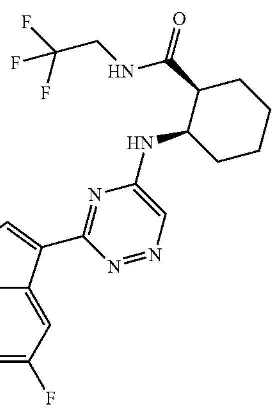 | (1S,2R)-2-{[3-(5-fluoro-1H-pyrrolo[2,3-b]pyridin-3-yl)-1,2,4-triazin-5-yl]amino}-N-(2,2,2-trifluoroethyl)cyclohexane-carboxamide | Calc'd 438.2, found 438.2 |
| 1-22 | 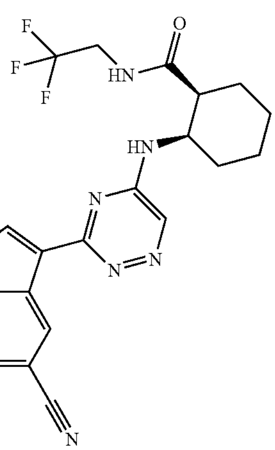 | (1S,2R)-2-{[3-(5-cyano-1H-pyrrolo[2,3-b]pyridin-3-yl)-1,2,4-triazin-5-yl]amino}-N-(2,2,2-trifluoroethyl)cyclohexane-carboxamide | Calc'd 445.2, found 445.2 |

TABLE 5-continued

| Example Number | Structure | IUPAC Name | Exact Mass [M + H]+ |
|---|---|---|---|
| 1-23 | 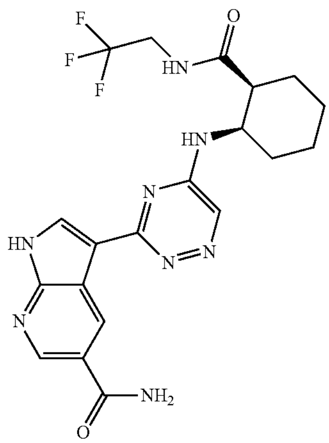 [SMILES: NC(=O)c1cnc2[nH]cc(-c3nncc(N[C@@H]4CCCC[C@@H]4C(=O)NCC(F)(F)F)n3)c2c1] | 3-[5-({(1R,2S)-2-[(2,2,2-trifluoroethyl)carbamoyl]cyclohexyl}amino)-1,2,4-triazin-3-yl]-1H-pyrrolo[2,3-b]pyridine-5-carboxamide | Calc'd 463.2, found 463.2 |
| 1-24 | 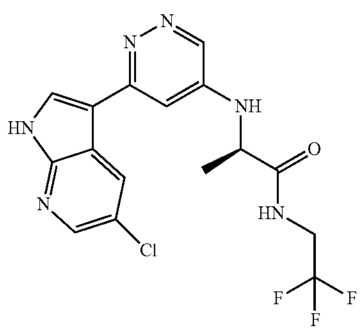 [SMILES: C[C@@H](Nc1cnnc(-c2c[nH]c3ncc(Cl)cc23)c1)C(=O)NCC(F)(F)F] | N~2~-[6-(5-chloro-1H-pyrrolo[2,3-b]pyridin-3-yl)pyridazin-4-yl]-N-(2,2,2-trifluoroethyl)-D-alaninamide | Calc'd 399.1, found 398.9 |
| 1-25 | 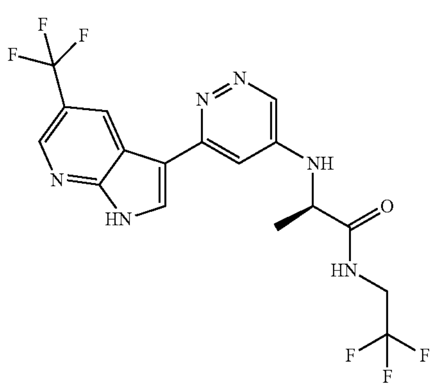 [SMILES: C[C@@H](Nc1cnnc(-c2c[nH]c3ncc(C(F)(F)F)cc23)c1)C(=O)NCC(F)(F)F] | N-(2,2,2-trifluoroethyl)-N~2~-{6-[5-(trifluoromethyl)-1H-pyrrolo[2,3-b]pyridin-3-yl]pyridazin-4-yl}-D-alaninamide | Calc'd 433.1, found 433.0 |
| 1-26 | 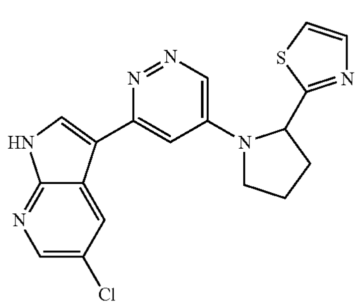 [SMILES: Clc1cnc2[nH]cc(-c3cc(N4CCCC4c4nccs4)cnn3)c2c1] | 5-chloro-3-{5-[2-(1,3-thiazol-2-yl)pyrrolidin-1-yl]pyridazin-3-yl}-1H-pyrrolo[2,3-b]pyridine | Calc'd 383.1, found 383.1 |

TABLE 5-continued

| Example Number | Structure | IUPAC Name | Exact Mass [M + H]+ |
|---|---|---|---|
| 1-27 | 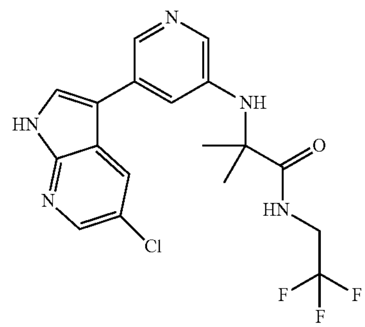 [SMILES: CC(C)(Nc1cncc(-c2c[nH]c3ncc(Cl)cc23)c1)C(=O)NCC(F)(F)F] | N~2~-[5-(5-chloro-1H-pyrrolo[2,3-b]pyridin-3-yl)pyridin-3-yl]-2-methyl-N-(2,2,2-trifluoroethyl)alaninamide | Calc'd 412.1, found 412.1 |
| 1-28 | 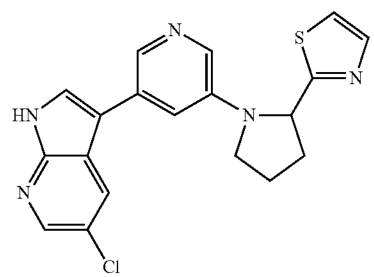 [SMILES: Clc1cnc2[nH]cc(-c3cncc(N4CCCC4c4nccs4)c3)c2c1] | 5-chloro-3-{5-[2-(1,3-thiazol-2-yl)pyrrolidin-1-yl]pyridin-3-yl}-1H-pyrrolo[2,3-b]pyridine | Calc'd 382.1, found 382.1 |
| 1-29 | 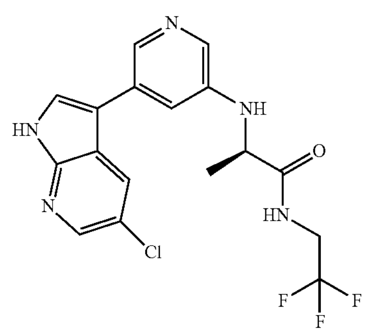 [SMILES: C[C@@H](Nc1cncc(-c2c[nH]c3ncc(Cl)cc23)c1)C(=O)NCC(F)(F)F] | N~2~-[5-(5-chloro-1H-pyrrolo[2,3-b]pyridin-3-yl)pyridin-3-yl]-N-(2,2,2-trifluoroethyl)-D-alaninamide | Calc'd 398.1, found 398.1 |
| 1-30 | 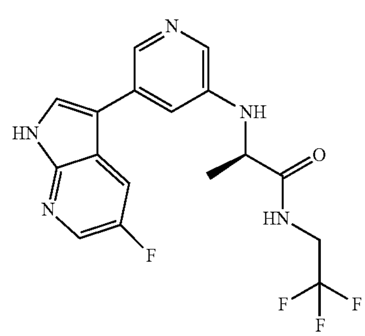 [SMILES: C[C@@H](Nc1cncc(-c2c[nH]c3ncc(F)cc23)c1)C(=O)NCC(F)(F)F] | N~2~-[5-(5-fluoro-1H-pyrrolo[2,3-b]pyridin-3-yl)pyridin-3-yl]-N-(2,2,2-trifluoroethyl)-D-alaninamide | Calc'd 382.1, found 382.0 |
| 1-31 | 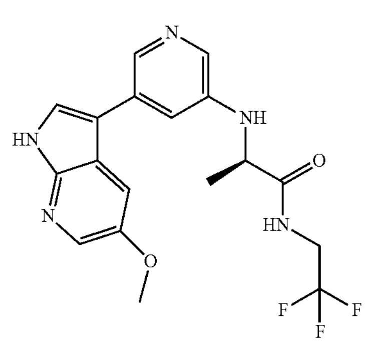 [SMILES: COc1cnc2[nH]cc(-c3cncc(N[C@H](C)C(=O)NCC(F)(F)F)c3)c2c1] | N~2~-[5-(5-methoxy-1H-pyrrolo[2,3-b]pyridin-3-yl)pyridin-3-yl]-N-(2,2,2-trifluoroethyl)-D-alaninamide | Calc'd 394.1, found 394.0 |

TABLE 5-continued

| Example Number | Structure | IUPAC Name | Exact Mass [M + H]+ |
|---|---|---|---|
| 1-32 | 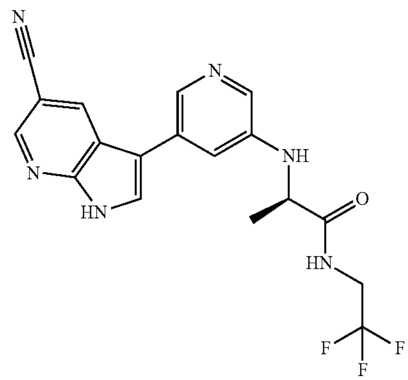 [SMILES: C[C@@H](Nc1cncc(-c2c[nH]c3ncc(C#N)cc23)c1)C(=O)NCC(F)(F)F] | N~2~-[5-(5-cyano-1H-pyrrolo[2,3-b]pyridin-3-yl)pyridin-3-yl]-N-(2,2,2-trifluoroethyl)-D-alaninamide | Calc'd 389.1, found 389.0 |
| 1-33 | 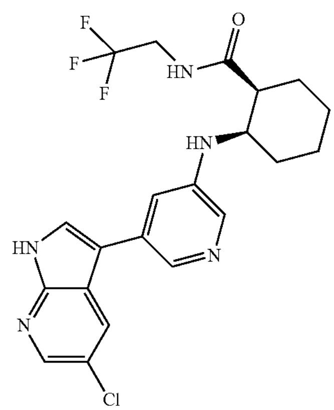 [SMILES: O=C(NCC(F)(F)F)[C@H]1CCCC[C@H]1Nc1cncc(-c2c[nH]c3ncc(Cl)cc23)c1] | (1S,2R)-2-{[5-(5-chloro-1H-pyrrolo[2,3-b]pyridin-3-yl)pyridin-3-yl]amino}-N-(2,2,2-trifluoroethyl)cyclohexanecarboxamide | Calc'd 452.1, found 452.1 |
| 1-34 | 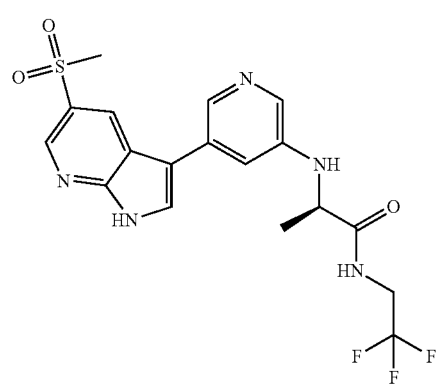 [SMILES: C[C@@H](Nc1cncc(-c2c[nH]c3ncc(S(C)(=O)=O)cc23)c1)C(=O)NCC(F)(F)F] | N~2~-{5-[5-(methylsulfonyl)-1H-pyrrolo[2,3-b]pyridin-3-yl]pyridin-3-yl}-N-(2,2,2-trifluoroethyl)-D-alaninamide | Calc'd 442.1, found 442.0 |
| 1-35 | 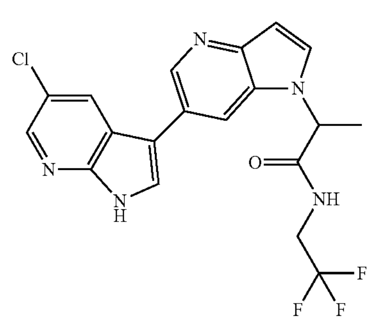 [SMILES: CC(C(=O)NCC(F)(F)F)n1ccc2ncc(-c3c[nH]c4ncc(Cl)cc34)cc21] | 2-[6-(5-chloro-1H-pyrrolo[2,3-b]pyridin-3-yl)-1H-pyrrolo[3,2-b]pyridin-1-yl]-N-(2,2,2-trifluoroethyl)propanamide | Calc'd 422.1, found 422.0 |

TABLE 5-continued

| Example Number | Structure | IUPAC Name | Exact Mass [M + H]+ |
|---|---|---|---|
| 1-36 | 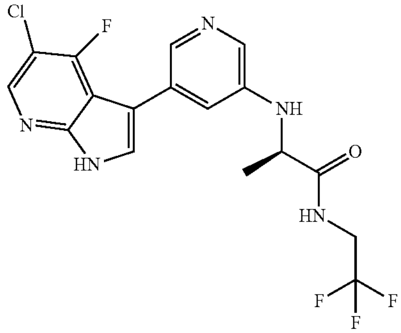 [SMILES: C[C@@H](Nc1cncc(-c2c[nH]c3ncc(Cl)c(F)c23)c1)C(=O)NCC(F)(F)F] | N~2~-[5-(5-chloro-4-fluoro-1H-pyrrolo[2,3-b]pyridin-3-yl)pyridin-3-yl]-N-(2,2,2-trifluoroethyl)-D-alaninamide | Calc'd 416.1, found 416.0 |
| 1-37 | 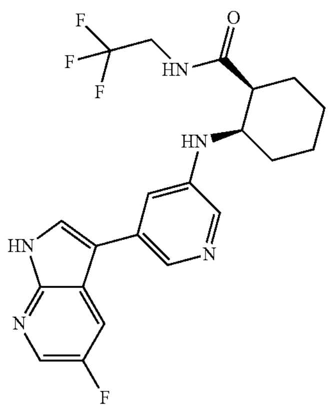 [SMILES: O=C(NCC(F)(F)F)[C@H]1CCCC[C@H]1Nc1cncc(-c2c[nH]c3ncc(F)cc23)c1] | (1S,2R)-2-{[5-(5-fluoro-1H-pyrrolo[2,3-b]pyridin-3-yl)pyridin-3-yl]amino}-N-(2,2,2-trifluoroethyl)cyclohexanecarboxamide | Calc'd 436.2, found 436.1 |
| 1-38 | 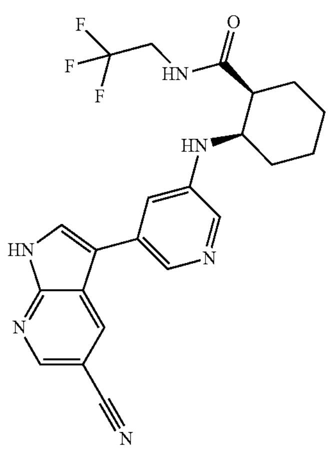 [SMILES: N#Cc1cnc2[nH]cc(-c3cncc(N[C@@H]4CCCC[C@@H]4C(=O)NCC(F)(F)F)c3)c2c1] | (1S,2R)-2-{[5-(5-cyano-1H-pyrrolo[2,3-b]pyridin-3-yl)pyridin-3-yl]amino}-N-(2,2,2-trifluoroethyl)cyclohexanecarboxamide | Calc'd 443.2, found 443.1 |
| 1-39 | 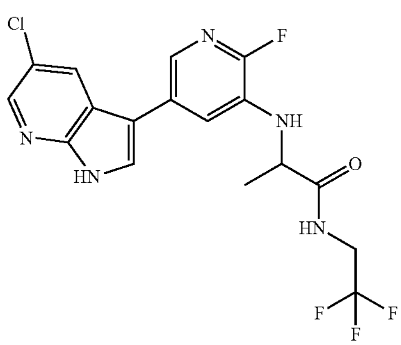 [SMILES: CC(Nc1cc(-c2c[nH]c3ncc(Cl)cc23)cnc1F)C(=O)NCC(F)(F)F] | N~2~-[5-(5-chloro-1H-pyrrolo[2,3-b]pyridin-3-yl)-2-fluoropyridin-3-yl]-N-(2,2,2-trifluoroethyl)alaninamide | Calc'd 416.1, found 416.0 |

TABLE 5-continued

| Example Number | Structure | IUPAC Name | Exact Mass [M + H]+ |
|---|---|---|---|
| 1-40 | 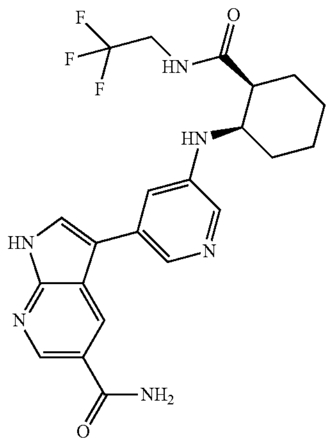 [SMILES: NC(=O)c1cnc2[nH]cc(-c3cncc(N[C@@H]4CCCC[C@@H]4C(=O)NCC(F)(F)F)c3)c2c1] | 3-[5-({(1R,2S)-2-[(2,2,2-trifluoroethyl)carbamoyl]cyclohexyl}amino)pyridin-3-yl]-1H-pyrrolo[2,3-b]pyridine-5-carboxamide | Calc'd 461.2, found 461.2 |
| 1-41 | 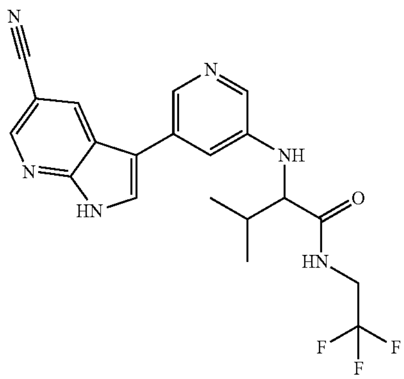 [SMILES: CC(C)C(Nc1cncc(-c2c[nH]c3ncc(C#N)cc23)c1)C(=O)NCC(F)(F)F] | N~2~-[5-(5-cyano-1H-pyrrolo[2,3-b]pyridin-3-yl)pyridin-3-yl]-N-(2,2,2-trifluoroethyl)valinamide | Calc'd 417.2, found 417.2 |
| 1-42 | 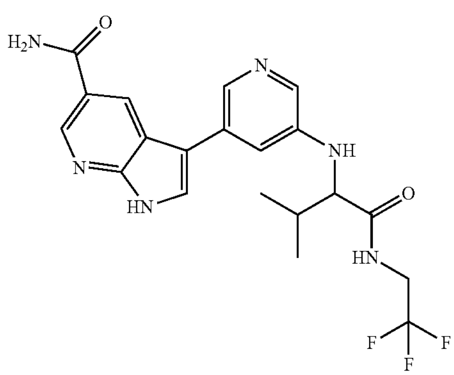 [SMILES: CC(C)C(Nc1cncc(-c2c[nH]c3ncc(C(N)=O)cc23)c1)C(=O)NCC(F)(F)F] | 3-[5-({2-methyl-1-[(2,2,2-trifluoroethyl)carbamoyl]propyl}amino)pridin-3-yl]-1H-pyrrolo[2,3-b]pyridine-5-carboxamide | Calc'd 435.2, found 435.2 |
| 1-43 | 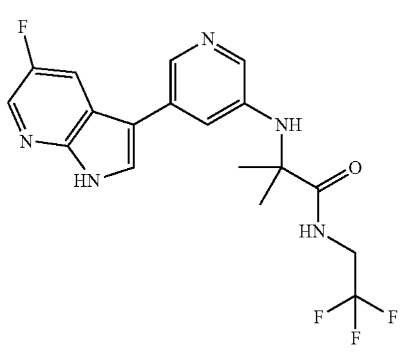 [SMILES: CC(C)(Nc1cncc(-c2c[nH]c3ncc(F)cc23)c1)C(=O)NCC(F)(F)F] | N~2~-[5-(5-fluoro-1H-pyrrolo[2,3-b]pyridin-3-yl)pyridin-3-yl]-2-methyl-N-(2,2,2-trifluoroethyl)alaninamide | Calc'd 396.1, found 396.1 |

TABLE 5-continued

| Example Number | Structure | IUPAC Name | Exact Mass [M + H]+ |
|---|---|---|---|
| 1-44 | 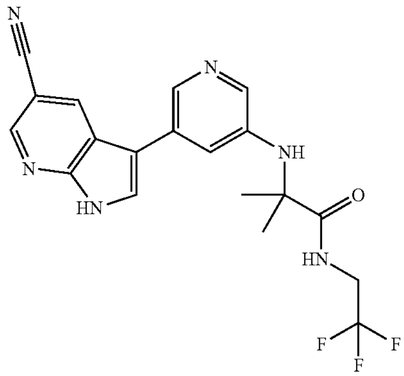 [SMILES: CC(C)(Nc1cncc(-c2c[nH]c3ncc(C#N)cc23)c1)C(=O)NCC(F)(F)F] | N~2~-[5-(5-cyano-1H-pyrrolo[2,3-b]pyridin-3-yl)pyridin-3-yl]-2-methyl-N-(2,2,2-trifluoroethyl)alaninamide | Calc'd 403.1, found 403.1 |
| 1-45 | 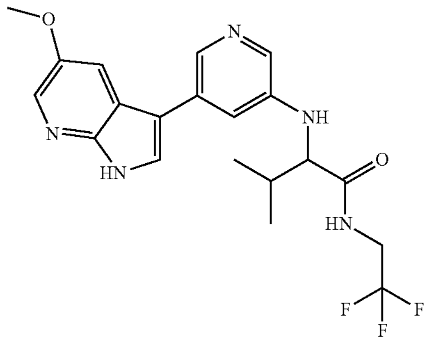 [SMILES: COc1cnc2[nH]cc(-c3cncc(NC(C(=O)NCC(F)(F)F)C(C)C)c3)c2c1] | N~2~-[5-(5-methoxy-1H-pyrrolo[2,3-b]pyridin-3-yl)pyridin-3-yl]-N-(2,2,2-trifluoroethyl)valinamide | Calc'd 422.2, found 422.2 |
| 1-46 | 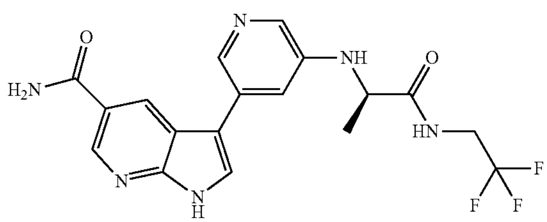 [SMILES: C[C@@H](Nc1cncc(-c2c[nH]c3ncc(C(N)=O)cc23)c1)C(=O)NCC(F)(F)F] | 3-[5-({(1R)-1-methyl-2-oxo-2-[(2,2,2-trifluoroethyl)amino]ethyl}amino)pyridin-3-yl]-1H-pyrrolo[2,3-b]pyridine-5-carboxamide | Calc'd 407.1, found 407.0 |
| 1-47 | 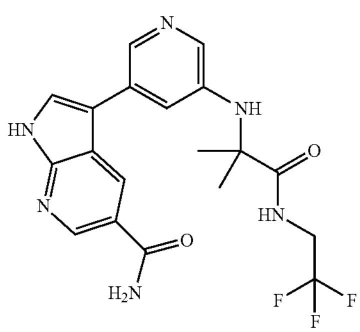 [SMILES: CC(C)(Nc1cncc(-c2c[nH]c3ncc(C(N)=O)cc23)c1)C(=O)NCC(F)(F)F] | 3-[5-({1,1-dimethyl-2-oxo-2-[(2,2,2-trifluoroethyl)amino]ethyl}amino)pyridin-3-yl]-1H-pyrrolo[2,3-b]pyridine-5-carboxamide | Calc'd 421.2, found 421.2 |
| 1-48 | 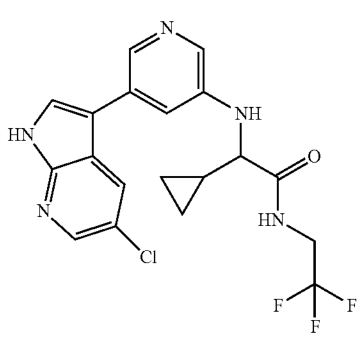 [SMILES: O=C(NCC(F)(F)F)C(Nc1cncc(-c2c[nH]c3ncc(Cl)cc23)c1)C1CC1] | 2-{[5-(5-chloro-1H-pyrrolo[2,3-b]pyridin-3-yl)pyridin-3-yl]amino}-2-cyclopropyl-N-(2,2,2-trifluoroethyl)acetamide | Calc'd 424.1, found 424.1 |

TABLE 5-continued

| Example Number | Structure | IUPAC Name | Exact Mass [M + H]+ |
|---|---|---|---|
| 1-49 | 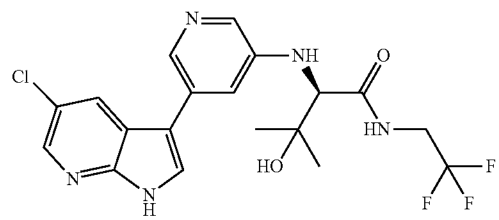 [SMILES: CC(C)(O)[C@@H](Nc1cncc(-c2c[nH]c3ncc(Cl)cc23)c1)C(=O)NCC(F)(F)F] | N~2~-[5-(5-chloro-1H-pyrrolo[2,3-b]pyridin-3-yl)pyridin-3-yl]-3-hydroxy-N-(2,2,2-trifluoroethyl)-D-valinamide | Calc'd 442.1, found 441.1 |
| 1-50 | 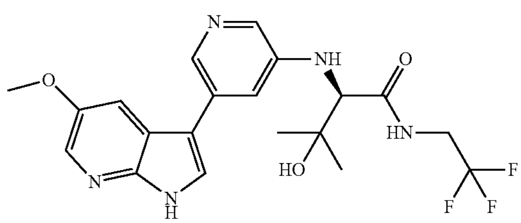 [SMILES: COc1cnc2[nH]cc(-c3cncc(N[C@@H](C(=O)NCC(F)(F)F)C(C)(C)O)c3)c2c1] | 3-hydroxy-N~2~-[5-(5-methoxy-1H-pyrrolo[2,3-b]pyridin-3-yl)pyridin-3-yl]-N-(2,2,2-trifluoroethyl)-D-valinamide | Calc'd 438.2, found 438.1 |
| 1-51 | 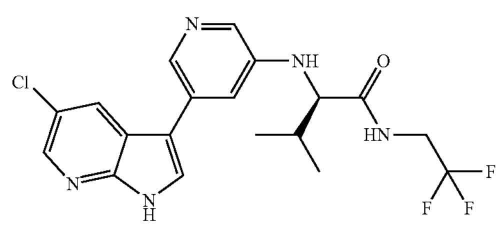 [SMILES: CC(C)[C@@H](Nc1cncc(-c2c[nH]c3ncc(Cl)cc23)c1)C(=O)NCC(F)(F)F] | N~2~-[5-(5-chloro-1H-pyrrolo[2,3-b]pyridin-3-yl)pyridin-3-yl]-N-(2,2,2-trifluoroethyl)-D-valinamide | Calc'd 426.1, found 426.1 |
| 1-52 | 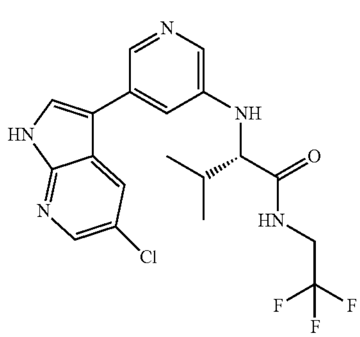 [SMILES: CC(C)[C@H](Nc1cncc(-c2c[nH]c3ncc(Cl)cc23)c1)C(=O)NCC(F)(F)F] | N-18 2~-[5-(5-chloro-1H-pyrrolo[2,3-b]pyridin-3-yl)pyridin-3-yl]-N-(2,2,2-trifluoroethyl)-L-valinamide | Calc'd 426.1, found 426.1 |

Examples generated via General Scheme 2:

Example 2-1

2-{[5-(5-hydroxy-1H-pyrrolo[2,3-b]pyridin-3-yl)pyridin-3-yl]amino}-3-methyl-N-(2,2,2-trifluoroethyl)butanamide (2-1)

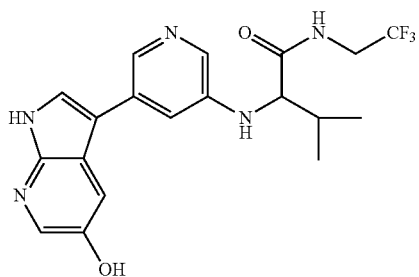

2-1

Step 1 2-(5-(5-chloro-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide

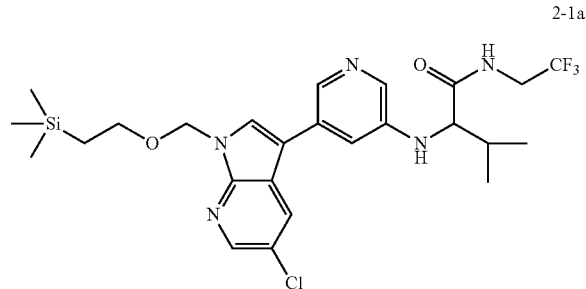

2-1a

To a nitrogen gas purged mixture of 5-chloro-3-(4,4,5,5-tetramethyl-1,3,2-dioxaborolan-2-yl)-1-((2-(trimethylsilyl)ethoxy)methyl)-1H-pyrrolo[2,3-b]pyridine (231 mg, 0.565 mmol), (R)-2-(5-bromopyridin-3-ylamino)-3-methyl-N-(2,2,2-trifluoroethyl)butanamide (200 mg, 0.565 mmol), and Na$_2$CO$_3$ (847 μl, 1.694 mmol) in DME (3765 μl) was added Tetrakis (131 mg, 0.113 mmol). The reaction mixture was heated at 100° C. in a sealed microwave vessel for 1 h. Water (10 mL) was added and the mixture was extracted with ethyl acetate (2×20 mL). The combined organic extracts were dried with sodium sulfate, and concentrated under reduced pressure. Purification of the residue on silica (0-5% methanol/ethyl acetate, 25 gm silica) to give 232 mg foam, (2-1a). LRMS (ESI) m/z 556.2 [(M+H)$^+$; calcd for C25H33ClF3N5O2Si: 556.1].

Step 2 2-(5-(5-hydroxy-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide (2-1b)

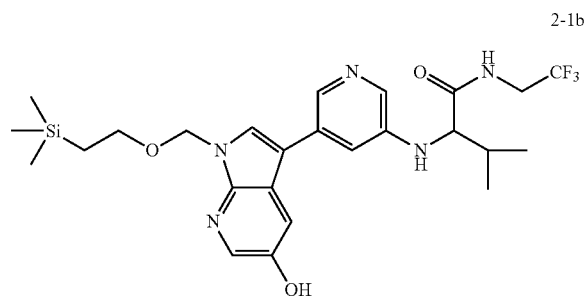 [SMILES: CC(C)C(Nc1cncc(-c2cn(COCC[Si](C)(C)C)c3ncc(Cl)cc23)c1)C(=O)NCC(F)(F)F]

2-1b

To a nitrogen gas purged microwave vial of 2-(5-(5-chloro-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide 2-1a (800 mg, 1.439 mmol), 2-DI-T-BUTYLPHOSPHINO-3,4,5,6-TETRAMETHYL-2',4',6'-TRI-I-PROPYLBIPHENYL (55.3 mg, 0.115 mmol) and Pd2 dba3 (26.3 mg, 0.029 mmol) in Dioxane (6 ml) was added 1 M KOH (4.32 ml, 4.32 mmol). The reaction mixture was sealed and heated in an oil bath at 100° C. for 18 h. The reaction was cooled, diluted with brine and product extracted with ethyl acetate. The organic extract was dried over sodium sulfate, filtered and concentrated to an oil. The oil was diluted with diethyl ether (18 ml) and sonicated. The resulting solid was filtered and washed with ether to give 720 mg white solid, 2-1b.
LRMS (ESI) m/z 538.2 [(M+H)$^+$; calcd for C25H34F3N5O3Si: 538.2].

Step 3 2-{[5-(5-hydroxy-1H-pyrrolo[2,3-b]pyridin-3-yl)pyridin-3-yl]amino}-3-methyl-N-(2,2,2-trifluoroethyl)butanamide (2-1)

The title compound was prepared from 2-(5-(5-hydroxy-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide 2-1b in a manner similar to that used in the preparation of Examples 1-1 through 1-6. LRMS (ESI) m/z 408.2 [(M+H)$^+$; calcd for C19H20F3N5O2: 408.2].

Example 2-2

2-{[5-(5-hydroxy-1H-pyrrolo[2,3-b]pyridin-3-yl)pyridin-3-yl]amino}-3-methyl-N-(2,2,2-trifluoroethyl)butanamide (2-2)

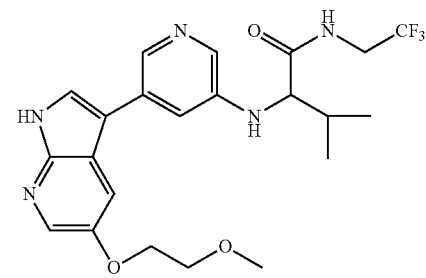

2-2

PS-triphenylphosphine (143 mg, 0.270 mmol) and 2-{[5-(5-hydroxy-1H-pyrrolo[2,3-b]pyridin-3-yl)pyridin-3-yl]amino}-3-methyl-N-(2,2,2-trifluoroethyl)butanamide 2-1 (50 mg, 0.123 mmol) were combined in THF (1227 μl) and stirred for 5 minutes at RT. To this mixture was added a solution of di-tert-butyl azodicarboxylate (45.2 mg, 0.196 mmol) in THF (100 ul) and the reaction allowed to stir for 30 min. 2-methoxyethanol (10.65 μl, 0.135 mmol) was then added and the mixture allowed to stir for 2 hr. The reaction was quenched with a 1/1 solution of trifluoroacetic acid and dichloromethane (0.5 mL) followed by water (100 uL). The reaction was allowed to stir for 30 minutes, filtered and the filtrate concentrated to an oil. The oil was dissolved with DMSO (1 ml) purified by reverse phase chromatography to give upon lyophillization the desired product 2-2 (20 mg) as a foam. LRMS (ESI) m/z 466.2 [(M+H)$^+$; calcd for C22H26F3N5O3: 466.2].

The following examples, 2-3 through 2-18 as shown in Table 6, were prepared in an analogous manner of that described above using materials that are commercially available or known, or that can be prepared using procedures known in the art or by generally following procedures described herein for various intermediates.

TABLE 6

| Ex. No. | Chemical Structure | IUPAC Name | Exact Mass [M + H]+ |
|---|---|---|---|
| 2-3 | 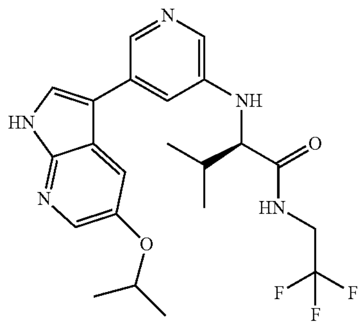 [SMILES: CC(C)Oc1cnc2[nH]cc(-c3cncc(N[C@@H](C(=O)NCC(F)(F)F)C(C)C)c3)c2c1] | N~2~-{5-[5-(1-methylethoxy)-1H-pyrrolo[2,3-b]pyridin-3-yl]pyridin-3-yl}-N-(2,2,2-trifluoroethyl)-D-valinamide | Calc'd 450.2, found 450.2 |
| 2-4 | 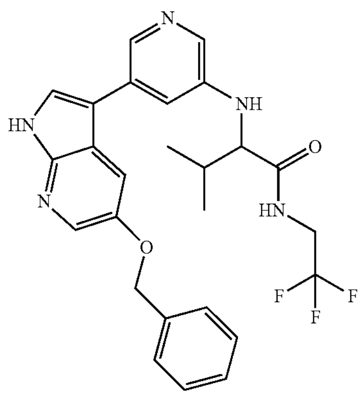 [SMILES: CC(C)C(Nc1cncc(-c2c[nH]c3ncc(OCc4ccccc4)cc23)c1)C(=O)NCC(F)(F)F] | N~2~-{5-[5-(benzyloxy)-1H-pyrrolo[2,3-b]pyridin-3-yl]pyridin-3-yl}-N-(2,2,2-trifluoroethyl)valinamide | Calc'd 498.2, found 498.2 |
| 2-5 | 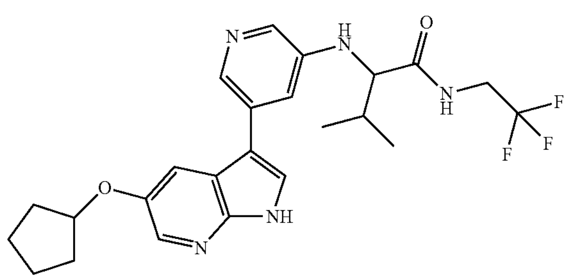 [SMILES: CC(C)C(Nc1cncc(-c2c[nH]c3ncc(OC4CCCC4)cc23)c1)C(=O)NCC(F)(F)F] | N~2~-{5-[5-(cyclopentyloxy)-1H-pyrrolo[2,3-b]pyridin-3-yl]pyridin-3-yl}-N-(2,2,2-trifluoroethyl)valinamide | Calc'd 476.2, found 476.2 |
| 2-6 | 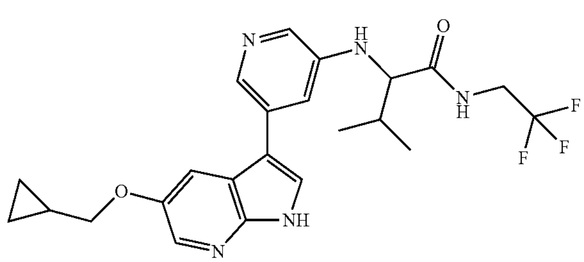 [SMILES: CC(C)C(Nc1cncc(-c2c[nH]c3ncc(OCC4CC4)cc23)c1)C(=O)NCC(F)(F)F] | N~2~-{5-[5-(cyclopropylmethoxy)-1H-pyrrolo[2,3-b]pyridin-3-yl]pyridin-3-yl}-N-(2,2,2-trifluoroethyl)valinamide | Calc'd 462.2, found 462.2 |

TABLE 6-continued

| Ex. No. | Chemical Structure | IUPAC Name | Exact Mass [M + H]+ |
|---|---|---|---|
| 2-7 | 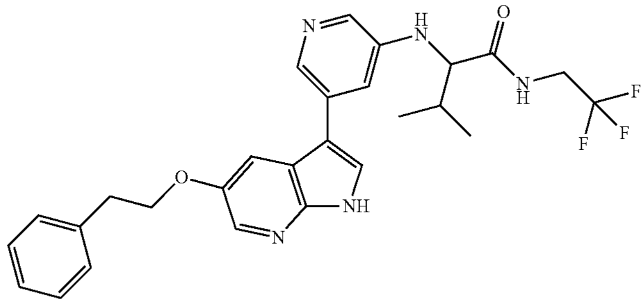 [SMILES: CC(C)C(Nc1cncc(-c2c[nH]c3ncc(OCCc4ccccc4)cc23)c1)C(=O)NCC(F)(F)F] | N~2~-{5-[5-(2-phenylethoxy)-1H-pyrrolo[2,3-b]pyridin-3-yl]pyridin-3-yl}-N-(2,2,2-trifluoroethyl)valinamide | Calc'd 512.2, found 512.2 |
| 2-8 | 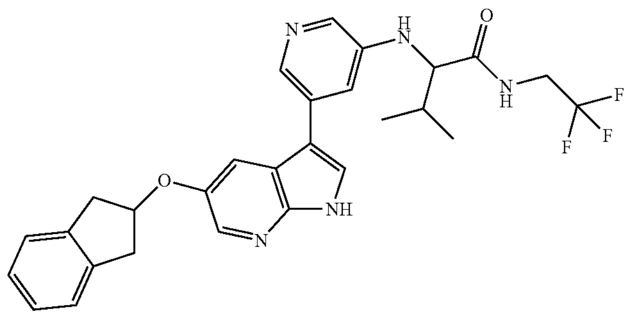 [SMILES: CC(C)C(Nc1cncc(-c2c[nH]c3ncc(OC4Cc5ccccc5C4)cc23)c1)C(=O)NCC(F)(F)F] | N~2~-{5-[5-(2,3-dihydro-1H-inden-2-yloxy)-1H-pyrrolo[2,3-b]pyridin-3-yl]pyridin-3-yl}-N-(2,2,2-trifluoroethyl)valinamide | Calc'd 524.2, found 524.2 |
| 2-9 | 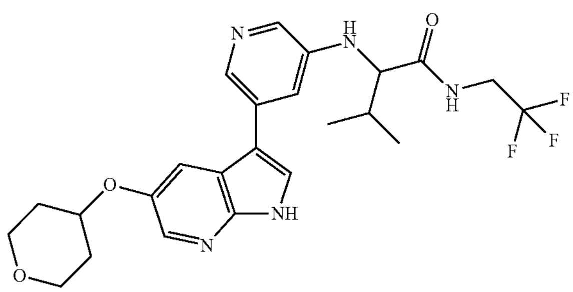 [SMILES: CC(C)C(Nc1cncc(-c2c[nH]c3ncc(OC4CCOCC4)cc23)c1)C(=O)NCC(F)(F)F] | N~2~-{5-[5-(tetrahydro-2H-pyran-4-yloxy)-1H-pyrrolo[2,3-b]pyridin-3-yl]pyridin-3-yl}-N-(2,2,2-trifluoroethyl)valinamide | Calc'd 492.2, found 492.2 |
| 2-10 | 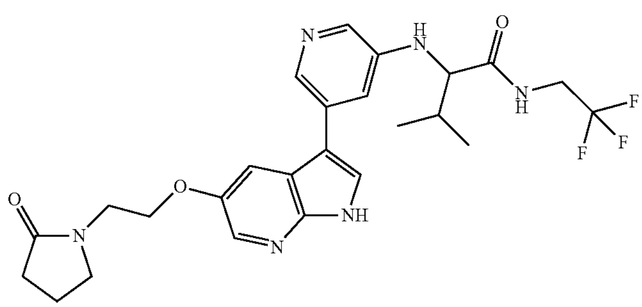 [SMILES: CC(C)C(Nc1cncc(-c2c[nH]c3ncc(OCCN4CCCC4=O)cc23)c1)C(=O)NCC(F)(F)F] | N~2~-(5-{5-[2-(2-oxopyrrolidin-1-yl)ethoxy]-1H-pyrrolo[2,3-b]pyridin-3-yl}pyridin-3-yl)-N-(2,2,2-trifluoroethyl)valinamide | Calc'd 519.2, found 519.2 |
| 2-11 | 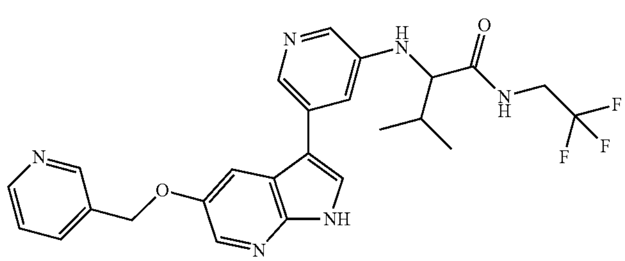 [SMILES: CC(C)C(Nc1cncc(-c2c[nH]c3ncc(OCc4cccnc4)cc23)c1)C(=O)NCC(F)(F)F] | N~2~-{5-[5-(pyridin-3-ylmethoxy)-1H-pyrrolo[2,3-b]pyridin-3-yl]pyridin-3-yl}-N-(2,2,2-trifluoroethyl)valinamide | Calc'd 499.2, found 499.2 |

TABLE 6-continued

| Ex. No. | Chemical Structure | IUPAC Name | Exact Mass [M + H]+ |
|---|---|---|---|
| 2-12 | 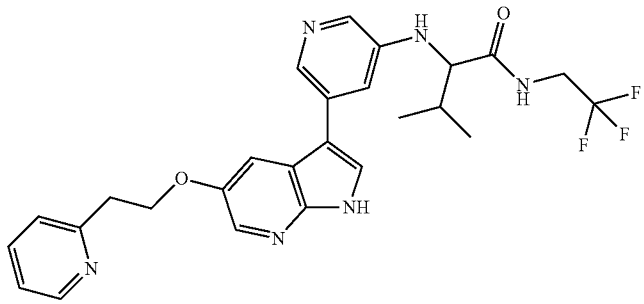 [SMILES: CC(C)C(Nc1cncc(-c2c[nH]c3ncc(OCCc4ccccn4)cc23)c1)C(=O)NCC(F)(F)F] | N~2~-{5-[5-(2-pyridin-2-ylethoxy)-1H-pyrrolo[2,3-b]pyridin-3-yl]pyridin-3-yl}-N-(2,2,2-trifluoroethyl)valinamide | 513.2, found 513.2 |
| 2-13 | 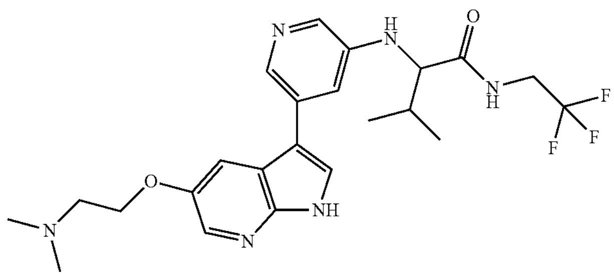 [SMILES: CC(C)C(Nc1cncc(-c2c[nH]c3ncc(OCCN(C)C)cc23)c1)C(=O)NCC(F)(F)F] | N~2~-(5-{5-[2-(dimethylamino)ethoxy]-1H-pyrrolo[2,3-b]pyridin-3-yl}pyridin-3-yl)-N-(2,2,2-trifluoroethyl)valinamide | Calc'd 479.2, found 479.2 |
| 2-14 | 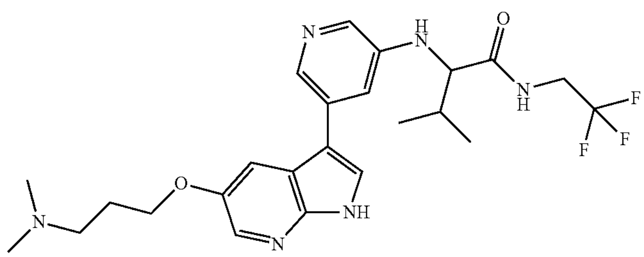 [SMILES: CC(C)C(Nc1cncc(-c2c[nH]c3ncc(OCCCN(C)C)cc23)c1)C(=O)NCC(F)(F)F] | N~2~-(5-{5-[3-(dimethylamino)propoxy]-1H-pyrrolo[2,3-b]pyridin-3-yl}pyridin-3-yl)-N-(2,2,2-trifluoroethyl)valinamide | Calc'd 493.3, found 493.2 |
| 2-15 | 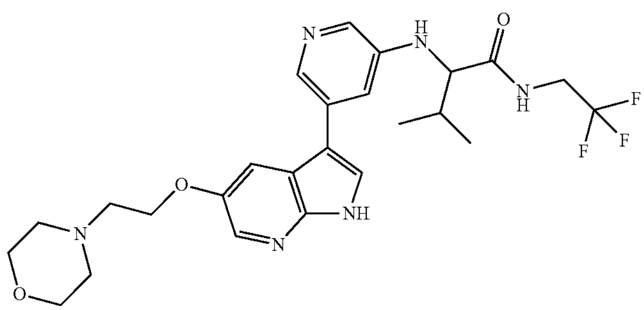 [SMILES: CC(C)C(Nc1cncc(-c2c[nH]c3ncc(OCCN4CCOCC4)cc23)c1)C(=O)NCC(F)(F)F] | N~2~-{5-[5-(2-morpholin-4-ylethoxy)-1H-pyrrolo[2,3-b]pyridin-3-yl]pyridin-3-yl}-N-(2,2,2-trifluoroethyl)valinamide | Calc'd 521.2, found 521.3 |
| 2-16 | 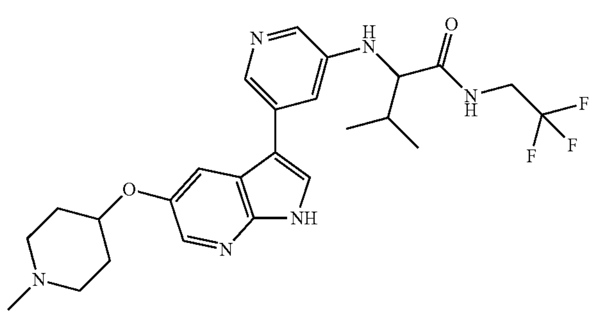 [SMILES: CC(C)C(Nc1cncc(-c2c[nH]c3ncc(OC4CCN(C)CC4)cc23)c1)C(=O)NCC(F)(F)F] | N~2~-(5-{5-[(1-methylpiperidin-4-yl)oxy]-1H-pyrrolo[2,3-b]pridin-3-yl}pyridin-3-yl)-N-(2,2,2-trifluoroethyl)valinamide | Calc'd 505.3, found 505.3 |

TABLE 6-continued

| Ex. No. | Chemical Structure | IUPAC Name | Exact Mass [M + H]+ |
|---|---|---|---|
| 2-17 | 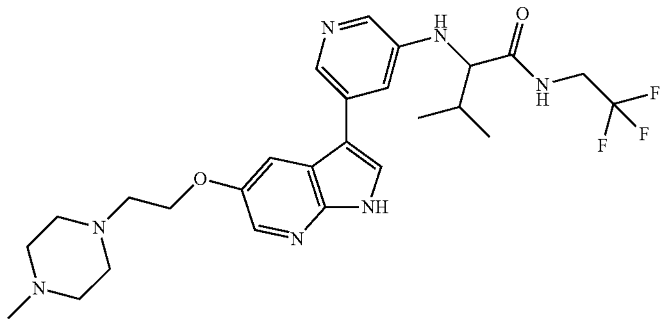 [SMILES: CC(C)C(Nc1cncc(-c2c[nH]c3ncc(OCCN4CCN(C)CC4)cc23)c1)C(=O)NCC(F)(F)F] | N~2~-(5-{5-[2-(4-methylpiperazin-1-yl)ethoxy]-1H-pyrrolo[2,3-b]pyridin-3-yl}pyridin-3-yl)-N-(2,2,2-trifluoroethyl)valinamide | Calc'd 534.3, found 534.3 |
| 2-18 | 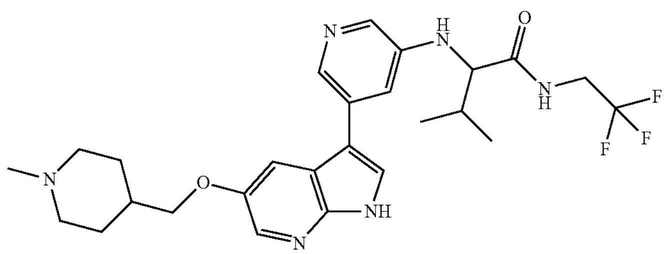 [SMILES: CC(C)C(Nc1cncc(-c2c[nH]c3ncc(OCC4CCN(C)CC4)cc23)c1)C(=O)NCC(F)(F)F] | N~2~-(5-{5-[(1-methylpiperidin-4-yl)methoxy]-1H-pyrrolo[2,3-b]ppidin-3-yl}pyridin-3-yl)-N-(2,2,2-trifluoroethyl)valinamide | Calc'd 519.3, found 519.3 |

Examples generated via General Scheme 3:

Example 3-1

(R)—N,N-dimethyl-3-(5-(3-methyl-1-oxo-1-(2,2,2-trifluoroethylamino)butan-2-ylamino)pyridin-3-yl)-1H-pyrrolo[2,3-b]pyridine-5-carboxamide (3-1)

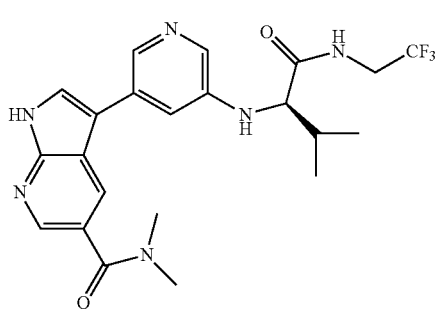

Step 1 (R)-ethyl 3-(5-(3-methyl-1-oxo-1-(2,2,2-trifluoroethylamino)butan-2-ylamino)pyridin-3-yl)-1H-pyrrolo[2,3-b]pyridine-5-carboxylate (3-1a)

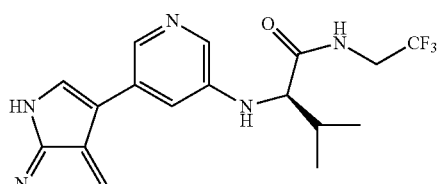

3-1a (R)-ethyl 3-(5-(3-methyl-1-oxo-1-(2,2,2-trifluoroethylamino)butan-2-ylamino)pyridin-3-yl)-1H-pyrrolo[2,3-b]pyridine-5-carboxylate 3-1a was prepared in a manner similar to that utilized for the preparation of 2-1a utilizing of 5-ethoxy-3-(4,4,5,5-tetramethyl-1,3,2-dioxaborolan-2-yl)-1-((2-(trimethylsilyl)ethoxy)methyl)-1H-pyrrolo[2,3-b]pyridine.

LRMS (ESI) m/z 464.2 [(M+H)⁺; calcd for C₂₂H₂₄F₃N₅O₃: 564.2

Step 2 (R)-3-(5-(3-methyl-1-oxo-1-(2,2,2-trifluoroethylamino)butan-2-ylamino)pyridin-3-yl)-1H-pyrrolo[2,3-b]pyridine-5-carboxylic acid (3-1b)

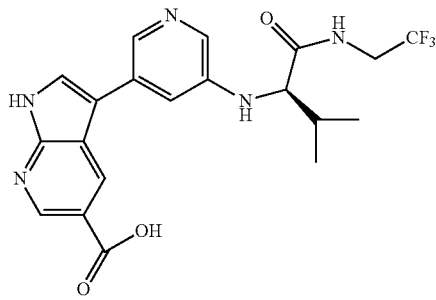 [SMILES: CC(C)[C@@H](Nc1cncc(-c2c[nH]c3ncc(C(=O)O)cc23)c1)C(=O)NCC(F)(F)F]

To ethyl 3-(5-(3-methyl-1-oxo-1-(2,2,2-trifluoroethylamino)butan-2-ylamino)pyridin-3-yl)-1H-pyrrolo[2,3-b]pyridine-5-carboxylate 3-1a (0.775 g, 1.724 mmol) in methanol (18 mL) was added sodium hydroxide (5.17 ml, 5.17 mmol). The mixture was heated at 50° C. for 18 hrs. The reaction was concentrated in vacuo and aqueous washed with diethyl ether. The aqueous extract was concentrated and 1N HCl added until a precipitate forms (~pH6). The solid was filtered to give the desired product. 0.467 g. LRMS (ESI) m/z 436.2 [(M+H)⁺; calcd for C20H20F3N5O3: 436.2.

Step 3 (R)—N,N-dimethyl-3-(5-(3-methyl-1-oxo-1-(2,2,2-trifluoroethylamino)butan-2-ylamino)pyridin-3-yl)-1H-pyrrolo[2,3-b]pyridine-5-carboxamide (3-1)

To a 0° C. solution of 2M dimethylamine/THF (58 uL, 0.115 mmol), 3-(5-(3-methyl-1-oxo-1-(2,2,2-trifluoroethylamino)butan-2-ylamino)pyridin-3-yl)-1H-pyrrolo[2,3-b]pyridine-5-carboxylic acid 3-1b (25 mg, 0.057 mmol) and DIPEA (0.025 ml, 0.144 mmol) in DMF (0.7 ml) was slowly added 2,4,6-tripropyl-1,3,5,2,4,6-trioxatriphosphorinane-2,4,6-trioxide (0.078 ml, 0.115 mmol). The reaction was allowed to warm to room temperature and stir 18 hr. PyBOP (59.8 mg, 0.115 mmol) was then added and let stir 18 hr. The reaction was diluted with DMF (0.7 mL), filtered, and purified by reverse-phase HPLC. Lyophilization of pure fractions gave the title compound as a solid. LRMS (ESI) m/z 463.2 [(M+H)⁺; calcd for C22H25F3N6O2: 463.2].

The following examples 3-2 through 3-15 found in Table 7 were prepared in an analogous manner of that described above using materials that are commercially available or known, or that can be prepared using procedures known in the art or by generally following procedures described herein for various intermediates.

TABLE 7

| Ex. No. | Structure | IUPAC Name | Exact Mass [M + H]+ |
|---|---|---|---|
| 3-2 | 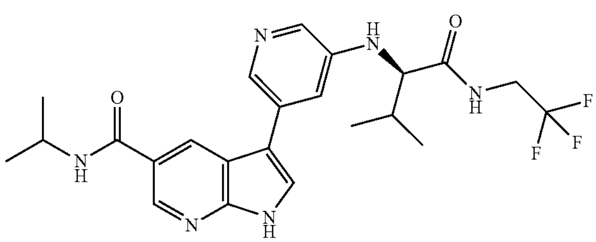 [SMILES: CC(C)NC(=O)c1cnc2[nH]cc(-c3cncc(N[C@@H](C(=O)NCC(F)(F)F)C(C)C)c3)c2c1] | N-(1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 477.2, found 477.2 |
| 3-3 | 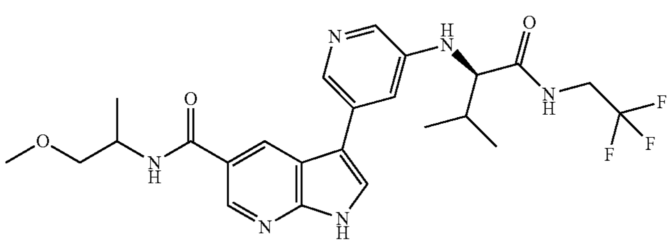 [SMILES: COCC(C)NC(=O)c1cnc2[nH]cc(-c3cncc(N[C@@H](C(=O)NCC(F)(F)F)C(C)C)c3)c2c1] | N-(2-methoxy-1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 507.2, found 507.2 |
| 3-4 | 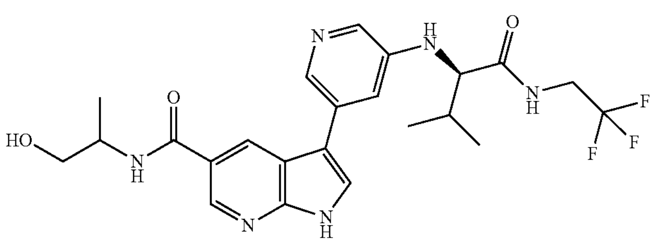 [SMILES: CC(CO)NC(=O)c1cnc2[nH]cc(-c3cncc(N[C@@H](C(=O)NCC(F)(F)F)C(C)C)c3)c2c1] | N-(2-hydroxy-1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 493.2, found 493.2 |

TABLE 7-continued

| Ex. No. | Structure | IUPAC Name | Exact Mass [M + H]+ |
|---|---|---|---|
| 3-5 | 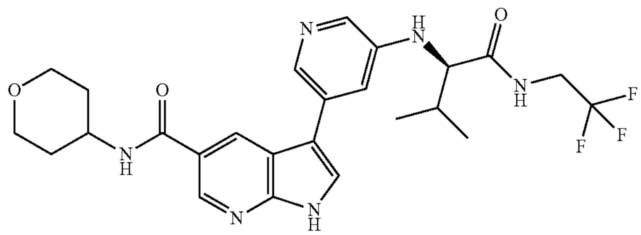 [SMILES: CC(C)[C@@H](Nc1cncc(-c2c[nH]c3ncc(C(=O)NC4CCOCC4)cc23)c1)C(=O)NCC(F)(F)F] | 3-[5-({(1R)-2-methyl-1-[(2,2,2-trifluoroethyl)carbamoyl]propyl}amino)pyridin-3-yl]-N-(tetrahydro-2H-pyran-4-yl)-1H-pyrrolo[2,3-b]pyridine-5-carboxamide | Calc'd 519.2, found 519.2 |
| 3-6 | 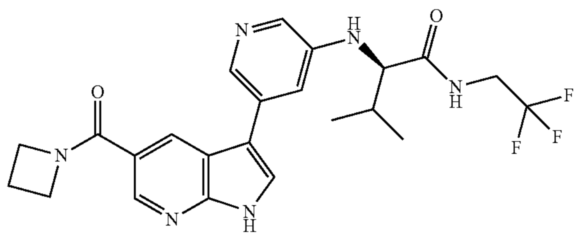 [SMILES: CC(C)[C@@H](Nc1cncc(-c2c[nH]c3ncc(C(=O)N4CCC4)cc23)c1)C(=O)NCC(F)(F)F] | N~2~-{5-[5-(azetidin-1-ylcarbonyl)-1H-pyrrolo[2,3-b]pyridin-3-yl]pyridin-3-yl}-N-(2,2,2-trifluoroethyl)-D-valinamide | Calc'd 475.2, found 475.2 |
| 3-7 | 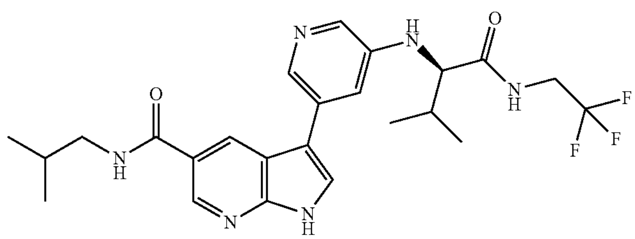 [SMILES: CC(C)CNC(=O)c1cnc2[nH]cc(-c3cncc(N[C@@H](C(=O)NCC(F)(F)F)C(C)C)c3)c2c1] | N-(2-methylpropyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 491.2, found 491.2 |
| 3-8 | 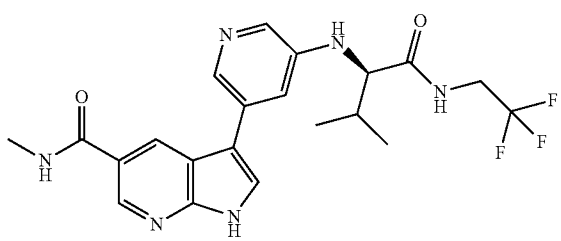 [SMILES: CNC(=O)c1cnc2[nH]cc(-c3cncc(N[C@@H](C(=O)NCC(F)(F)F)C(C)C)c3)c2c1] | N-methyl-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 449.2, found 449.2 |
| 3-9 | 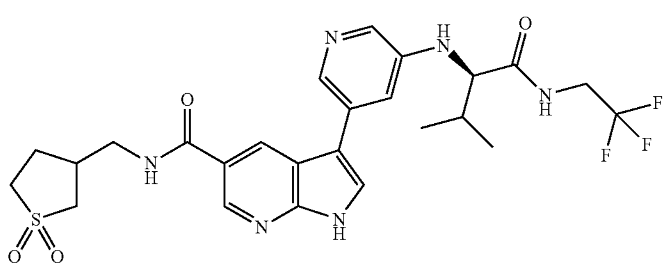 [SMILES: CC(C)[C@@H](Nc1cncc(-c2c[nH]c3ncc(C(=O)NCC4CCS(=O)(=O)C4)cc23)c1)C(=O)NCC(F)(F)F] | N-[(1,1-dioxidotetrahydrothiophen-3-yl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 567.2, found 567.2 |
| 3-10 | 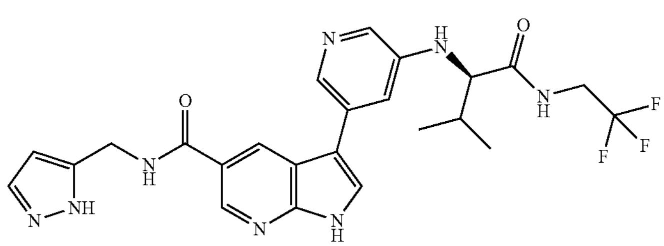 [SMILES: CC(C)[C@@H](Nc1cncc(-c2c[nH]c3ncc(C(=O)NCc4ccn[nH]4)cc23)c1)C(=O)NCC(F)(F)F] | 3-[5-({(1R)-2-methyl-1-[(2,2,2-trifluoroethyl)carbamoyl]propyl}amino)pyridin-3-yl]-N-(1H-pyrazol-5-ylmethyl)-1H-pyrrolo[2,3-b]pyridine-5-carboxamide | Calc'd 515.2, found 515.2 |

TABLE 7-continued

| Ex. No. | Structure | IUPAC Name | Exact Mass [M + H]+ |
|---|---|---|---|
| 3-11 | 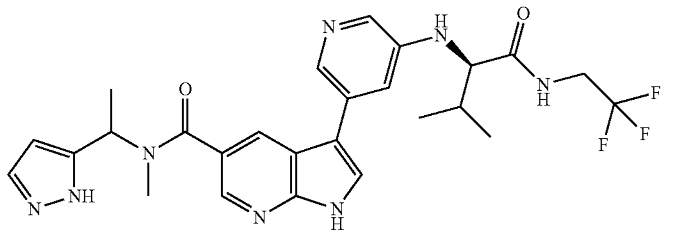 [SMILES: CC(C)[C@@H](Nc1cncc(-c2c[nH]c3ncc(C(=O)N(C)C(C)c4ccn[nH]4)cc23)c1)C(=O)NCC(F)(F)F] | N-methyl-3-[5-({(1R)-2-methyl-1-[(2,2,2-trifluoroethyl)carbamoyl]propyl}amino)pyridin-3-yl]-N-[1-(1H-pyrazol-5-yl)ethyl]-1H-pyrrolo[23-b]pyridine-5-carboxamide | Calc'd 543.2, found 543.3 |
| 3-12 | 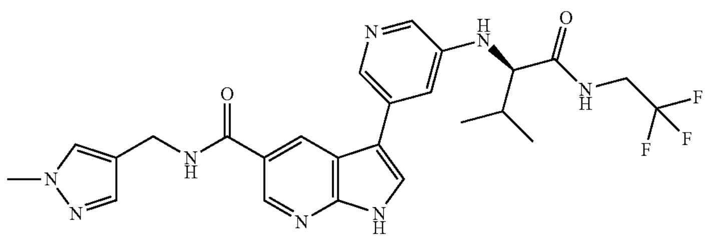 [SMILES: CC(C)[C@@H](Nc1cncc(-c2c[nH]c3ncc(C(=O)NCc4cnn(C)c4)cc23)c1)C(=O)NCC(F)(F)F] | N-[(1-methyl-1H-pyrazol-4-yl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 529.2, found 529.5 |
| 3-13 | 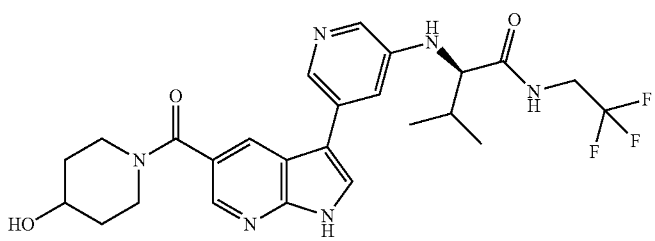 [SMILES: CC(C)[C@@H](Nc1cncc(-c2c[nH]c3ncc(C(=O)N4CCC(O)CC4)cc23)c1)C(=O)NCC(F)(F)F] | N~2~-(5-{5-[(4-hydroxypiperidin-1-yl)carbonyl]-1H-pyrrolo[2,3-b]pyridin-3-yl}pyridin-3-yl)-N-(2,2,2-trifluoroethyl)-D-valinamide | Calc'd 519.2, found 519.2 |
| 3-14 | 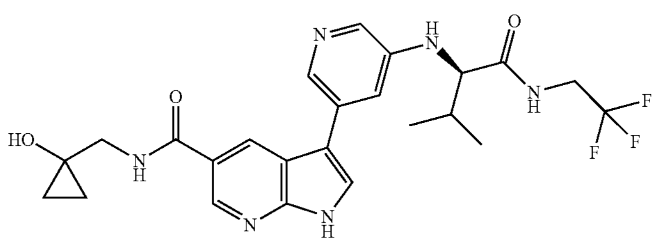 [SMILES: CC(C)[C@@H](Nc1cncc(-c2c[nH]c3ncc(C(=O)NCC4(O)CC4)cc23)c1)C(=O)NCC(F)(F)F] | N-[(1-hydroxycyclopropyl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide | Calc'd 505.2, found 505.2 |

Examples generated via General Scheme 4:

Example 4-1

3-Methyl-2-(5-(5-sulfamoyl-1H-pyrrolo[2,3-b]pyridin-3-yl)pyridin-3-ylamino)-N-(2,2,2-trifluoroethyl)butanamide (4-1)

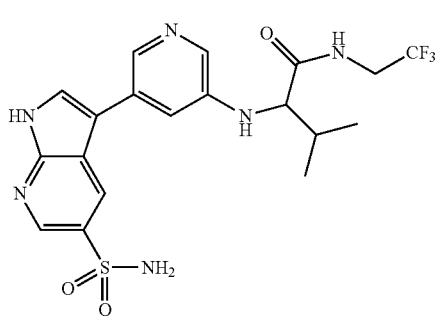

Step 1 5-bromo-1-((2-(trimethylsilyl)ethoxy)methyl)-1H-pyrrolo[2,3-b]pyridine (4-1a)

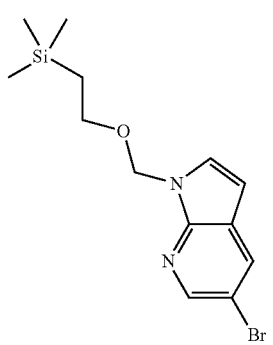

4-1a

To a solution of 5-bromo-7-azaindole (Aldrich, 2 g, 10.15 mmol) in DMF (40.6 ml) at 0° C. was added sodium hydride (0.690 g, 17.26 mmol). The reaction was aged for 10 min followed by addition of SEM-Cl (2.340 ml, 13.20 mmol). The reaction was allowed to warm to RT and stir for 4 h. The mixture was diluted with saturated NH₄Cl (30 mL) and product extracted with ethyl acetate (30 mL). The organic extract was washed with brine (30 mL), dried over sodium sulfate, filtered and concentrated in vacuo. The residue was purified by column chromatography on silica gel (50 g, 0-50% ethyl acetate/hexanes) to give the compound 4-1a (3.2 gm) as a clear oil.

LRMS (ESI) m/z 327.1 [(M+H)$^+$; calcd for C13H19BrN2OSi: 327.1].

Step 2 Methyl 3-(1-((2-(trimethylsilyl)ethoxy)methyl)-1H-pyrrolo[2,3-b]pyridin-5-ylsulfonyl)propanoate (4-1b)

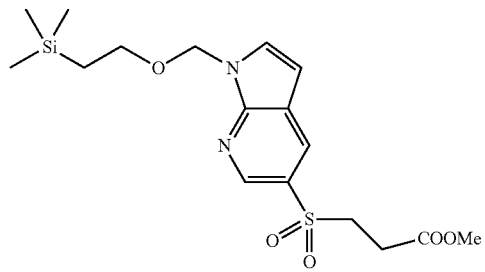

4-1b

To a nitrogen gas purged sealable vial of 5-bromo-1-((2-(trimethylsilyl)ethoxy)methyl)-1H-pyrrolo[2,3-b]pyridine 4-1a (3000 mg, 9.17 mmol), copper(i) iodide (6983 mg, 36.7 mmol) and sodium 3-methoxy-3-oxopropane-1-sulfinate (TYGER) (6385 mg, 36.7 mmol) was added DMSO (15 ml). The reaction mixture was heated in an oil bath at 105° C. for 18 hrs. LCMS analysis showed reaction to be a mixture of desired ester and acid. The reaction was quenched into ethyl acetate (200 ml) and water (200 ml) and the ph adjusted from 7 to 3 with 1N HCl. The reaction was filtered thru celite and sand and the filtrate layers separated. The organic which contained a mix of acid and ester was dried over sodium sulfate, filtered and concentrated to an oil. The oil was azeotroped with toluene to remove any remaining water to give a brown oil, 3.4 gms. The oil was dissolved in dichloromethane (20 ml) and methanol (20.00 ml) cooled to 0° C. and TMS-Diazomethane (4.94 ml, 9.88 mmol) slowly added dropwise. The reaction was stirred at 0° C. for 10 minutes, quenched with aq. KHSO$_4$ and allowed to stir at room temperature for 1 hr. The reaction was concentrated to remove methanol and the product extracted into ethyl acetate (100 ml), dried over sodium sulfate and concentrated to oil. The oil was chromatographed on silica (100 g, 0-50% ethyl acetate/hexanes) to give the product 4-1b as oil, 1.46 g.

LRMS (ESI) m/z 399.1 [(M+H)$^+$; calcd for C17H26N2O5SSi: 399.1].

Step 3 Methyl 3-(3-(4,4,5,5-tetramethyl-1,3,2-dioxaborolan-2-yl)-1-((2-(trimethylsilyl)ethoxy)methyl)-1H-pyrrolo[2,3-b]pyridin-5-ylsulfonyl)propanoate

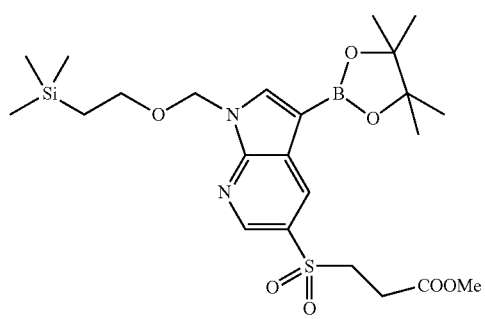

4-1c

To a solution of methyl 3-(1-((2-(trimethylsilyl)ethoxy)methyl)-1H-pyrrolo[2,3-b]pyridin-5-ylsulfonyl)propanoate 4-1b. (1300 mg, 3.26 mmol) in MTBE (13 ml) was added bispin (994 mg, 3.91 mmol), Di-mu-methoxobis(1,5-cyclooctadiene)diiridium (12148-71-9) (108 mg, 0.163 mmol) and 4,4'-Di-tert-butyl-2,2'-dipyridyl (43.8 mg, 0.163 mmol). The reaction was sealed and allowed to stir at RT for 5 minutes then heated at 75° C. for 1 hr. The reaction was cooled and used as is in the next step without purification.

Step 4 Methyl 3-(3-(5-(3-methyl-1-oxo-1-(2,2,2-trifluoroethylamino)butan-2-ylamino)pyridin-3-yl)-1-((2-(trimethylsilyl)ethoxy)methyl)-1H-pyrrolo[2,3-b]pyridin-5-ylsulfonyl)propanoate (4-1d)

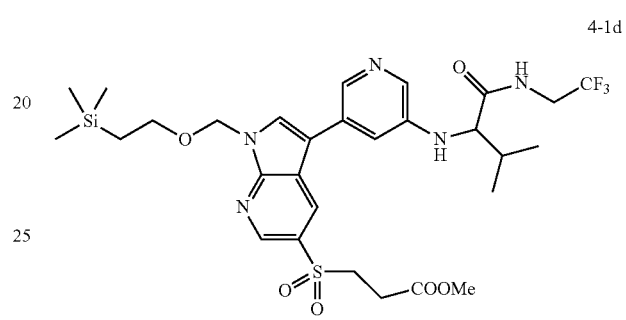

4-1d

To methyl 3-(3-(4,4,5,5-tetramethyl-1,3,2-dioxaborolan-2-yl)-1-((2-(trimethylsilyl)ethoxy)methyl)-1H-pyrrolo[2,3-b]pyridin-5-ylsulfonyl)propanoate 4-1c (3.26 mmol) was added aqueous sodium carbonate (4.89 ml, 9.79 mmol), 2-[(5-bromopyridin-3-yl)amino]-3-methyl-N-(2,2,2-trifluoroethyl)butanamide (1386 mg, 3.91 mmol) and Tetrakis (188 mg, 0.163 mmol). The reaction mixture was heated at 100° C. in a sealed vessel for 1 h. The reaction was cooled, quenched with water (50 mL), and product extracted with ethyl acetate (100 mL). The organic extract was dried over sodium sulfate, filtered and concentrated to oil. The oil was chromatographed on silica (100 g) using 50-100% ethyl acetate/hexanes to give the desired product 4-1d (1.1 g).

LRMS (ESI) m/z 672.2 [(M+H)$^+$; calcd for C29H40F3N5O6SSi: 672.2].

Step 5 3-Methyl-2-(5-(5-sulfamoyl-1-((2-(trimethylsilyl)ethoxy)methyl)-1H-pyrrolo[2,3-b]pyridin-3-yl)pyridin-3-ylamino)-N-(2,2,2-trifluoroethyl)butanamide (4-1e)

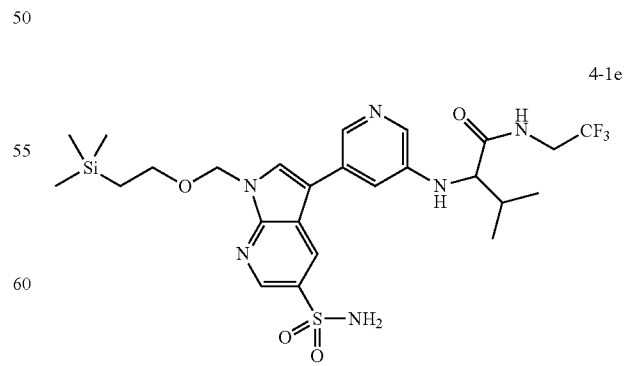

4-1e

To a mixture of methyl 3-(3-(5-(3-methyl-1-oxo-1-(2,2,2-trifluoroethylamino)butan-2-ylamino)pyridin-3-yl)-1-((2-(trimethylsilyl)ethoxy)methyl)-1H-pyrrolo[2,3-b]pyridin-5- ylsulfonyl)propanoate 4-1d (300 mg, 0.447 mmol) in DMSO (1.2 ml) was added DBU (0.135 ml, 0.893 mmol) and the reaction allowed to stir for 15 min. A solution of hydroxylamine-o-sulfonic acid (253 mg, 2.233 mmol) and sodium acetate (147 mg, 1.786 mmol) in water (0.8 mL) was added. The cloudy oily mixture was allowed to stir at RT for ½ hrs and then an additional charge of sodium acetate (147 mg, 1.786 mmol) and hydroxylamine-o-sulfonic acid (253 mg, 2.233 mmol) added and the mixture warmed to 40° C. for 2 hrs. The reaction was diluted with water (30 mL) and product extracted with ethyl acetate (50 ml), dried over sodium sulfate, filtered and concentrated to an oil. The oil was dissolved in DCM and chromatographed on silica (25 gm, using 2-10% methanol/DCM to give the desired product 4-1e as a white solid (240 mg). LRMS (ESI) m/z 601.2 [(M+H)$^+$; calcd for C25H35F3N6O4SSi: 601.2].

Step 6 3-Methyl-2-(5-(5-sulfamoyl-1H-pyrrolo[2,3-b]pyridin-3-yl)pyridin-3-ylamino)-N-(2,2,2-trifluoroethyl)butanamide (4-1)

The above compound, 4-1, was prepared and isolated in a manner similar to Example 1-2, step 2, utilizing 3-methyl-2-(5-(5-sulfamoyl-1-((2-(trimethylsilyl)ethoxy)methyl)-1H-pyrrolo[2,3-b]pyridin-3-yl)pyridin-3-ylamino)-N-(2,2,2-trifluoroethyl)butanamide 4-1e.
LRMS (ESI) m/z 471.1 [(M+H)$^+$; calcd for C19H21F3N6O3S: 471.1].

Example 4-2

2-(5-(5-(N,N-dimethylsulfamoyl)-1H-pyrrolo[2,3-b]pyridin-3-yl)pyridin-3-ylamino)-3-methyl-N-(2,2,2-trifluoroethyl)butanamide (4-2)

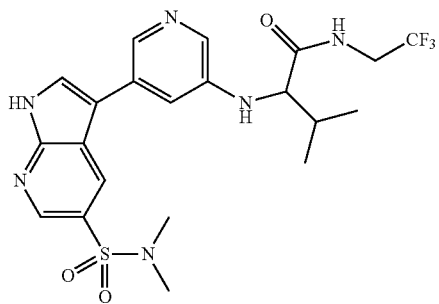

4-2

Step 1 2-(5-(5-(N,N-dimethylsulfamoyl)-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide (4-2a)

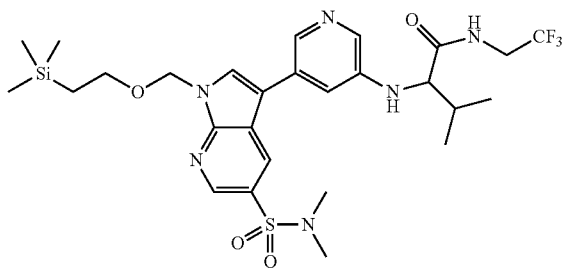

4-2a

A mixture of PS-triphenylphosphine (185 mg, 0.350 mmol) and 3-methyl-2-(5-(5-sulfamoyl-1-((2-(trimethylsilyl)ethoxy)methyl)-1H-pyrrolo[2,3-b]pyridin-3-yl)pyridin-3-ylamino)-N-(2,2,2-trifluoroethyl)butanamide 4-1 (50 mg, 0.083 mmol) in THF (1000 µl) was stirred for 5 min at RT. To this mixture was added di-tert-butyl azodicarboxylate (77 mg, 0.333 mmol) followed by addition of methanol (168 µl, 4.16 mmol). The reaction was allowed to stir at RT for 18 hr, quenched with water (0.5 ml) and stirred well for 30 minutes. The reaction was filtered and solids washed with THF (2 mL). The filtrate was concentrated to a foam 4-2a (53 mg).
LRMS (ESI) m/z 629.2 [(M+H)$^+$; calcd for C27H39F3N6O4SSi: 629.2].

Step 2 2-(5-(5-(N,N-dimethylsulfamoyl)-1H-pyrrolo[2,3-b]pyridin-3-yl)pyridin-3-ylamino)-3-methyl-N-(2,2,2-trifluoroethyl)butanamide (4-2)

The above compound, 4-2, was prepared and isolated in a manner similar to Example 1-2, step 2 utilizing 2-(5-(5-(N,N-dimethylsulfamoyl)-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide 4-2a.
LRMS (ESI) m/z 499.1 [(M+H)$^+$; calcd for C21H25F3N6O3S: 499.1].
Examples generated via General Scheme 5:

Example 5-1

N$^2$-[5-(5-amino-1H-pyrrolo[2,3-b]pyridin-3-yl)pyridin-3-yl]-N-(2,2,2-trifluoroethyl)valinamide (5-1)

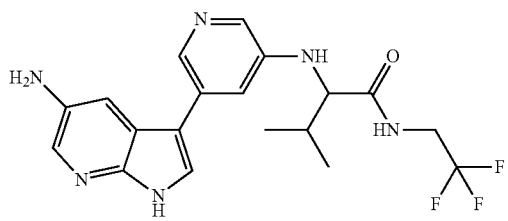

5-1

Step 1 N$^2$-{5-[5-(benzylamino)-1-{[2-(trimethylsilyl)ethoxy]methyl}-1H-pyrrolo[2,3-b]pyridin-3-yl]pyridin-3-yl}-N-(2,2,2-trifluoroethyl)valinamide (5-1a)

To a nitrogen gas purged microwave vial of N$^2$-[5-(5-chloro-1-{[2-(trimethylsilyl)ethoxy]methyl}-1H-pyrrolo[2,3-b]pyridin-3-yl)pyridin-3-yl]-N-(2,2,2-trifluoroethyl)valinamide, 2-1a (1380 mg, 2.482 mmol), palladium(II) acetate (80 mg, 0.356 mmol) and (2R)-1-[(1R)-1-[bis(1,1-dimethylethyl)phosphino]ethyl]-2-(dicyclohexylphosphino)ferrocene (188 mg, 0.339 mmol) in DME (5 mL) was added benzylamine (0.407 mL, 3.72 mmol) followed by 1M lithium bis(trimethylsilyl)amide/THF (3.72 mL, 3.72 mmol). The reaction mixture was sealed and heated in an oil bath at 100° C. in a sealed microwave vessel for 18 h. An additional amount of palladium(II) acetate (80 mg, 0.356 mmol) and (2R)-1-[(1R)-1-[bis(1,1-dimethylethyl)phosphino]ethyl]-2-(dicyclohexylphosphino)ferrocene (188 mg, 0.339 mmol), benzylamine (0.407 mL, 3.72 mmol) followed by 1M lithium bis(trimethylsilyl)amide/THF (3.72 mL, 3.72 mmol) was added and the reaction was allowed to stir at 100° C. for 2 h. The reaction was quenched with aq. KHSO$_4$, diluted with ethyl acetate. The organic layer was washed with aq. NaHCO$_3$, dried over sodium sulfate, filtered and concentrated to an oil. The oil purified on silica gel (EtOAc/hexane; 50-100%) to afford the title compound, 5-1a.
MS APCI: [M+H]$^+$ m/z=627.2.

Step 2 N²-{5-[5-(amino)-1-{[2-(trimethylsilyl) ethoxy]methyl}-1H-pyrrolo[2,3-b]pyridin-3-yl]pyridin-3-yl}-N-(2,2,2-trifluoroethyl)valinamide (5-1b)

To a solution of N²-{5-[5-(benzylamino)-1-{[2-(trimethylsilyl)ethoxy]methyl}-1H-pyrrolo[2,3-b]pyridin-3-yl]pyridin-3-yl}-N-(2,2,2-trifluoroethyl)valinamide 5-1a (1.03 g, 1.643 mmol) in MeOH (4 mL) purged with nitrogen (3×) was added palladium hydroxide on carbon (0.540 mg, 0.769 μmol) added and mixture hydrogenated 1 atm for 22 h. The reaction was filtered over Celite and the residue was purified by preparative HPLC reverse phase (C-18), eluting with acetonitrile/water (0.1% TFA), to give product 5-1b. The combined product fractions were basified with NaHCO₃, dried over MgSO₄, filtered and concentrated. MS APCI: [M+H]⁺ m/z=537.0.

Step 3 N²-[5-(5-amino-1H-pyrrolo[2,3-b]pyridin-3-yl)pyridin-3-yl]-N-(2,2,2-trifluoroethyl)valinamide (5-1)

To a solution N²-{5-[5-(amino)-1-{[2-(trimethylsilyl)ethoxy]methyl}-1H-pyrrolo[2,3-b]pyridin-3-yl]pyridin-3-yl}-N-(2,2,2-trifluoroethyl)valinamide 5-1b (50 mg, 0.093 mmol) in DCM (2 mL) was added TFA (1.4 mL, 18.6 mmol) and the resultant mixture was stirred for 2 h. The mixture was concentrated in vacuo, resuspended in MeOH (1 mL) and to this was added ethylenediamine (13 μl, 0.186 mmol) and sodium hydroxide (10 M aq) (0.065 mL, 0.652 mmol). After 18 h, the reaction was transferred to vial with an additional 1 mL of dimethylsulfoxide and this solution was purified by mass triggered reverse phase HLPC. The fractions containing product 5-1 were basified with NaHCO3, dried over MgSO4, filtered and concentrated. MS APCI: [M+H]⁺ m/z=407.1.

Example 5-2

N²-{5-[5-(acetylamino)-1H-pyrrolo[2,3-b]pyridin-3-yl]pyridin-3-yl}-N-(2,2,2-trifluoroethyl)valinamide (5-2)

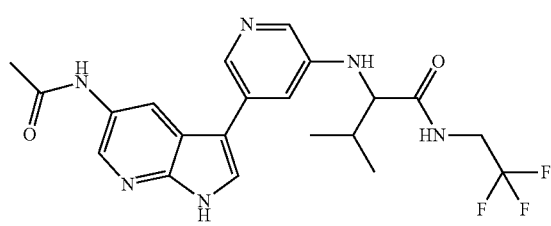

5-2

Step 1. N²-[5-(5-[(acetylamino)]-1-{[2-(trimethylsilyl)ethoxy]methyl}-1H-pyrrolo[2,3-b]pyridin-3-yl)pyridin-3-yl]-N-(2,2,2-trifluoroethyl)valinamide Residue (5-2a)

To a solution of N²-[5-(5-amino-1-{[2-(trimethylsilyl)ethoxy]methyl}-1H-pyrrolo[2,3-b]pyridin-3-yl)pyridin-3-yl]-N-(2,2,2-trifluoroethyl)valinamide 5-1b (50 mg, 0.093 mmol) in DCM (1.5 mL) and pyridine (0.2 mL) was added acetic anhydride (9.23 μL, 0.098 mmol) and the mixture was stirred for 2 h. The reaction was concentrated and the residue 5-2a was carried on without further purification.

Step 2. N²-{5-[5-(acetylamino)-1H-pyrrolo[2,3-b]pyridin-3-yl]pyridin-3-yl}-N-(2,2,2-trifluoroethyl)valinamide (5-2)

To a solution of the above residue from Step 1 in DCM (2 mL) was added TFA (2.0 mL, 26 mmol) and the resultant mixture was stirred for 2 h. The mixture was concentrated in vacuo, resuspended in MeOH (1 mL) and to this was added ethylenediamine (13 μl, 0.187 mmol) and sodium hydroxide (10 M aq) (0.065 mL, 0.653 mmol). After 18 h, the reaction was transferred to vial with an additional 1 mL of dimethylsulfoxide and this solution was purified by mass triggered reverse phase HLPC. The fractions containing product 5-2 were basified with NaHCO3, dried over MgSO4, filtered and concentrated.

MS APCI: [M+H]⁺ m/z=449.0. ¹H NMR (600 MHz, DMSO) δ 9.99 (s, 1H), 8.72 (d, J=6.5 Hz, 1H), 8.43 (s, 1H), 8.30 (s, 1H), 8.05 (s, 1H), 7.89 (s, 1H), 7.73 (s, 1H), 7.14 (s, 1H), 6.03 (d, J=8.5 Hz, 1H), 3.93 (m, 1H), 3.85 (m, 1H), 3.69 (m, 1H), 2.02 (s, 3H), 2.00 (m, 1H), 0.98 (d, J=6.7 Hz, 3H), 0.92 (d, J=6.7 Hz, 3H).

Example 5-3

N²-(5-{5-[(methylsulfonyl)amino]-1H-pyrrolo[2,3-b]pyridin-3-yl}pyridin-3-yl)-N-(2,2,2-trifluoroethyl)valinamide (5-3)

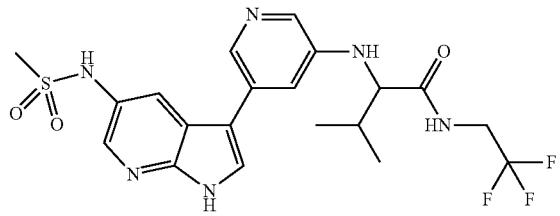

5-3

Step 1. N²-[5-(5-[(methylsulfonyl)amino]-1-{[2-(trimethylsilyl)ethoxy]methyl}-1H-pyrrolo[2,3-b]pyridin-3-yl)pyridin-3-yl]-N-(2,2,2-trifluoroethyl)valinamide Residue (5-3a)

To a solution of N²-[5-(5-amino-1-{[2-(trimethylsilyl)ethoxy]methyl}-1H-pyrrolo[2,3-b]pyridin-3-yl)pyridin-3-yl]-N-(2,2,2-trifluoroethyl)valinamide 5-1b (50 mg, 0.093 mmol) in DCM (2 mL) and pyridine (0.5 mL) was added methanesulfonyl chloride (7.62 μl, 0.098 mmol) and mixture was stirred for 18 h. The residue 5-3a was used without further purification. MS APCI: [M+H]⁺ m/z=615.1.

Step 2. N²-(5-{5-[(methylsulfonyl)amino]-1H-pyrrolo[2,3-b]pyridin-3-yl}pyridin-3-yl)-N-(2,2,2-trifluoroethyl)valinamide (5-3)

To a solution of N²-[5-(5-[(methylsulfonyl)amino]-1-{[2-(trimethylsilyl)ethoxy]methyl}-1H-pyrrolo[2,3-b]pyridin-3-yl)pyridin-3-yl]-N-(2,2,2-trifluoroethyl)valinamide 5-3a (57 mg, 0.093 mmol) from step 1 in DCM (2 mL) was added TFA (0.714 mL, 9.27 mmol) and the resultant mixture was stirred for 2 h. The mixture was concentrated in vacuo, resuspended in MeOH (1 mL) and to this was added ethylenediamine (0.013 mL, 0.185 mmol) and sodium hydroxide (10 M aq) (0.065 mL, 0.649 mmol). After 18 h, the reaction was transferred to vial with an additional 1 mL of dimethylsulfoxide and this solution was purified by mass triggered reverse phase HLPC. The fractions containing product 5-3 were basified with NaHCO3, dried over MgSO4, filtered and concentrated.

MS APCI: [M+H]$^+$ m/z=485.1. $^1$H NMR (600 MHz, DMSO) δ 12.02 (s, 1H), 9.50 (s, 1H), 8.72 (t, J=6.5 Hz, 1H), 8.30 (s, 1H), 8.17 (s, 1H), 8.05 (s, 1H), 7.92 (s, 1H), 7.82 (d, J=18 Hz, 1H), 7.15 (s, 1H), 6.03 (d, J=7.5 Hz, 1H), 3.93 (m, 1H), 3.84 (m, 1H), 3.70 (dd, J=6.5 Hz, 1H), 2.82 (s, 3H), 2.00 (m, 1H), 0.98 (d, J=6.9 Hz, 3H), 0.92 (d, J=6.9 Hz, 3H).

Examples 5-4 and 5-5

Enantiomers

N$^2$-(5-{5-[(methylsulfonyl)amino]-1H-pyrrolo[2,3-b]pyridin-3-yl}pyridin-3-yl)-N-(2,2,2-trifluoroethyl)-L-valinamide, 5-4, and N$^2$-(5-{5-[(methylsulfonyl)amino]-1H-pyrrolo[2,3-b]pyridin-3-yl}pyridin-3-yl)-N-(2,2,2-trifluoroethyl)-D-valinamide, 5-5

N$^2$-(5-{5-[(methylsulfonyl)amino]-1H-pyrrolo[2,3-b]pyridin-3-yl}pyridin-3-yl)-N-(2,2,2-trifluoroethyl)valinamide 5-3 was separated via chiral chromatography using a Chiral Technology AD-H 2.1×25 cm, 5 uM with 25%/75% methanol/CO2 (no other modifiers) with 70 mL/min with a 16 min run time. Injections of 0.85 ml were performed on the Berger Multigram II SFC. Elution was observed at 2.72 minutes and 11.27 minutes.
Peak 1=MS APCI: [M+H]$^+$ m/z=485.1
Peak 2=MS APCI: [M+H]$^+$ m/z=485.1

Example 5-6

N$^2$-{5-[5-(propanoylamino)-1H-pyrrolo[2,3-b]pyridin-7-ium-3-yl]pyridin-3-yl}-N-(2,2,2-trifluoroethyl)valinamide (5-6)

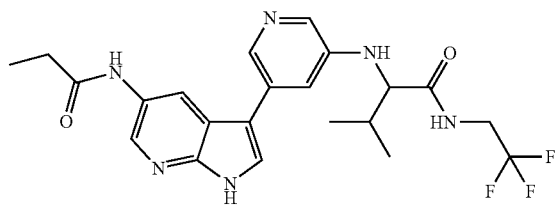

5-6

Step 1. N$^2$-{5-[5-(propanoylamino)-1H-pyrrolo[2,3-b]pyridin-7-ium-3-yl]pyridin-3-yl}-N-(2,2,2-trifluoroethyl)valinamide (5-6a)

To a solution of N$^2$-[5-(5-amino-1-{[2-(trimethylsilyl)ethoxy]methyl}-1H-pyrrolo[2,3-b]pyridin-3-yl)pyridin-3-yl]-N-(2,2,2-trifluoroethyl)valinamide 5-1b (25 mg, 0.047 mmol) and propionic acid (3.5 mg, 0.051 mmol) in DMF (0.5 mL) was added DIPEA (0.012 mL, 0.07 mmol) and 2,4,6-tripropyl-1,3,5,2,4,6-trioxatriphosphorinane-2,4,6-trioxide (0.042 mL, 0.070 mmol). The reaction was stirred overnight. After 18 h, the reaction was concentrated and the residue 5-6a was carried on without further purification.

Step 2. N$^2$-{5-[5-(propanoylamino)-1H-pyrrolo[2,3-b]pyridin-7-ium-3-yl]pyridin-3-yl}-N-(2,2,2-trifluoroethyl)valinamide (5-6)

To a solution of the above residue from step 1, 5-6a, in DCM (0.5 mL) was added TFA (0.718 mL, 9.32 mmol) and the resultant mixture was stirred for 2 h. The mixture was concentrated in vacuo, resuspended in MeOH (1 mL) and to this was added ethylenediamine (6.29 μl, 0.093 mmol) and sodium hydroxide (10 M aq) (0.033 mL, 0.326 mmol). After 18 h, the reaction was transferred to vial with an additional 1 mL of dimethylsulfoxide and this solution was purified by mass triggered reverse phase HLPC. The fractions containing product 5-6 were basified with NaHCO3, dried over MgSO4, filtered and concentrated.

MS APCI: [M+H]$^+$ m/z=463.1.

$^1$H NMR (600 MHz, DMSO) δ 11.85 (s, 1H), 9.92 (s, 1H), 8.72 (t, J=6.0 Hz, 1H), 8.48 (s, 1H), 8.32 (s, 1H), 8.08 (s, 1H), 7.90 (s, 1H), 7.75 (s, 1H), 7.19 (s, 1H), 6.09 (m, 1H), 3.93 (m, 1H), 3.84 (m, 1H), 3.70 (dd, J=6.5 Hz, 1H), 2.32 (q, J=7 Hz, 1H), 2.00 (m, 1H), 1.07 (t, J=7.0 Hz, 3H), 0.98 (d, J=6.9 Hz, 3H), 0.92 (d, J=6.9 Hz, 3H)

The following examples 5-7 through 5-8 as shown in Table 8 were prepared in an analogous manner of that described above using materials that are commercially available or known, or that can be prepared using procedures known in the art or by generally following procedures described herein for various intermediates.

TABLE 8

| Example Number | Structure | IUPAC Name | Exact Mass [M + H]+ |
|---|---|---|---|
| 5-7 | ![structure] | N~2~-(5-{5-[(hydroxyacetyl)amino]-1H-pyrrolo[2,3-b]pyridin-3-yl}pyridin-3-yl)-N-(2,2,2-trifluoroethyl)valinamide | Calc'd 465.2, found 465.1 |

TABLE 8-continued

| Example Number | Structure | IUPAC Name | Exact Mass [M + H]+ |
|---|---|---|---|
| 5-8 | 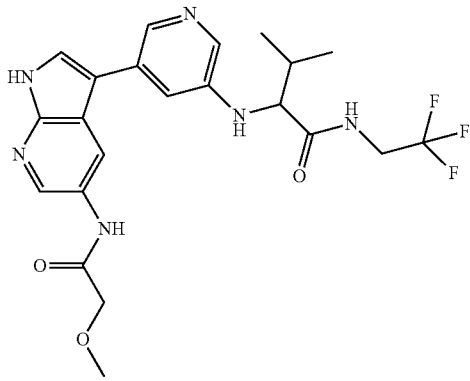 [SMILES: COCC(=O)Nc1cnc2[nH]cc(-c3cncc(NC(C(=O)NCC(F)(F)F)C(C)C)c3)c2c1] | N~2~-(5-{5-[(methoxyacetyl)amino]-1H-pyrrolo[2,3-b]pyridin-3-yl}pyridin-3-yl)-N-(2,2,2-trifluoroethyl)valinamide | Calc'd 479.2, found 479.1 |

Examples generated via General Scheme 5:

Example 6-1

$N^2$-(5-{5-[(propan-2-ylcarbamoyl)amino]-1H-pyrrolo[2,3-b]pyridin-3-yl}pyridin-3-yl)-N-(2,2,2-trifluoroethyl)valinamide (6-1)

6-1

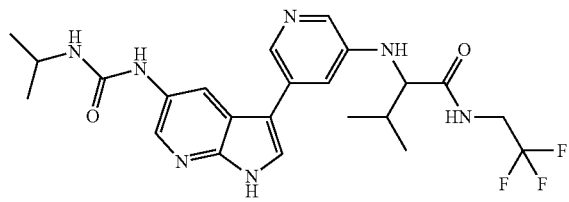

Step 1. 6-1a Residue

To a solution of $N^2$-[5-(5-amino-1-{[2-(trimethylsilyl)ethoxy]methyl}-1H-pyrrolo[2,3-b]pyridin-3-yl)pyridin-3-yl]-N-(2,2,2-trifluoroethyl)valinamide 5-1b (25 mg, 0.047 mmol) and DIPEA (0.07 mmol, 0.012 mL) in DMF (0.5 mL) was added isocyanate (4.0 mg, 0.051 mmol). The reaction was stirred overnight. After 18 h, the reaction was concentrated and the residue 6-1a was carried on without further purification.

Step 2. $N^2$-(5-{5-[(propan-2-ylcarbamoyl)amino]-1H-pyrrolo[2,3-b]pyridin-3-yl}pyridin-3-yl)-N-(2,2,2-trifluoroethyl)valinamide (6-1)

To a solution of the above residue 6-1a from step 1 in DCM (0.5 mL) was added TFA (0.718 mL, 9.32 mmol) and the resultant mixture was stirred for 2 h. The mixture was concentrated in vacuo, resuspended in MeOH (1 mL) and to this was added ethylenediamine (6.29 μl, 0.093 mmol) and sodium hydroxide (10 M aq) (0.033 mL, 0.326 mmol). After 18 h, the reaction was transferred to vial with an additional 1 mL of dimethylsulfoxide and this solution was purified by mass triggered reverse phase HLPC. The fractions containing product 6-1 were basified with NaHCO3, dried over MgSO4, filtered and concentrated.

MS APCI: [M+H]$^+$ m/z=492.1.

$^1$H NMR (600 MHz, DMSO) δ 11.75 (s, 1H), 8.71 (t, J=4.0 Hz, 1H), 8.30 (s, 1H), 8.25 (s, 1H), 8.08 (s, 1H), 8.06 (s, 1H), 7.89 (s, 1H), 7.72 (s, 1H), 7.19 (s, 1H), 6.09 (m, 1H), 6.02 (d, J=6.8 Hz, 1H) 3.97 (m, 1H), 3.83 (m, 1H), 3.73 (m, 1H), 3.69 (m, 1H), 2.00 (m, 1H), 1.05 (d, J=7.0 Hz, 6H), 0.98 (d, J=6.9 Hz, 3H), 0.92 (d, J=6.9 Hz, 3H)

The following examples, 6-2 through 6-5 as shown in Table 9 were prepared in an analogous manner of that described above using materials that are commercially available or known, or that can be prepared using procedures known in the art or by generally following procedures described herein for various intermediates.

TABLE 9

| Example Number | Structure | IUPAC Name | Exact Mass [M + H]+ |
|---|---|---|---|
| 6-2 | 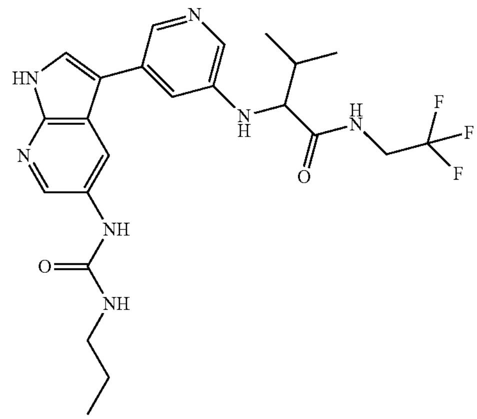 [SMILES: CCCNC(=O)Nc1cnc2[nH]cc(-c3cncc(NC(C(=O)NCC(F)(F)F)C(C)C)c3)c2c1] | N~2~-(5-{5-[(propylcarbamoyl)amino]-1H-pyrrolo[2,3-b]pylidin-3-yl}pyridin-3-yl)-N-(2,2,2-trifluoroethyl)valinamide | Calc'd 492.2, found 492.1 |
| 6-3 | 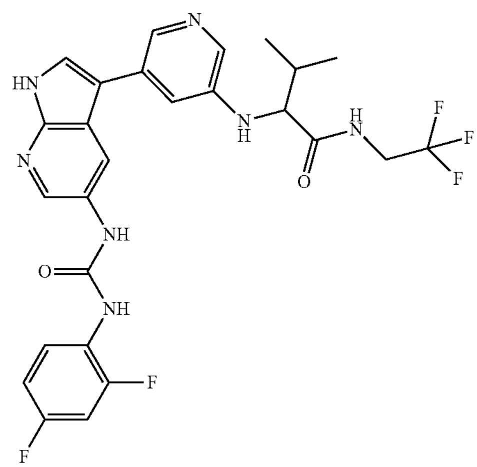 [SMILES: CC(C)C(Nc1cncc(-c2c[nH]c3ncc(NC(=O)Nc4ccc(F)cc4F)cc23)c1)C(=O)NCC(F)(F)F] | N~2~-[5-(5-{[(2,4-difluorophenyl)carbamoyl]amino}-1H-pyrrolo[2,3-b]pyridin-3-yl)pyridin-3-yl]-N-(2,2,2-trifluoroethyl)valinamide | Calc'd 562.2, found 562.1 |
| 6-4 | 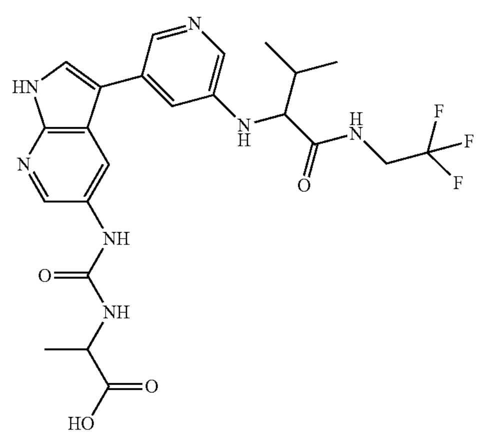 [SMILES: CC(NC(=O)Nc1cnc2[nH]cc(-c3cncc(NC(C(=O)NCC(F)(F)F)C(C)C)c3)c2c1)C(=O)O] | N-({3-[5-({2-methyl-1-[(2,2,2-trifluoroethyl)carbamoyl]propyl}amino)pyridin-3-yl]-1H-pyrrolo[2,3-b]pyridin-5-yl}carbamoyl)alanine | Calc'd 522.2, found 522.1 |

TABLE 9-continued

| Example Number | Structure | IUPAC Name | Exact Mass [M + H]+ |
|---|---|---|---|
| 6-5 | 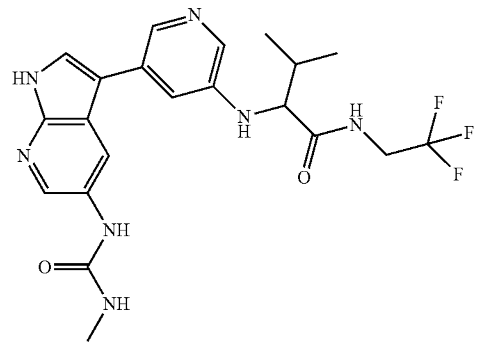 [SMILES: CNC(=O)Nc1cnc2[nH]cc(-c3cncc(NC(C(=O)NCC(F)(F)F)C(C)C)c3)c2c1] | N~2~-(5-{5-[(methylcarbamoyl)amino]-1H-pyrrolo[2,3-b]pyridin-3-yl}pyridin-3-yl)-N-(2,2,2-trifluoroethyl)valinamide | Calc'd 464.2, found 464.1 |

Example 7-1

Methyl {3-[5-({3-methyl-1-oxo-1-[(2,2,2-trifluoroethyl)amino]butan-2-yl}amino)pyridin-3-yl]-1H-pyrrolo[2,3-b]pyridin-5-yl}carbamate (7-1)

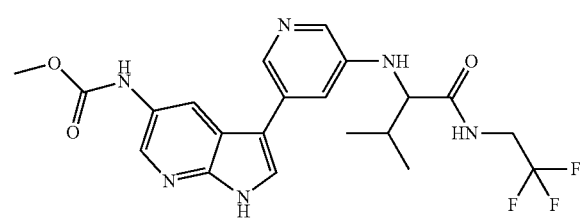

7-1

Step 1. Step 1 Residue (7-1a)

To a solution of N²-[5-(5-amino-1-{[2-(trimethylsilyl)ethoxy]methyl}-1H-pyrrolo[2,3-b]pyridin-3-yl)pyridin-3-yl]-N-(2,2,2-trifluoroethyl)valinamide 5-1b (25 mg, 0.047 mmol) and DIPEA (0.07 mmol, 0.012 mL) in DCM (0.5 mL) was added methyl chloroformate (0.051 mL, 0.051 mmol). The reaction was stirred overnight. After 18 h, the reaction was concentrated and the residue 7-1a was carried on without further purification.

Step 2. Methyl {3-[5-({3-methyl-1-oxo-1-[(2,2,2-trifluoroethyl)amino]butan-2-yl}amino)pyridin-3-yl]-1H-pyrrolo[2,3-b]pyridin-5-yl}carbamate (7-1)

To a solution of the above residue from step 1, 7-1a, in DCM (0.5 mL) was added TFA (0.718 mL, 9.32 mmol) and the resultant mixture was stirred for 2 h. The mixture was concentrated in vacuo, resuspended in MeOH (1 mL) and to this was added ethylenediamine (6.29 µl, 0.093 mmol) and sodium hydroxide (10 M aq) (0.033 mL, 0.326 mmol). After 18 h, the reaction was transferred to vial with an additional 1 mL of dimethylsulfoxide and this solution was purified by mass triggered reverse phase HLPC. The fractions containing product 7-1 were basified with NaHCO3, dried over MgSO4, filtered and concentrated.

MS APCI: [M+H]⁺ m/z=465.0.

¹H NMR (600 MHz, DMSO) δ 11.85 (s, 1H), 9.61 (br s, 1H), 8.72 (t, J=4.0 Hz, 1H), 8.28 (br s, 1H), 8.23 (s, 1H), 8.05 (s, 1H), 7.89 (s, 1H), 7.74 (s, 1H), 7.14 (s, 1H), 6.03 (d, J=7.2 Hz, 1H), 3.96 (m, 1H), 3.86 (m, 1H), 3.69 (dd, J=7.6 Hz, 1H), 3.63 (s, 3H), 2.00 (m, 1H), 0.98 (d, J=6.7 Hz, 3H), 0.92 (d, J=6.7 Hz, 3H).

The following examples, 7-2 and 7-3 as shown in Table 10, were prepared in an analogous manner of that described above using materials that are commercially available or known, or that can be prepared using procedures known in the art or by generally following procedures described herein for various intermediates.

TABLE 10

| Example Number | Structure | IUPAC Name | Exact Mass [M + H]+ |
|---|---|---|---|
| 7-2 | 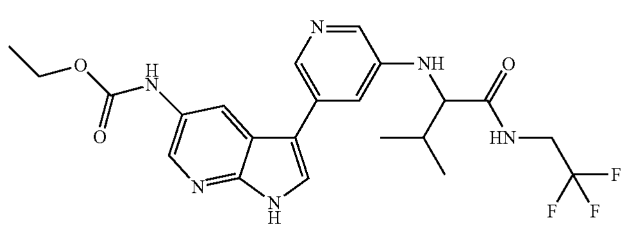 [SMILES: CCOC(=O)Nc1cnc2[nH]cc(-c3cncc(NC(C(=O)NCC(F)(F)F)C(C)C)c3)c2c1] | ethyl {3-[5-({2-methyl-1-[(2,2,2-trifluoroethyl)carbamoyl]propyl}amino)pyridin-3-yl]-1H-pyrrolo[2,3-b]pyridin-5-yl}carbamate | Calc'd 479.2, found 479.0 |

| Example Number | Structure | IUPAC Name | Exact Mass [M + H]+ |
|---|---|---|---|
| 7-3 | 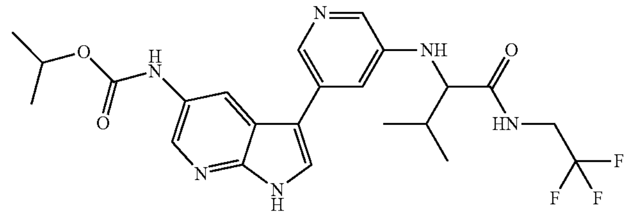 [SMILES: CC(C)OC(=O)Nc1cnc2[nH]cc(-c3cncc(NC(C(=O)NCC(F)(F)F)C(C)C)c3)c2c1] | 1-methylethyl {3-[5-({2-methyl-1-[(2,2,2-trifluoroethyl)carbamoyl]propyl}amino)pyridin-3-yl]-1H-pyrrolo[2,3-b]pyridin-5-yl}carbamate | Calc'd 493.2, found 493.0 |

Examples generated via General Scheme 6:

Example 8-1, 8-2 and 8-3

$N^2$-{5-[5-(1-methyl-1H-pyrazol-4-yl)-1H-pyrrolo[2,3-b]pyridin-3-yl]pyridin-3-yl}-N-(2,2,2-trifluoroethyl)valinamide (8-1)

8-1

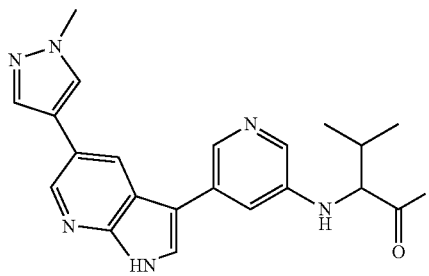

Step 1. $N^2$-{5-[5-(1-methyl-1H-pyrazol-4-yl)-1-{[2-(trimethylsilyl)ethoxy]methyl}-1H-pyrrolo[2,3-b]pyridin-3-yl]pyridin-3-yl}-N-(2,2,2-trifluoroethyl)valinamide (8-1a)

To a solution of $N^2$-[5-(5-chloro-1-{[2-(trimethylsilyl)ethoxy]methyl}-1H-pyrrolo[2,3-b]pyridin-3-yl)pyridin-3-yl]-N-(2,2,2-trifluoroethyl)valinamide 2-1a (200 mg, 0.360 mmol), 1-methyl-4-(4,4,5,5-tetramethyl-1,3,2-dioxaborolan-2-yl)-1H-pyrazole (CA) (90 mg, 0.432 mmol), X-PHOS (30.9 mg, 0.065 mmol), palladium(II) acetate (9.69 mg, 0.043 mmol) in DMF (2 mL) was added phosphate tribasic (153 mg, 0.719 mmol) and water (0.4 mL). The mixture was evacuated then $N_2$ purged 3 times and heated at 100° C. for overnight. After cooling the reaction was filtered and filtrate was loaded directly onto HPLC Reverse phase (C-18), eluting with acetonitrile/water (0.1% TFA), to give product 8-1a as a colorless foam. MS APCI: [M+H]+ m/z=602.1.

Step 2. $N^2$-{5-[5-(1-methyl-1H-pyrazol-4-yl)-1H-pyrrolo[2,3-b]pyridin-3-yl]pyridin-3-yl}-N-(2,2,2-trifluoroethyl)valinamide (8-1)

To a solution $N^2$-{5-[5-(1-methyl-1H-pyrazol-4-yl)-1-{[2-(trimethylsilyl)ethoxy]methyl}-1H-pyrrolo[2,3-b]pyridin-3-yl]pyridin-3-yl}-N-(2,2,2-trifluoroethyl)valinamide 8-1a (190 mg, 0.316 mmol) from step 1 in DCM (2 mL) was added TFA (2.4 mL, 31.6 mmol) and the resultant mixture was stirred for 2 h. The mixture was concentrated in vacuo, resuspended in MeOH (1 mL) and to this was added ethylenediamine (0.043 mL, 0.632 mmol) and sodium hydroxide (10 M aq) (0.221 mL, 2.21 mmol). After 18 h, the reaction was transferred to vial with an additional 1 mL of dimethylsulfoxide and this solution was purified by mass triggered reverse phase HLPC. The fractions containing product 8-1 were basified with NaHCO3, dried over MgSO4, filtered and concentrated.

MS APCI: [M+H]+ m/z=472.0.

$^1$H NMR (600 MHz, DMSO) δ 11.85 (s, 1H), 8.72 (t, J=6.5 Hz, 1H), 8.48 (d, J=1.9 Hz, 1H), 8.26 (d, J=1.9 Hz, 1H), 8.21 (s, 1H), 8.19 (d, J=1.8 Hz, 1H), 7.93 (s, 1H), 7.90 (d, J=1.9 Hz, 1H), 7.81 (d, J=2.4 Hz, 1H), 7.23 (t, J=2.0 Hz, 1H), 5.98 (d, J=8.0 Hz, 1H), 3.96 (m, 1H), 3.86 (s, 3H), 3.83 (m, 1H), 3.69 (dd, J=7.8 Hz, 1H), 2.02 (m, 1H), 0.98 (d, J=6.7 Hz, 3H), 0.92 (d, J=6.7 Hz, 3H).

Enantiomers:

$N^2$-{5-[5-(1-methyl-1H-pyrazol-4-yl)-1H-pyrrolo[2,3-b]pyridin-3-yl]pyridin-3-yl}-N-(2,2,2-trifluoroethyl)-L-valinamide, 8-2, and $N^2$-{5-[5-(1-methyl-1H-pyrazol-4-yl)-1H-pyrrolo[2,3-b]pyridin-3-yl]pyridin-3-yl}-N-(2,2,2-trifluoroethyl)-D-valinamide, 8-3

$N^2$-{5-[5-(1-methyl-1H-pyrazol-4-yl)-1H-pyrrolo[2,3-b]pyridin-3-yl]pyridin-3-yl}-N-(2,2,2-trifluoroethyl)valinamide 8-1 was separated via chiral chromatography using a Chiral Technology AD-H 2.1×25 cm, 5 uM with 45%/55% methanol/CO2 (no other modifiers) with 70 mL/min with a 16 min run time. Injections of 0.85 ml were performed on the Berger Multigram II SFC. Elution was observed at 1.39 minutes and 7.62 minutes.

Peak 1=MS APCI: [M+H]+ m/z=472.0.
Peak 2=MS APCI: [M+H]+ m/z=472.0

Examples generated via General Scheme 7:

Example 9-1

(R)-3-methyl-2-(5-(5-((2-(pyrrolidin-1-yl)ethoxy)methyl)-1H-pyrrolo[2,3-b]pyridin-3-yl)pyridin-3-ylamino)-N-(2,2,2-trifluoroethyl)butanamide (9-1)

9-1

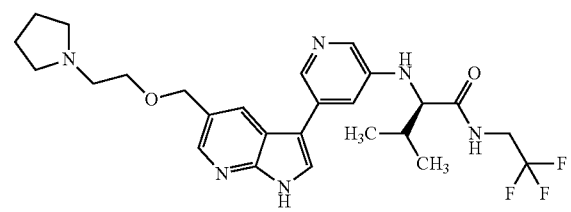

Step 1 (R)-3-methyl-2-(5-(5-((2-(pyrrolidin-1-yl)ethoxy)methyl)-1-((2-(trimethylsilyl)ethoxy)methyl)-1H-pyrrolo[2,3-b]pyridin-3-yl)pyridin-3-ylamino)-N-(2,2,2-trifluoroethyl)butanamide (9-1a)

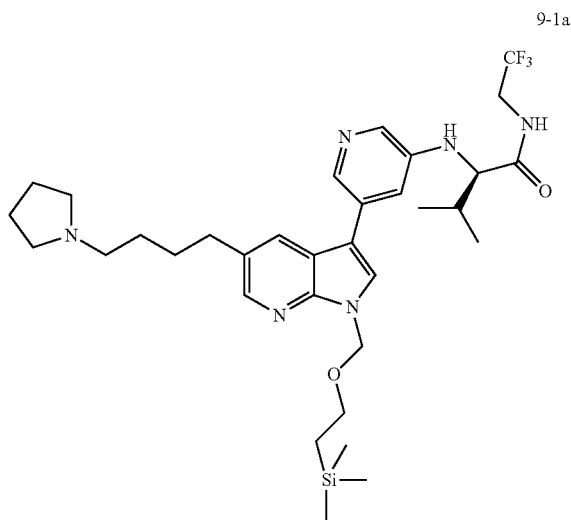 [SMILES: CC(C)[C@@H](Nc1cncc(-c2cn(COCC[Si](C)(C)C)c3ncc(CCCCN4CCCC4)cc23)c1)C(=O)NCC(F)(F)F]

9-1a

In a microwave vial purged with nitrogen containing (R)-2-(5-(5-chloro-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide, 2-1a (52 mg, 0.094 mmol), Potassium 2-(pyrrolidin-1-yl)ethoxymethyltrifluoroborate (CA) (44.4 mg, 0.189 mmol), cesium carbonate (105.3 mg, 0.323 mmol), palladium acetate (4.2 mg, 0.019 mmole) and RuPhos catalyst (17.45 mg, 0.037 mmol) was added a degassed mixture of 10:1 dioxane (500 μl)/water (50 μl). The reaction vessel was sealed and heated at 150° C. for 15 minutes in the microwave. LC/MS indicated product as a major peak. The reaction was cooled, passed through a celite cartridge, to remove water, the cartridge was washed with dichloromethane, ethyl acetate and the filtrate concentrated. The crude product 9-1a (60.7 mg) was used directly in the next step. LRMS (ESI) m/z 649.2 [(M+H)$^+$; calcd for $C_{32}H_{47}F_3N_6O_3Si$: 649.35].

Step 2 (R)-3-methyl-2-(5-(5-((2-(pyrrolidin-1-yl)ethoxy)methyl)-1H-pyrrolo[2,3-b]pyridin-3-yl)pyridin-3-ylamino)-N-(2,2,2-trifluoroethyl)butanamide (9-1)

In a microwave vial containing (R)-3-methyl-2-(5-(5-((2-(pyrrolidin-1-yl)ethoxy)methyl)-1-((2-(trimethylsilyl)ethoxy)methyl)-1H-pyrrolo[2,3-b]pyridin-3-yl)pyridin-3-ylamino)-N-(2,2,2-trifluoroethyl)butanamide 9-1a (60.7 mg, 0.094 mmol), added DMSO (1 ml, 0.094M) followed by Cesium Fluoride (284 mg, 1.871 mmol). The reaction mixture was heated at 140° C. for one hour on an oil bath open to air. LC/MS indicated conversion to product, the reaction mixture was filtered through a fine filter funnel and purified on the Gilson HPLC instrument using acetonitrile: water with 0.1% TFA buffer system using 10-60% gradient to give the title compound 9-1 (3.32 mg, 5.61%). LRMS (ESI) m/z 519.3 [(M+H)$^+$; calcd for $C_{26}H_{33}F_3N_6O_2$: 519.3]

The following examples, 9-2 through 9-9 as shown in Table 11, were prepared in an analogous manner of that described above using materials that are commercially available or known, or that can be prepared using procedures known in the art or by generally following procedures described herein for various intermediates

TABLE 11

| Example Number | Structure | IUPAC Name | Exact Mass [M + H]+ |
|---|---|---|---|
| 9-2 | 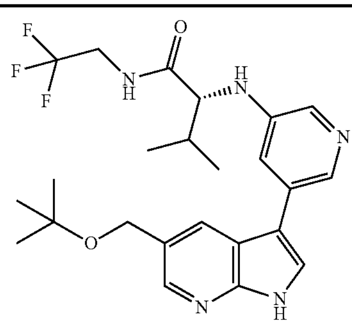 | N~2~-{5-[5-(tert-butoxymethyl)-1H-pyrrolo[2,3-b]pyridin-3-yl]pyridin-3-yl}-N-(2,2,2-trifluoroethyl)-D-valinamide | Calc'd 478.2, found 478.2 |
| 9-3 | 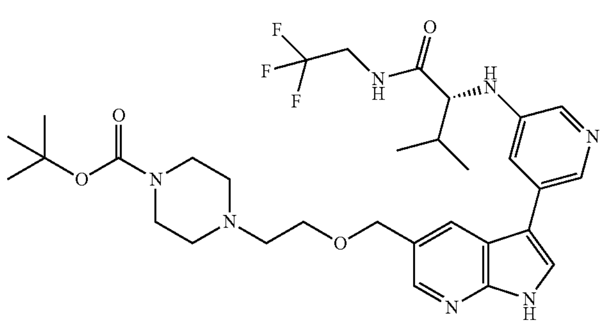 [SMILES: CC(C)[C@@H](Nc1cncc(-c2c[nH]c3ncc(COCCN4CCN(C(=O)OC(C)(C)C)CC4)cc23)c1)C(=O)NCC(F)(F)F] | tert-butyl 4-[2-({3-[5-({(1R)-2-methyl-1-[(2,2,2-trifluoroethyl)carbamoyl]propyl}amino)pyridin-3-yl]-1H-pyrrolo[2,3-b]pyridin-5-yl}methoxy)ethyl]piperazine-1-carboxylate | Calc'd 634.3, found 634.3 |

TABLE 11-continued

| Example Number | Structure | IUPAC Name | Exact Mass [M + H]+ |
|---|---|---|---|
| 9-4 | 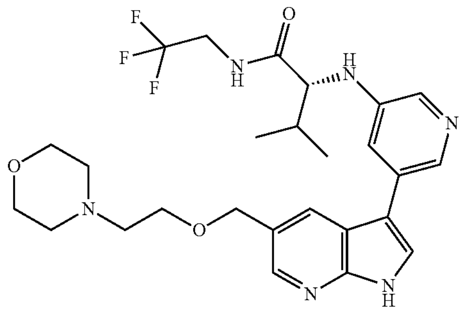 [SMILES: CC(C)[C@@H](Nc1cncc(-c2c[nH]c3ncc(COCCN4CCOCC4)cc23)c1)C(=O)NCC(F)(F)F] | N~2~-(5-{5-[(2-morpholin-4-ylethoxy)methyl]-1H-pyrrolo[2,3-b]pyridin-3-yl}pyridin-3-yl)-N-(2,2,2-trifluoroethyl)-D-valinamide | Calc'd 535.3, found 535.2 |
| 9-5 | 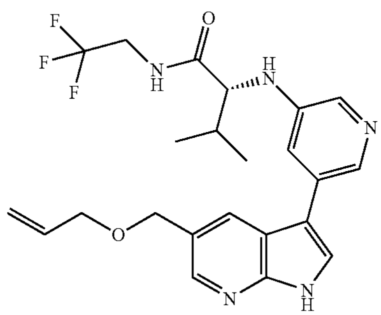 [SMILES: C=CCOCc1cnc2[nH]cc(-c3cncc(N[C@@H](C(=O)NCC(F)(F)F)C(C)C)c3)c2c1] | N~2~-(5-{5-[(prop-2-en-1-yloxy)methyl]-1H-pyrrolo[2,3-b]pyridin-3-yl}pyridin-3-yl)-N-(2,2,2-trifluoroethyl)-D-valinamide | Calc'd 462.2, found 462.2 |
| 9-6 | 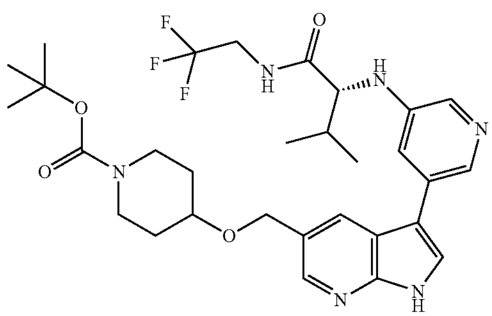 [SMILES: CC(C)[C@@H](Nc1cncc(-c2c[nH]c3ncc(COC4CCN(C(=O)OC(C)(C)C)CC4)cc23)c1)C(=O)NCC(F)(F)F] | tert-butyl 4-({3-[5-({(1R)-2-methyl-1-[(2,2,2-trifluoroethy)carbamoyl]propyl}amino)pyridin-3-yl]-1H-pyrrolo[2,3-b]pyridin-5-yl}methoxy)piperidine-1-carboxylate | Calc'd 605.3, found 605.3 |
| 9-7 | 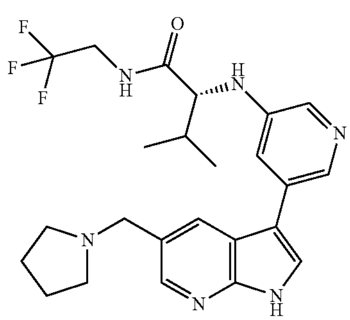 [SMILES: CC(C)[C@@H](Nc1cncc(-c2c[nH]c3ncc(CN4CCCC4)cc23)c1)C(=O)NCC(F)(F)F] | N~2~-{5-[5-(pyrrolidin-1-ylmethyl)-1H-pyrrolo[2,3-b]pyridin-3-yl]pyridin-3-yl}-N-(2,2,2-trifluoroethyl)-D-valinamide | Calc'd 475.2, found 475.2 |

TABLE 11-continued

| Example Number | Structure | IUPAC Name | Exact Mass [M + H]+ |
|---|---|---|---|
| 9-8 | 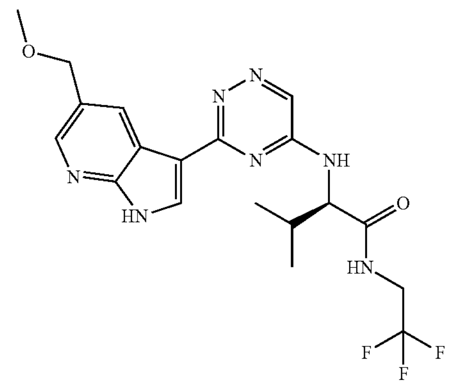 [SMILES: COCc1cnc2[nH]cc(-c3nncc(N[C@@H](C(=O)NCC(F)(F)F)C(C)C)n3)c2c1] | N~2~-{3-[5-(methoxymethyl)-1H-pyrrolo[2,3-b]pyridin-3-yl]-1,2,4-triazin-5-yl}-N-(2,2,2-trifluoroethyl)-D-valinamide | Calc'd 438.2, found 438.1 |
| 9-9 | 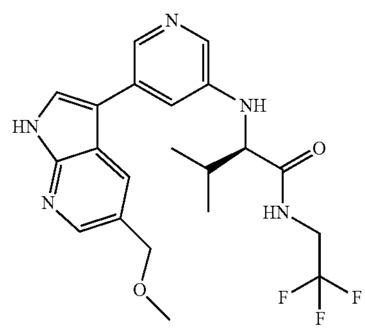 [SMILES: COCc1cnc2[nH]cc(-c3cncc(N[C@@H](C(=O)NCC(F)(F)F)C(C)C)c3)c2c1] | N~2~-{5-[5-(methoxymethyl)-1H-pyrrolo[2,3-b]pyridin-3-yl]pyridin-3-yl}-N-(2,2,2-trifluoroethyl)-D-valinamide | Calc'd 436.2, found 436.1 |

Examples generated via General Scheme 8:

Example 10-1

N-((3-(5-(3-methyl-1-oxo-1-(2,2,2-trifluoroethylamino)butan-2-ylamino)pyridin-3-yl)-1H-pyrrolo[2,3-b]pyridin-5-yl)methyl)cyclopentanecarboxamide (10-1)

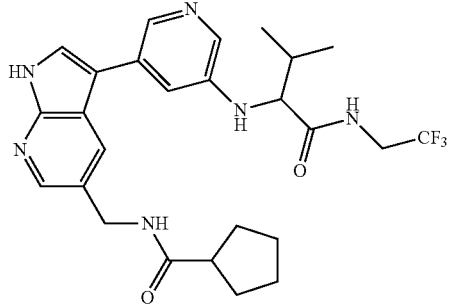

10-1

Step 1 2-(5-(5-(cyano)-1-((2-(trimethylsilyl)ethoxy)methyl)-1H-pyrrolo[2,3 b]pyridin-3-yl)pyridin-3-ylamino)-3-methyl-N-(2,2,2-trifluoroethyl)butanamide (10-1a)

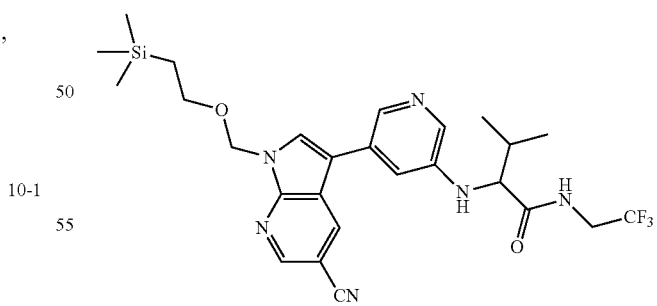

10-1a 2-(5-(5-(cyano)-1-((2-(trimethylsilyl)ethoxy)methyl)-1H-pyrrolo[2,3 b]pyridin-3-yl)pyridin-3-ylamino)-3-methyl-N-(2,2,2-trifluoroethyl)butanamide (9-1a) was prepared in a manner similar to that utilized for the preparation of (2-1a) utilizing of 5-cyano-3-(4,4,5,5-tetramethyl-1,3,2-dioxaborolan-2-yl)-1-((2-(trimethylsilyl)ethoxy)methyl)-1H-pyrrolo[2,3-b]pyridine. LRMS (ESI) m/z 547.5 [(M+H)+; calcd for $C_{26}H_{33}F_3N_6O_2Si$: 547.6

Step 2 2-(5-(5-(aminomethyl)-1-((2-(trimethylsilyl)ethoxy)methyl)-1H-pyrrolo[2,3 b]pyridin-3-yl)pyridin-3-ylamino)-3-methyl-N-(2,2,2-trifluoroethyl)butanamide (10-1b)

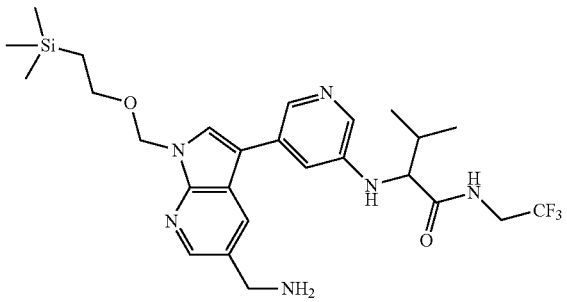

To a solution of the 2-(5-(5-cyano-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide, (9-1a) (110 mg, 187 mmol) 10-1a in ethanol (5.0 ml) was added Raney Nickel (2.197 mg, 0.037 mmol) Ammonium hydroxide (0.260 µl, 1.871 µmol) was added and the flask evacuated and backfilled with hydrogen gas 3 times. The mixture was stirred under hydrogen for 17 hrs. The reaction was purged with nitrogen, diluted with ethanol and filtered through a pad of celite. The filtrate was concentrated and oil purified by Reverse phase HPLC (Water:ACN w/0.1% TFA, C-18, 35-65% gradient). The pure fractions concentrated to remove acetonitrile and mixture neutralized with saturated sodium bicarbonate. The product was extracted with ethyl acetate (3×20 mL). The organics were dried with sodium sulfate, filtered and concentrated to afford the product 10-1b as a solid (50 mg, 47%).

LRMS (ESI) m/z 551.1 [(M+H)$^+$; calcd for $C_{26}H_{37}F_3N_6O_2Si$: 551.3

Step 3 2-(5-(5-(aminomethyl)-1H-pyrrolo[2,3-b]pyridin-3-yl)pyridin-3-ylamino)-3-methyl-N-(2,2,2-trifluoroethyl)butanamide (10-1c)

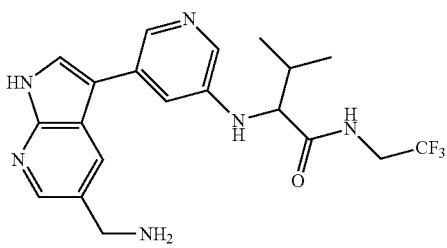

To 2-(5-(5-(aminomethyl)-1-((2-(trimethylsilyl)ethoxy)methyl)-1H-pyrrolo[2,3-b]pyridin-3-yl)pyridin-3-ylamino)-3-methyl-N-(2,2,2-trifluoroethyl)butanamide 10-1b (211 mg, 0.364 mmol) dissolved in dichlormethane (2.0 ml) was added TFA (2.0 ml, 26.0 mmol). The reaction stirred at room temp for 1.5 hrs, concentrated and the residue dissolved in MeOH (2.0 ml). NaOH (0.255 ml, 2.55 mmol) and ethylenediamine (0.049 ml, 0.728 mmol) were added and the reaction stirred for 2 hrs at room temperature. The reaction was then acidified with trifluoroacetic acid, filtered and purified by RP-HPLC (water:acetonitrile w/0.1% TFA, C-18, 15-50%). The pure fractions concentrated to remove acetonitrile and mixture neutralized with saturated sodium bicarbonate. The product was extracted with ethyl acetate (3×10 mL). The combined organics were then washed with brine, dried with sodium sulfate, filtered and concentrated to afford the product 10-1c (140 mg, 89%).

LRMS (ESI) m/z 421.0 [(M+H)$^+$; calcd for $C_{20}H_{23}F_3N_6O$: 421.2

Step 4 N-((3-(5-(3-methyl-1-oxo-1-(2,2,2-trifluoroethylamino)butan-2-ylamino)pyridin-3-yl)-1H-pyrrolo[2,3-b]pyridin-5-yl)methyl)cyclopentanecarboxamide (10-1)

2-(5-(5-(aminomethyl)-1H-pyrrolo[2,3-b]pyridin-3-yl)pyridin-3-ylamino)-3-methyl-N-(2,2,2-trifluoroethyl)butanamide 10-1c (30 mg, 0.071 mmol) was added to DMSO (0.5 ml) followed by the addition of diisopropylethylamine (0.031 ml, 0.178 mmol). Cyclopentanecarbonyl chloride (9.4 mg, 0.086 mmol) was added and the reaction stirred at room temperature for 3 hrs. The reaction was quenched by addition of methanol. The mixture was diluted with DMSO, filtered and purified by RP-HPLC (water:acetonitrile w/0.1% TFA, C-18, 15-50%). The pure fractions concentrated to remove acetonitrile and mixture neutralized with saturated sodium bicarbonate. The product was extracted with ethyl acetate (3×10 mL). The combined organics were then washed with brine, dried with sodium sulfate, filtered and concentrated to afford the product 10-1. LRMS (ESI) m/z 517.2 [(M+H)$^+$; calcd for $C_{26}H_{31}F_3N_6O_2$: 517.3

The following examples, 10-2 through 10-13 as shown in Table 12 were prepared in an analogous manner of that described above using materials that are commercially available or known, or that can be prepared using procedures known in the art or by generally following procedures described herein for various intermediates.

TABLE 12

| Example Number | Structure | IUPAC Name | Exact Mass [M + H]+ |
|---|---|---|---|
| 10-2 | 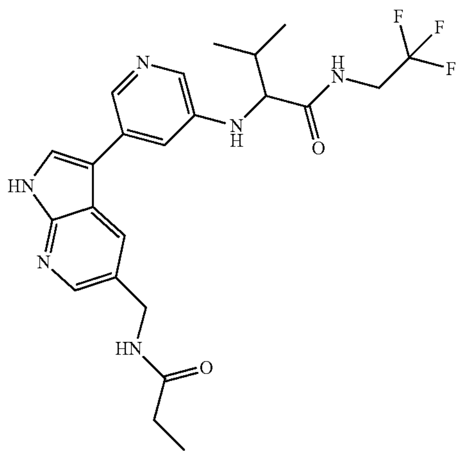 [SMILES: CCC(=O)NCc1cnc2[nH]cc(-c3cncc(NC(C(=O)NCC(F)(F)F)C(C)C)c3)c2c1] | N~2~-(5-{5-[(propanoylamino)methyl]-1H-pyrrolo[2,3-b]pyridin-3-yl}pyridin-3-yl)-N-(2,2,2-trifluoroethyl)valinamide | Calc'd 477.2, found 477.2 |
| 10-3 | 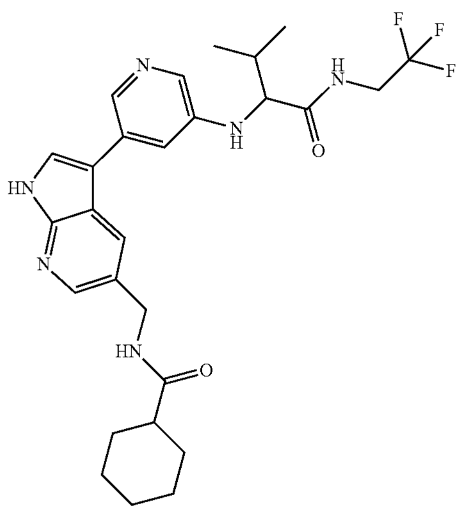 [SMILES: CC(C)C(Nc1cncc(-c2c[nH]c3ncc(CNC(=O)C4CCCCC4)cc23)c1)C(=O)NCC(F)(F)F] | N-({3-[5-({2-methyl-1-[(2,2,2-trifluoroethyl)carbamoyl]propyl}amino)pyridin-3-yl]-1H-pyrrolo[2,3-b]pyridin-5-yl}methyl)cyclohexanecarboxamide | Calc'd 531.3, found 531.2 |
| 10-4 | 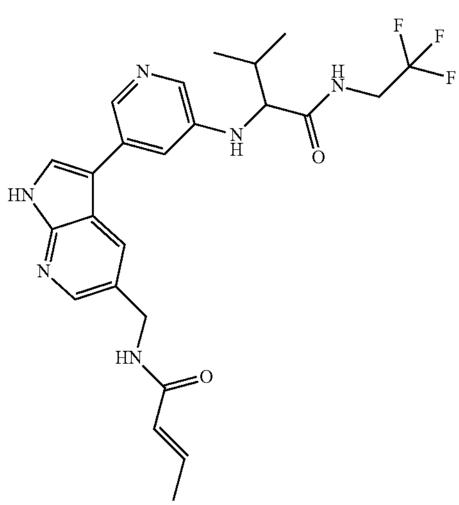 [SMILES: C/C=C/C(=O)NCc1cnc2[nH]cc(-c3cncc(NC(C(=O)NCC(F)(F)F)C(C)C)c3)c2c1] | N~2~-[5-(5-{[(2E)-but-2-enoylamino]methyl}-1H-pyrrolo[2,3-b]pyridin-3-yl)pyridin-3-yl]-N-(2,2,2-trifluoroethyl)valinamide | Calc'd 489.2, found 489.2 |

TABLE 12-continued

| Example Number | Structure | IUPAC Name | Exact Mass [M + H]+ |
|---|---|---|---|
| 10-5 | 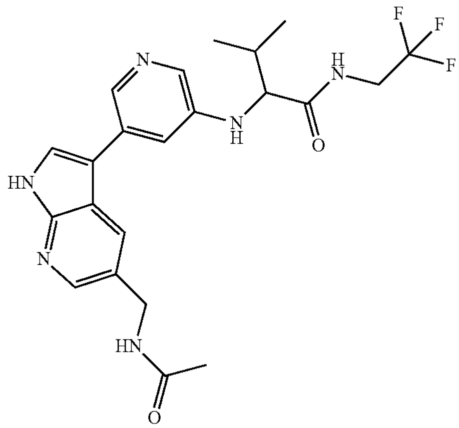 [SMILES: CC(=O)NCc1cnc2[nH]cc(-c3cncc(NC(C(=O)NCC(F)(F)F)C(C)C)c3)c2c1] | N~2~-(5-{5-[(acetylamino)methyl]-1H-pyrrolo[2,3-b]pyridin-3-yl}pyridin-3-yl)-N-(2,2,2-trifluoroethyl)valinamide | Calc'd 463.2, found 463.2 |
| 10-6 | 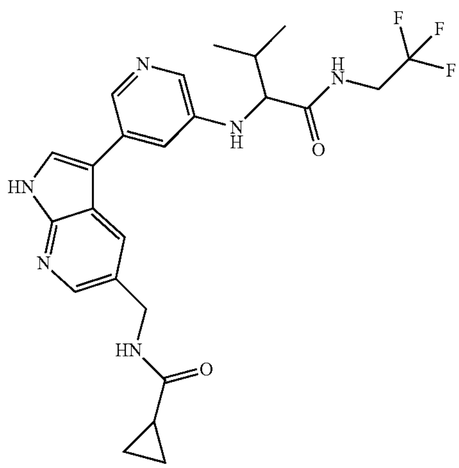 [SMILES: CC(C)C(Nc1cncc(-c2c[nH]c3ncc(CNC(=O)C4CC4)cc23)c1)C(=O)NCC(F)(F)F] | N~2~-[5-(5-{[(cyclopropylcarbonyl)amino]methyl}-1H-pyrrolo[2,3-b]pyridin-3-yl)pyridin-3-yl]-N-(2,2,2-trifluoroethyl)valinamide | Calc'd 489.2, found 489.2 |
| 10-7 | 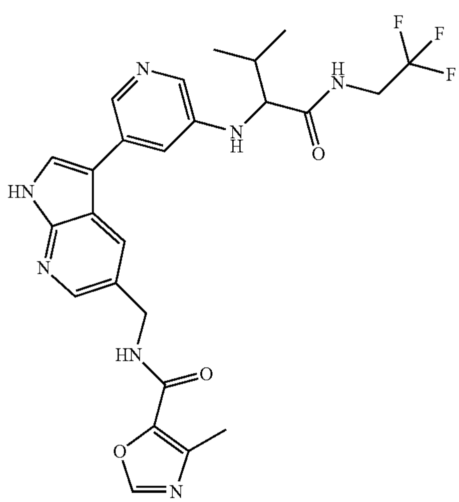 [SMILES: Cc1ncoc1C(=O)NCc1cnc2[nH]cc(-c3cncc(NC(C(=O)NCC(F)(F)F)C(C)C)c3)c2c1] | N~2~-{5-[5-({[(4-methyl-1,3-oxazol-5-yl)carbonyl]amino}methyl)-1H-pyrrolo[2,3-b]pyridin-3-yl]pyridin-3-yl}-N-(2,2,2-trifluoroethyl)valinamide | Calc'd 530.2, found 530.2 |

TABLE 12-continued

| Example Number | Structure | IUPAC Name | Exact Mass [M + H]+ |
|---|---|---|---|
| 10-8 | 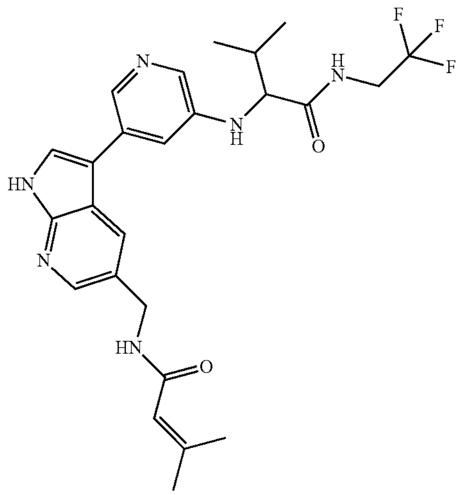 [SMILES: CC(C)=CC(=O)NCc1cnc2[nH]cc(-c3cncc(NC(C(=O)NCC(F)(F)F)C(C)C)c3)c2c1] | N~2~-[5-(5-{[(3-methylbut-2-enoyl)amino]methyl}-1H-pyrrolo[2,3-b]pyridin-3-yl)pyridin-3-yl]-N-(2,2,2-trifluoroethyl)valinamide | Calc'd 503.2, found 503.2 |
| 10-9 | 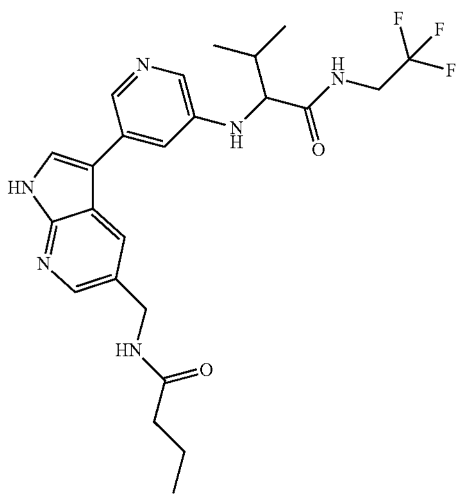 [SMILES: CCCC(=O)NCc1cnc2[nH]cc(-c3cncc(NC(C(=O)NCC(F)(F)F)C(C)C)c3)c2c1] | N~2~-(5-{5-[(butanoylamino)methyl]-1H-pyrrolo[2,3-b]pyridin-3-yl}pyridin-3-yl)-N-(2,2,2-trifluoroethyl)valinamide | Calc'd 491.2, found 491.2 |
| 10-10 | 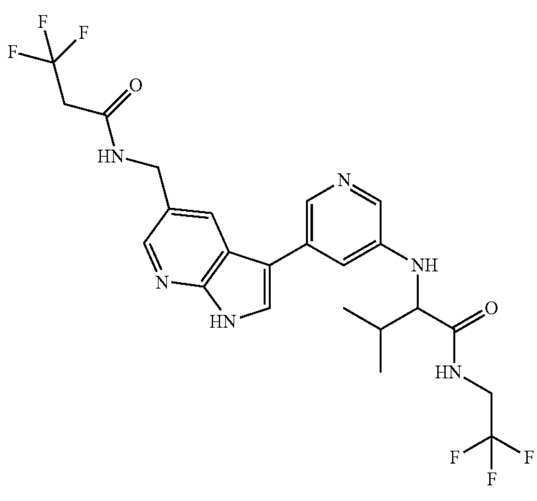 [SMILES: CC(C)C(Nc1cncc(-c2c[nH]c3ncc(CNC(=O)CC(F)(F)F)cc23)c1)C(=O)NCC(F)(F)F] | N-(2,2,2-trifluoroethyl)-N~2~-[5-(5-{[(3,3,3-trifluoropropanoyl)amino]methyl}-1H-pyrrolo[2,3-b]pyridin-3-yl)pyridin-3-yl]valinamide | Calc'd 531.2, found 531.1 |

TABLE 12-continued

| Example Number | Structure | IUPAC Name | Exact Mass [M + H]+ |
|---|---|---|---|
| 10-11 | 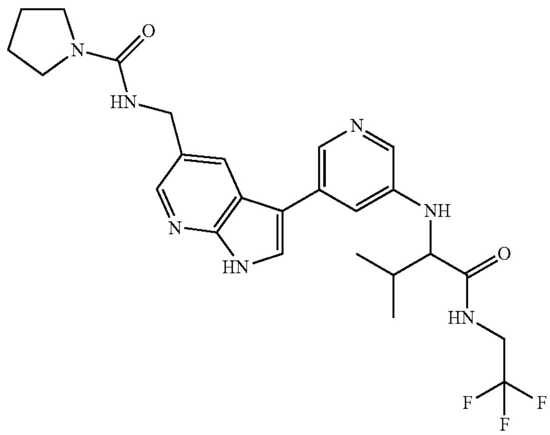 [SMILES: CC(C)C(Nc1cncc(-c2c[nH]c3ncc(CNC(=O)N4CCCC4)cc23)c1)C(=O)NCC(F)(F)F] | N~2~-[5-(5-{[(pyrrolidin-1-ylcarbonyl)amino]methyl}-1H-pyrrolo[2,3-b]pyridin-3-yl)pyridin-3-yl]-N-(2,2,2-trifluoroethyl)valinamide | Calc'd 518.2, found 518.0 |

Biological Assays

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDE-PEGDYFEWLW-NH2 (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 µL of 1.11× enzyme and 1.11× substrate in 1× assay buffer (Invitrogen kinase buffer #PV3189, 2 mM DTT, 0.05% BSA) were added to the wells and shaken and then preincubated for 30 minutes at room temperature to allow compound binding to equilibrate. After equilibration, 2 µL of 10×ATP in 1× assay buffer was added to initiate the kinase reaction and the plates were shaken and then incubated at room temperature for 120 minutes. At the end of the incubation, 20 µL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final reaction conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

Biological Data

Examples of the instant invention were evaluated in JAK2 and JAK3 in vitro binding assays. Table 13 tabulates the biological data disclosed for the instant invention as a range of JAK2 and JAK3 $IC_{50}$ values (A: $IC_{50}$≤10 nM; B: 10 nM>$IC_{50}$≤500 nM C: $IC_{50}$>500 nM).

TABLE 13

| Examples | JAK3 IC50 | JAK2 IC50 |
|---|---|---|
| 1-1 | A | B |
| 1-2 | A | B |
| 1-3 | A | B |
| 1-4 | A | B |
| 1-5 | B | B |
| 1-6 | A | B |
| 1-7 | A | B |
| 1-8 | B | B |
| 1-9 | A | B |
| 1-10 | B | B |
| 1-11 | B | B |
| 1-12 | B | B |
| 1-13 | A | B |
| 1-14 | A | B |
| 1-15 | A | B |
| 1-16 | A | B |
| 1-17 | A | B |
| 1-18 | A | B |
| 1-19 | B | B |
| 1-20 | A | B |
| 1-21 | B | C |
| 1-22 | B | B |
| 1-23 | B | B |

TABLE 13-continued

| Examples | JAK3 IC50 | JAK2 IC50 |
|---|---|---|
| 1-24 | A | B |
| 1-25 | A | B |
| 1-26 | B | B |
| 1-27 | A | B |
| 1-28 | A | B |
| 1-29 | A | B |
| 1-30 | B | B |
| 1-31 | A | B |
| 1-32 | A | B |
| 1-33 | A | B |
| 1-34 | A | C |
| 1-35 | A | B |
| 1-36 | B | C |
| 1-37 | A | B |
| 1-38 | A | B |
| 1-39 | A | B |
| 1-40 | A | A |
| 1-41 | A | B |
| 1-42 | A | B |
| 1-43 | A | B |
| 1-44 | A | B |
| 1-45 | A | B |
| 1-46 | A | B |
| 1-47 | A | B |
| 1-48 | A | B |
| 1-49 | A | B |
| 1-50 | A | B |
| 1-51 | A | A |
| 1-52 | A | B |
| 2-1 | A | B |
| 2-2 | A | B |
| 2-3 | A | B |
| 2-4 | A | B |
| 2-5 | A | B |
| 2-6 | A | B |
| 2-7 | A | B |
| 2-8 | A | B |
| 2-9 | A | B |
| 2-10 | A | B |
| 2-11 | A | B |
| 2-12 | A | B |
| 2-13 | B | C |
| 2-14 | A | B |
| 2-15 | A | B |
| 2-16 | A | B |
| 2-17 | A | B |
| 2-18 | A | B |
| 3-1 | B | C |
| 3-2 | A | A |
| 3-3 | A | B |
| 3-4 | A | A |
| 3-5 | A | A |
| 3-6 | A | B |
| 3-7 | A | B |
| 3-8 | A | B |
| 3-9 | A | B |
| 3-10 | A | B |
| 3-11 | B | C |
| 3-12 | A | A |
| 3-13 | B | C |
| 3-14 | A | A |
| 4-1 | A | B |
| 4-2 | B | C |
| 5-1 | B | B |
| 5-2 | A | B |
| 5-3 | B | B |
| 5-4 | B | C |
| 5-5 | B | B |
| 5-6 | A | B |
| 5-7 | A | B |
| 5-8 | A | B |
| 6-1 | A | B |
| 6-2 | A | B |
| 6-3 | A | B |
| 6-4 | A | B |
| 6-5 | A | B |
| 7-1 | B | B |
| 7-2 | B | B |
| 7-3 | B | B |
| 8-1 | A | A |
| 8-2 | B | B |
| 8-3 | A | A |
| 9-1 | B | B |
| 9-2 | B | B |
| 9-3 | A | B |
| 9-4 | A | B |
| 9-5 | A | B |
| 9-6 | A | B |
| 9-7 | B | B |
| 9-8 | B | B |
| 9-9 | A | B |
| 10-1 | B | C |
| 10-2 | B | C |
| 10-3 | B | C |
| 10-4 | A | B |
| 10-5 | B | C |
| 10-6 | A | B |
| 10-7 | B | C |
| 10-8 | B | B |
| 10-9 | B | C |
| 10-10 | B | C |
| 10-11 | B | C |

What is claimed is:
1. A compound of formula I

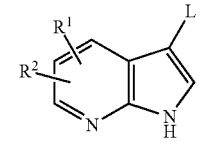

or a pharmaceutically acceptable salt thereof; wherein L is chosen from:

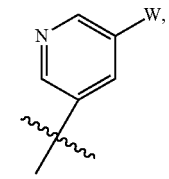

wherein L is substituted with 0, 1, 2, or 3 independently chosen $R^5$;
W is chosen from $C_{1-10}$ alkylamino, a 3-15 member saturated, unsaturated or partially saturated monocyclic or bicyclic ring system containing 0, 1, 2, 3, or 4 atoms independently selected from N, O, or S, and —$NR^6R^6$ wherein two $R^6$ and the nitrogen to which they are attached can optionally form a -4, -5, or -6 member saturated ring system, and wherein W is substituted with 0, 1, 2 or 3 independently chosen $R^5$;
Calkoxy,
C alkylsulfonyl,
(C alkyl)sulfonylamino,
$R^6$ is independently selected from:
hydrogen,
(carbonyl)$_{0-1}$$C_{1-10}$ alkyl,
(carbonyl)$_{0-1}$$C_{2-10}$ alkenyl, (carbonyl)$_{0-1}$C$_{2-10}$ alkynyl,
C$_{0-10}$ alkylcarbonyl(oxy)$_{0-1}$C$_{0-10}$ alkyl,
C$_{1-10}$ alkyl(oxy)$_{0-1}$carbonylC$_{0-10}$ alkyl,
C$_{2-10}$ alkenylcarbonyl,
C$_{2-10}$ alkynylcarbonyl,
(C$_{1-10}$)alkyl(oxy)$_{0-1}$C$_{0-10}$ alkyl,
aryl(oxy)$_{0-1}$C$_{0-10}$ alkyl,
(C$_{3-8}$)heteroaryl(oxy)$_{0-1}$C$_{0-10}$ alkyl,
C$_{3-8}$ cycloalkyl(oxy)$_{0-1}$C$_{0-10}$ alkyl,
(C$_{3-8}$)heterocycloalkyl(oxy)$_{0-1}$C$_{0-10}$ alkyl,
(C$_{1-10}$)heteroalkyl(oxy)$_{0-1}$C$_{0-10}$ alkyl,
C$_{0-10}$ alkyl(oxy)$_{0-1}$C$_{0-10}$ alkylaminocarbonylC$_{0-10}$ alkyl,
C$_{0-10}$ alkylaminocarbonylC$_{1-10}$ heteroalkyl,
C$_{0-10}$ alkylaminocarbonyl(C$_{3-8}$)heterocycloalkylC$_{0-10}$ alkyl,
C$_{0-10}$ alkylaminocarbonyl(C$_{3-8}$)heteroarylC$_{0-10}$ alkyl,
C$_{0-10}$ alkylaminocarbonyl(C$_{3-8}$)cycloalkylC$_{0-10}$ alkyl,
C$_{0-10}$ alkylaminocarbonylarylC$_{0-10}$ alkyl,
hydroxy C$_{0-10}$alkyl,
C$_{0-10}$ alkylsulfonyl,
aryl C$_{1-10}$ alkylsulfonyl,
C$_{3-8}$ heterocyclyl C$_{1-10}$ alkylsulfonyl,
C$_{3-8}$ heterocycloalkyl C$_{1-10}$ alkylsulfonyl,
C$_{3-8}$ cycloalkyl C$_{1-10}$ alkylsulfonyl, and
C$_{1-6}$ haloalkyl;
R$^1$, R$^2$ and R$^5$ are independently chosen from (1-methylethyl)carbamoyl, (2-methoxyethyl)carbamoyl, (2-hydroxy-ethyl)carbamoyl, (tetrahydro-2H-pyran-4-yl)carbamoyl, azetidin-1-ylcarbonyl, 2-methylpropylcarbamoyl, carbamoyl, (tetrahydrothiophen-3-yl)carbamoyl, (1H-pyrazol-5-ylmethyl)carbamoyl, (4-hydroxypiperidin-1-yl)carbonyl, cyclopropylmethylcarbamoyl, sulfamoyl, dimethylsulfamoyl, amino, acetylamino, sulfonylamino, propanoylamino, (propan-2-ylcarbamoyl)amino, (propylcarbamoyl)amino, carbamoylamino, methylcarbamate, ethylcarbamate, (1-methylethyl)carbamate, 1H-pyrazolyl, tertbutoxymethyl, (methoxyethyl)piperazinyl, 2-morpholin-4-ylethoxy)methyl, (prop-2-en-1-yloxy)methyl, piperidinylmethoxy, pyrrolidin-1-ylmethyl, methoxymethyl, cyclopentanylcarboxamidomethyl, propanoylamino)methyl, (cyclohexanecarbonylamino)methyl, but-2-enoylaminomethyl, (cyclopropylcarbonyl)aminomethyl, (1,3-oxazol-5-yl)carbonylaminomethyl, (butanoylamino)methyl, (pyrrolidin-1-ylcarbonyl)aminomethyl, halogen, cyano, carbamoyl, methoxy, trifluoroethyl, methylsulfonyl, hydroxyl, 2-methoxyethoxy, methylethoxy, benzyloxy, cyclopentyloxy, cyclopropylmethoxy, 2-phenylethoxy, 2,3-dihydro-1H-inden-2-yloxy, tetrahydro-2H-pyran-4-yloxy, 2-oxopyrrolidin-1-yl)ethoxy, pyridin-3-ylmethoxy, 2-pyridin-2-ylethoxy, 2-(dimethylamino)ethoxy, 3-(dimethylamino)propoxy, 2-morpholin-4-ylethoxy, 1-methylpiperidin-4-yl)oxy, 2-(piperazin-1-yl)ethoxy, hydrogen, and piperidin-4-yl)methoxy, wherein R$^1$, R$^2$ and R$^5$ are independently substituted with 0, 1, 2, or 3 substituents R$^3$;
wherein R$^1$, R$^2$, R$^5$ and R$^6$ are independently substituted with 0, 1, 2, or 3, substituents R$^3$ chosen from: halogen, C$_1$-C$_{10}$ alkyl, CF$_3$, NH$_2$, N(C$_1$-C$_6$ alkyl)$_2$, NO$_2$, —(C$_{0-6}$)alkylCN, —OH, —O(C$_1$-C$_6$ alkyl), C$_3$-C$_{10}$ cycloalkyl, C$_2$-C$_6$ alkenyl, C$_2$-C$_6$ alkynyl, (C$_0$-C$_6$ alkyl)S(O)$_{0-2}$—, (C$_0$-C$_6$ alkyl)S(O)$_{0-2}$(C$_0$-C$_6$ alkyl)-, (C$_0$-C$_6$ alkyl)C(O)NH—, H$_2$N—C(NH)—, —O(C$_1$-C$_6$ alkyl)CF$_3$, (C$_0$-C$_6$ alkyl)C(O)—, (C$_0$-C$_6$ alkyl)OC(O)—, (C$_0$-C$_6$ alkyl)O(C$_1$-C$_6$ alkyl)-, (C$_0$-C$_6$ alkyl)C(O)$_{1-2}$(C$_0$-C$_6$ alkyl)-, (C$_0$-C$_6$ alkyl)OC(O)NH—, —NH(C$_1$-C$_6$ alkyl) NHC(O)NH(C$_1$-C$_6$ alkyl), NHC(O)OC$_1$-C$_6$ alkyl, —NH(C$_1$-C$_6$ alkyl)NHSO$_2$(C$_1$-C$_6$ alkyl), —(C$_0$-C$_6$ alkyl)NHSO$_2$(C$_1$-C$_6$ alkyl), C$_{1-10}$alkoxy, —CO$_2$(C$_{0-10}$ alkyl), Oxo (=O), trifluoromethyl, trifluoroethyl, C$_{1-10}$ alkylsulfonyl, —SO$_2$N(C$_{1-6}$alkyl)$_{1-2}$, —SO$_2$CF$_3$, —SO$_2$CF$_2$H, —C$_{1-10}$ alkylsulfinyl, —O$_{(0-1)}$(C$_{1-10}$)haloalkyl, aryl, heteroaryl, heterocyclyl, halo-aryl, halo-heterocyclyl, cyano-aryl, cyano-heteroaryl, and cyano-heterocyclyl.

2. A compound according to claim 1, wherein W is chosen from C$_{1-10}$ alkylamino, and —NR$^6$R$^6$, wherein two R$^6$ and the nitrogen to which they are attached can optionally form a -4, -5, or -6 member saturated ring system and wherein W is substituted with 0, 1, 2 or 3 independently chosen R$^5$.

3. A compound according to claim 1 wherein W is chosen from a 3-15 member saturated, unsaturated or partially saturated monocyclic or bicyclic ring system containing 0, 1, 2, 3, or 4 atoms independently selected from N, O, or S, —NR$^6$R$^6$ wherein two R$^6$ and the nitrogen to which they are attached can optionally form a -4, -5, or -6 member saturated ring system, and wherein W is substituted with 0, 1, 2 or 3 independently chosen R$^5$.

4. A compound selected from the group consisting of:
(2R)-2-{[5-(5-chloro-1H-pyrrolo[2,3-b]pyridin-3-yl)pyridin-3-yl]amino}-3-methyl-N-(2,2,2-trifluoroethyl)butanamide;
2-{[5-(5-fluoro-1H-pyrrolo[2,3-b]pyridin-3yl)pyridin-3-yl]amino}-3-methyl-N-(2,2,2-trifluoroethyl)butanamide;
N~2~-[3-(5-chloro-1H-pyrrolo[2,3-b]pyridin-3-yl)-1,2,4-triazin-5-yl]-N-(2,2,2-trifluoroethyl)-D-valinamide;
7-[3-(5-chloro-1H-pyrrolo[2,3-b]pyridin-3-yl)-1,2,4-triazin-5-yl]-8-methyl-3-(trifluoromethyl)-5,6,7,8-tetrahydroimidazo[1,2-a]pyrazine;
5-chloro-3-{5-[2-(1,3-thiazol-2-yl)pyrrolidin-1-yl]-1,2,4-triazin-3-yl}-1H-pyrrolo[2,3-b]pyridine;
N~2~-[3-(5-fluoro-1H-pyrrolo[2,3-b]pyridin-3-yl)-1,2,4-triazin-5-yl]-2-methyl-N-(2,2,2-trifluoroethyl)alaninamide;
N~2~-[3-(5-cyano-1H-pyrrolo[2,3-b]pyridin-3-yl)-1,2,4-triazin-5-yl]-2-methyl-N-(2,2,2-trifluoroethyl)alaninamide;
N~2~-[3-(5-fluoro-1H-pyrrolo[2,3-b]pyridin-3-yl)-1,2,4-triazin-5-yl]-N-(2,2,2-trifluoroethyl)-D-alaninamide;
N~2~-[3-(5-cyano-1H-pyrrolo[2,3-b]pyridin-3-yl)-1,2,4-triazin-5-yl]N-(2,2,2-trifluoroethyl)-D-alaninamide;
7-[3-(5-fluoro-1H-pyrrolo[2,3-b]pyridin-3-yl)-1,2,4-triazin-5-yl]-8-methyl-3-(trifluoromethyl)-5,6,7,8-tetrahydroimidazo[1,2-a]pyrazine;
5-fluoro-3-{5-[2-(1,3-thiazol-2-yl)pyrrolidin-1-yl]-1,2,4-triazin-3-yl}-1H-pyrrolo[2,3-b]pyridine;
3-{5-[2-(1,3-thiazol-2-yl)pyrrolidin-1-yl]-1,2,4-triazin-3-yl}-1H-pyrrolo[2,3-b]pyridine-5-carbonitrile;
3-[5-({1,1-dimethyl-2-oxo-2-[(2,2,2-trifluoroethyl)amino]ethyl}amino)-1,2,4-triazin-3-yl]-1H-pyrrolo[2,3-b]pyridine-5-carboxamide;
3-[5-({(1R)-1-methyl-2-oxo-2-[(2,2,2-trifluoroethyl)amino]ethyl}amino)-1,2,4-triazin-3-yl]-1H-pyrrolo[2,3-b]pyridine-5-carboxamide;
3-{5-[8-methyl-3-(trifluoromethyl)-5,6-dihydroimidazo[1,2-a]pyrazin-7(8H)-yl]-1,2,4-triazin-3-yl}-1H-pyrrolo[2,3-b]pyridine-5-carboxamide;
N~2~-[3-(5-fluoro-1H-pyrrolo[2,3-b]pyridin-3-yl)-1,2,4-triazin-5-yl]-N-(2,2,2-trifluoroethyl)-D-valinamide;
N~2~-[3-(5-cyano-1H-pyrrolo[2,3-b]pyridin-3-yl)-1,2,4-triazin-5-yl]-N-(2,2,2-trifluoroethyl)-D-valinamide;

3-[5-({(1R)-2-methyl-1-[(2,2,2-trifluoroethyl)carbamoyl]propyl}amino)-1,2,4-triazin-3-yl]-1H-pyrrolo[2,3-b]pyridine-5-carboxamide;
(1S,2R)-2-{[3-(5-chloro-1H-pyrrolo[2,3-b]pyridin-3-yl)-1,2,4-triazin-5-yl]amino}-N-(2,2,2-trifluoroethyl)cyclohexanecarboxamide;
N~2~-[3-(5-methoxy-1H-pyrrolo[2,3-b]pyridin-3-yl)-1,2,4-triazin-5-yl]-N-(2,2,2-trifluoroethyl)-D-valinamide;
(1S,2R)-2-{([3-(5-fluoro-1H-pyrrolo[2,3-b]pyridin-3-yl)-1,2,4-triazin-5-yl]amino}-N-(2,2,2-trifluoroethyl)cyclohexanecarboxamide;
(1S,2R)-2-{[3-(5-cyano-1H-pyrrolo[2,3-b]pyridin-3-yl)-1,2,4-triazin-5-yl]amino}-N-(2,2,2-trifluoroethyl)cyclohexanecarboxamide;
3-[5-({(1R,2S)-2-[(2,2,2-trifluoroethyl)carbamoyl]cyclohexyl}amino)-1,2,4-triazin-3-yl]-1H-pyrrolo[2,3-b]pyridine-5-carboxamide;
N~2~-[6-(5-chloro-1H-pyrrolo[2,3-b]pyridin-3-yl)pyridazin-4-yl]-N-(2,2,2-trifluoroethyl)-D-alaninamide;
N-(2,2,2-trifluoroethyl)-N~2~-{6-[5-(trifluoromethyl)-1H-pyrrolo[2,3-b]pyridin-3-yl]pyridazin-4-yl}-D-alaninamide;
5-chloro-3-{5-[2-(1,3-thiazol-2-yl)pyrrolidin-1-yl]pyridazin-3-yl}-1H-pyrrolo[2,3-b]pyridine;
N~2~-[5-(5-chloro-1H-pyrrolo[2,3-b]pyridin-3-yl)pyridin-3-yl]-2-methyl-N-(2,2,2-trifluoroethyl)alaninamide;
5-chloro-3-{5-[2-(1,3-thiazol-2-yl)pyrrolidin-1-yl]pyridin-3-yl}-1H-pyrrolo[2,3-b]pyridine;
N~2~-[5-(5-chloro-1H-pyrrolo[2,3-b]pyridin-3-yl)pyridin-3-yl]-N-(2,2,2-trifluoroethyl)-D-alaninamide;
N~2~-[5-(5-fluor-H-pyrrolo[2,3-b]pyridin-3-yl)pyridin-3-yl]-N-(2,2,2-trifluoroethyl)-D-alaninamide;
N~2~-[5-(5-methoxy-1H-pyrrolo[2,3-b]pyridin-3-yl)pyridin-3-yl]N-(2,2,2-trifluoroethyl)-D-alaninamide;
N~2~-[5-(5-cyano-1H-pyrrolo[2,3-b]pyridin-3-yl)pyridin-3-yl]-N-(2,2,2-trifluoroethyl)-D-alaninamide;
R)-2-{[5-(5-chloro-1H-pyrrolo[2,3-b]pyridin-3-yl)pyridin-3-yl]amino}-N-(2,2,2-trifluoroethyl)cyclohexanecarboxamide;
N~2~-{5-[5-(methylsulfonyl)-1H-pyrrolo[2,3-b]pyridin-3-yl]pyridin-3-yl}-N-(2,2,2-trifluoroethyl)-D-alaninamide;
2-[6-(5-chloro-1H-pyrrolo[2,3-b]pyridin-3-yl)-1H-pyrrolo[3,2-b]pyridin-1-yl]-N-(2,2,2-trifluoroethyl)propanamide;
N~2~-[5-(5-chloro-4-fluoro-1H-pyrrolo[2,3-b]pyridin-3-yl)pyridin-3-yl]-N-(2,2,2-trifluoroethyl)-D-alaninamide;
(1S,2R)-2-{[5-(5-fluoro-1H-pyrrolo[2,3-b]pyridin-3-yl)pyridin-3-yl]amino}-N-(2,2,2-trifluoroethyl)cyclohexanecarboxamide;
(1S,2R)-2-{[5-(5-cyano-1H-pyrrolo[2,3-b]pyridin-3-yl)pyridin-3-yl]amino}-N-(2,2,2-trifluoroethyl)cyclohexanecarboxamide;
N~2~-[5-(5-chloro-1H-pyrrolo[2,3-b]pyridin-3-yl)-2-fluoropyridin-3-yl]-N-(2,2,2-trifluoroethyl)alaninamide;
3-[5-({(1R,2S)-2-[(2,2,2-trifluoroethyl)carbamoyl]cyclohexyl}amino)pyridin-3-yl]-1H-pyrrolo[2,3-b]pyridine-5-carboxamide;
N~2~-[5-(5-cyano-1H-pyrrolo[2,3-b]pyridin-3-yl)pyridin-3-yl]-N-(2,2,2-trifluoroethyl)valinamide;
3-[5-({2-methyl-1-[(2,2,2-trifluoroethyl)carbamoyl]propyl}amino)pyridin-3-yl]-1H-pyrrolo[2,3-b]pyridine-5-carboxamide;
N~2~-[5-(5-fluoro-1H-pyrrolo[2,3-b]pyridin-3-yl)pyridin-3-yl]-2-methyl-N-(2,2,2-trifluoroethyl)alaninamide;
N~2~-[5-(5-cyan-1H-pyrrolo[2,3-b]pyridin-3-yl)pyridin-3-yl]-2-methyl-N-(2,2,2-trifluoroethyl)alaninamide;
N~2~-[5-(5-methoxy-1H-pyrrolo[2,3-b]pyridin-3-yl)pyridin-3-yl]-N-(2,2,2-trifluoroethyl)valinamide;
3-[5-({(1R)-1-methyl-2-oxo-2-[(2,2,2-trifluoroethyl)amino]ethyl}amino)pyridin-3-yl]-1H-pyrrolo[2,3-b]pyridine-5-carboxamide;
3-[5-({1,1-dimethyl-2-oxo-2-[(2,2,2-trifluoroethyl)amino]ethyl}amino)pyridin-3-yl]-1H-pyrrolo[2,3-b]pyridine-5-carboxamide;
2-{[5-(5-chloro-1H-pyrrolo[2,3-b]pyridin-3-yl)pyridin-3-yl]amino}-2-cyclopropyl-N-(2,2,2-trifluoroethyl)acetamide;
N~2~-[5-(5-chloro-1H-pyrrolo[2,3-b]pyridin-3-yl)pyridin-3-yl]-3-hydroxy-N-(2,2,2-trifluoroethyl)-D-valinamide;
3-hydroxy-N~2~-[5-(5-methoxy-1H-pyrrolo[2,3-b]pyridin-3-yl)pyridin-3-yl]-N-(2,2,2-trifluoroethyl)-D-valinamide;
N~2~-[5-(5-chloro-1H-pyrrolo[2,3-b]pyridin-3-yl)pyridin-3-yl]-N-(2,22-trifluoroethyl)-D-valinamide;
N~2~-[5-(5-chloro-1H-pyrrolo[2,3-b]pyridin-3-yl)pyridin-3-yl]-N-(2,22-trifluoroethyl)-L-valinamide;
2-{[5-(5-hydroxy-1H-pyrrolo[2,3-b]pyridin-3-yl)pyridin-3-yl]amino}-3-methyl-N-(2,2,2-trifluoroethyl)butanamide;
2-{[5-(5-hydroxy-1H-pyrrolo[2,3-b]pyridin-3-yl)pyridin-3-yl]amino}-3-methyl-N-(2,2,2-trifluoroethyl)butanamide;
N~2~-{5-[5-(1-methylethoxy)-1H-pyrrolo[2,3-b]pyridin-3-yl]pyridin-3-yl}-N-(2,2,2-trifluoroethyl)-D-valinamide;
N~2~-{5-[5-(benzyloxy)-1H-pyrrolo[2,3-b]pyridin-3-yl]pyridin-3-yl}-N-(2,2,2-trifluoroethyl)valinamide;
N~2~-5-[5-(cyclopentyloxy)-1H-pyrrolo[2,3-b]pyridine-3-yl]pyridin-3-yl)-N-(2,2,2-trifluoroethyl)valinamide;
N~2~-{5-[5-(cyclopropylmethoxy)-1H-pyrrolo[2,3-b]pyridin-3-yl]pyridin-3-yl}-N-(2,2,2-trifluoroethyl)valinamide;
N~2~-{5-[5-(2-phenylethoxy)-1H-pyrrolo[2,3-b]pyridin-3-yl]pyridin-3-yl}-N-(2,2,2-trifluoroethyl)valinamide;
N~2~-{5-[5-(2,3-dihydro-1H-inden-2-yloxy)-1H-pyrrolo[2,3-b]pyridin-3-yl]pyridin-3-yl}-N-(2,2,2-trifluoroethyl)valinamide;
N~2~-{5-[5-(tetrahydro-2H-pyran-4-yloxy)-1H-pyrrolo[2,3-b]pyridin-3-yl]pyridin-3-yl}-N-(2,2,2-trifluoroethyl)valinamide;
N~2~-(5-{5-[2-(2-oxopyrrolidin-1-yl)ethoxy]-1H-pyrrolo[2,3-b]pyridin-3-yl}pyridin-3-yl)-N-(2,2,2-trifluoroethyl)valinamide;
N~2~-{5-[5-(pyridin-3-ylmethoxy)-1H-pyrrolo[2,3-b]pyridin-3-yl]pyridin-3-yl}-N-(2,2,2-trifluoroethyl)valinamide;
N~2~-{5-[5-(2-pyridin-2-ylethoxy)-1H-pyrrolo[2,3-b]pyridin-3-yl]pyridin-3-yl}-N-(2,2,2-trifluoroethyl)valinamide;
N~2~-(5-{5-[2-(dimethylamino)ethoxy]-1H-pyrrolo[2,3-b]pyridin-3-yl}pyridin-3-yl)-N-(2,2,2-trifluoroethyl)valinamide;
N~2~-(5-{5-[3-(dimethylamino)propoxy]-1H-pyrrolo[2,3-b]pyridin-3-yl}pyridin-3-yl)-N-(2,2,2-trifluoroethyl)valinamide;

N~2~-{5-[5-(2-morpholin-4-ylethoxy)-1H-pyrrolo[2,3-b]pyridin-3-yl]pyridin-3-yl}-N-(2,2,2-trifluoroethyl)valinamide;

N~2~-(5-{5-[(1-methylpiperidin-4-yl)oxy]-1H-pyrrolo[2,3-b]pyridin-3-yl}pyridin-3-yl)-N-(2,2,2-trifluoroethyl)valinamide;

N~2~-(5-{5-[2-(4-methylpiperazin-1-yl)ethoxy]-1H-pyrrolo[2,3-b]pyridin-3-yl}pyridin-3-yl)-N-(2,2,2-trifluoroethyl)valinamide;

N~2~-(5-{5-[(1-methylpiperidin-4-yl)methoxy]-1H-pyrrolo[2,3-b]pyridin-3-yl}pyridin-3-yl)-N-(2,2,2-trifluoroethyl)valinamide;

(R)—N,N-dimethyl-3-(5-(3-methyl-1-oxo-1-(2,22-trifluoroethylamino)butan-2-ylamino)pyridin-3-yl)-1H-pyrrolo[2,3-b]pyridine-5-carboxamide;

N-(1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

N-(2-methoxy-1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

N-(2-hydroxy-1-methylethyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

3-[5-({(1R)-2-methyl-1-[(2,2,2-trifluoroethyl)carbamoyl]propyl}amino)pyridine-3-yl]-N-(tetrahydro-2H-pyran-4-yl)-1H-pyrrolo[2,3-b]pyridine-5-carboxamide;

N~2~-{5-[5-(azetidin-1-ylcarbonyl)-1H-pyrrolo[2,3-b]pyridin-3-yl]pyridin-3-yl}-N-(2,2,2-trifluoroethyl)-D-valinamide;

N-(2-methylpropyl)-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

N-methyl-3-[5-({(1R)-2-methyl-1-[(2,2,2-trifluoroethyl)carbamoyl]propyl}amino) pyridin-3-yl]-1H-pyrrolo[2,3-b]pyridine-5-carboxamide;

N-[(1,1-dioxidotetrahydrothiophen-3-yl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

3-[5-({(1R)-2-methyl-1-[(2,2,2-trifluoroethyl)carbamoyl]propyl}amino)pyridin-3-yl]N-(1H-pyrazol-5-ylmethyl)-1H-pyrrolo[2,3-b]pyridine-5-carboxamide;

N-methyl-3-[5-({(1R)-2-methyl-1-[(2,2,2-trifluoroethyl)carbamoyl]propyl}amino) pyridin-3-yl]-N-[1-(1H-pyrazol-5-yl)ethyl]-1H-pyrrolo[2,3-b]pyridine-5-carboxamide;

N-[(1-methyl-1H-pyrazol-4-yl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

N~2~-(5-{5-[(4-hydroxypiperidin-1-yl)carbonyl]-1H-pyrrolo[2,3-b]pyridin-3-yl}pyridin-3-yl)-N-(2,2,2-trifluoroethyl)-D-valinamide;

N-[(1-hydroxycyclopropyl)methyl]-3-[5-({(1R)-2-methyl-1-[(2,2,2-trifluoroethyl)carbamoyl]propyl}amino)pyridin-3-yl]-1H-pyrrolo[2,3-b]pyridine-5-carboxamide;

3-Methyl-2-(5-(5-sulfamoyl-1H-pyrrolo[2,3-b]pyridin-3-yl)pyridin-3-ylamino)-N-(2,2,2-trifluoroethyl)butanamide;

2-(5-(5-(N,N-dimethylsulfamoyl)-1H-pyrrolo[2,3-b]pyridin-3-yl)pyridin-3-ylamino)-3-methyl-N-(2,2,2-trifluoroethyl)butanamide;

N2-[5-(5-amino-1H-pyrrolo[2,3-b]pyridin-3-yl)pyridin-3-yl]-N-(2,2,2-trifluoroethyl)valinamide;

N2-{5-[5-(acetylamino)-1H-pyrrolo[2,3-b]pyridin-3-yl]pyridin-3-yl}-N-(2,2,2-trifluoroethyl)valinamide;

N2-(5-{5-[(methylsulfonyl)amino]-1H-pyrrolo[2,3-b]pyridin-3-yl}pyridin-3-yl)-N-(2,2,2-trifluoroethyl)valinamide;

N2-(5-{5-[(methylsulfonyl)amino]-1H-pyrrolo[2,3-b]pyridin-3-yl}pyridin-3-yl)-N-(2,2,2-trifluoroethyl)-L-valinamide;

N2-(5-{5-[(methylsulfonyl)amino]-1H-pyrrolo[2,3-b]pyridin-3-yl}pyridin-3-yl)-N-(2,2,2-trifluoroethyl)-D-valinamide;

N2-{5-[5-(propanoylamino)-1H-pyrrolo[2,3-b]pyridin-7-ium-3-yl]pyridin-3-yl}-N-(2,2,2-trifluoroethyl)valinamide;

N~2~-(5-{5-[(hydroxyacetyl)amino]-1H-pyrrolo[2,3-b]pyridin-3-yl}pyridin-3-yl)-N-(2,2,2-trifluoroethyl)valinamide;

N~2~-(5-{5-[(methoxyacetyl)amino]-1H-pyrrolo[2,3-b]pyridin-3-yl}pyridin-3-yl)-N-(2,2,2-trifluoroethyl)valinamide;

N2-(5-{5-[(propan-2-ylcarbamoyl)amino]-1H-pyrrolo[2,3-b]pyridin-3-yl}pyridin-3-yl)-N-(2,2,2-trifluoroethyl)valinamide;

N~2~-(5-{5-[(propylcarbamoyl)amino]-1H-pyrrolo[2,3-b]pyridin-3-yl}pyridin-3-yl)-N-(2,2,2-trifluoroethyl)valinamide;

N~2~-[5-(5-{[(2,4-difluorophenyl)carbamoyl]amino}-1H-pyrrolo[2,3-b]pyridin-3-yl)pyridin-3-yl]-N-(2,2,2-trifluoroethyl)valinamide;

N-({3-[5-({2-methyl-1-[(2,2,2-trifluoroethyl)carbamoyl]propyl}amino)pyridin-3-yl]-1H-pyrrolo[2,3-b]pyridin-5-yl}carbamoyl)alanine;

N~2~-(5-{5-[(methylcarbamoyl)amino]-1H-pyrrolo[2,3-b]pyridin-3-yl}pyridin-3-yl)-N-(2,2,2-trifluoroethyl)valinamide;

Methyl {3-[5-({3-methyl-1-oxo-1-[(2,2,2-trifluoroethyl)amino]butan-2-yl}amino)pyridin-3-yl]-1H-pyrrolo[2,3-b]pyridin-5-yl}carbamate;

ethyl {3-[5-({2-methyl-1-[(2,2,2-trifluoroethyl)carbamoyl]propyl}amino)pyridin-3yl]-1H-pyrrolo[2,3-b]pyridin-5-yl}carbamate;

1-methylethyl {3-[5-({2-methyl-1-[(2,2,2-trifluoroethyl)carbamoyl]propyl}amino)pyridin-3-yl]-1H-pyrrolo[2,3-b]pyridin-5-yl}carbamate;

N2-{5-[5-(1-methyl-1H-pyrazol-4-yl)-1H-pyrrolo[2,3-b]pyridin-3-yl]pyridin-3-yl}-N-(2,2,2-trifluoroethyl)valinamide;

N2-{5-[5-(1-methyl-1H-pyrazol-4-yl)-1H-pyrrolo[2,3-b]pyridin-3-yl]pyridin-3-yl}-N-(2,2,2-trifluoroethyl)-L-valinamide;

N2-{5-[5-(1-methyl-1H-pyrazol-4-yl)-1H-pyrrolo[2,3-b]pyridin-3-yl]pyridin-3-yl}-N-(2,2,2-trifluoroethyl)-D-valinamide;

(R)-3-methyl-2-(5-(5-((2-(pyrrolidin-1-yl)ethoxy)methyl)-1H-pyrrolo[2,3-b]pyridin-3-yl)pyridin-3-ylamino)-N-(2,2,2-trifluoroethyl)butanamide;

N~2~-{5-[5-(tert-butoxymethyl)-1H-pyrrolo[2,3-b]pyridine-3-yl]pyridin-3-yl}N-(2,2,2-trifluoroethyl)-D-valinamide;

tert-butyl 4-[2-({3-[5-({(1R)-2-methyl-1-[(2,2,2-trifluoroethyl)carbamoyl]propyl}amino)pyridin-3-yl]-1H-pyrrolo[2,3-b]pyridin-5-yl}methoxy)ethyl]piperazine-1-carboxylate;

N~2~-(5-{5-[(2-morpholin-4-ylethoxy)methyl]-1H-pyrrolo[2,3-b]pyridin-3-yl}pyridin-3-yl)-N-(2,2,2-trifluoroethyl)-D-valinamide;

N~2~-(5-{5-[(prop-2-en-1-yloxy)methyl]-1H-pyrrolo[2,3-b]pyridin-3-yl}pyridin-3-yl)-N-(2,2,2-trifluoroethyl)-D-valinamide;

tert-butyl 4-({3-[5-({(1R)-2-methyl-1-[(2,2,2-trifluoroethyl)carbamoyl]propyl}amino)pyridin-3-yl]-1H-pyrrolo[2,3-b]pyridin-5-yl}methoxy)piperidine-1-carboxylate;

N~2~-{5-[5-(pyrrolidin-1-ylmethyl)-1H-pyrrolo[2,3-b]pyridin-3-yl]pyridin-3-yl}-N-(2,2,2-trifluoroethyl)-D-valinamide;

N~2~-{3-[5-(methoxymethyl)-1H-pyrrolo[2,3-b]pyridin-3-yl]-1,2,4-triazin-5-yl}-N-(2,2,2-trifluoroethyl)-D-valinamide;

N~2~-{5-[5-(methoxymethyl)-1H-pyrrolo[2,3-b]pyridin-3-yl]pyridin-3-yl}-N-(2,2,2-trifluoroethyl)-D-valinamide;

N-((3-(5-(3-methyl-1-oxo-1-(2,2,2-trifluoroethylamino)butan-2-ylamino)pyridin-3-yl)-1H-pyrrolo[2,3-b]pyridin-5-yl)methyl)cyclopentanecarboxamide;

N~2~-(5-{5-[(propanoylamino)methyl]-1H-pyrrolo[2,3-b]pyridin-3-yl}pyridin-3-yl)-N-(2,2,2-trifluoroethyl)valinamide;

N-({3-[5-({2-methyl-1-[(2,2,2-trifluoroethyl)carbamoyl]propyl}amino)pyridin-3-yl]-1H-pyrrolo[2,3-b]pyridin-5-yl}methyl)cyclohexanecarboxamide;

N~2~-[5-(5-{[(2E)-but-2-enoylamino]methyl}-1H-pyrrolo[2,3-b]pyridin-3-yl)pyridin-3-yl]-N-(2,2,2-trifluoroethyl)valinamide;

N~2~-(5-{5-[(acetylamino)methyl]-1H-pyrrolo[2,3-b]pyridin-3-yl}pyridin-3-yl)-N-(2,2,2-trifluoroethyl)valinamide;

N~2~-[5-(5-{[(cyclopropylcarbonyl)amino]methyl}-1H-pyrrolo[2,3-b]pyridin-3-yl)pyridin-3-yl]-N-(2,2,2-trifluoroethyl)valinamide;

N~2~-{5-[5-({[(4-methyl-1,3-oxazol-5-yl)carbonyl]amino}methyl)-1H-pyrrolo[2,3-b]pyridin-3-yl]pyridin-3-yl}N-(2,2,2-trifluoroethyl)valinamide;

N~2~-[5-(5-{[(3-methylbut-2-enoyl)amino]methyl}-1H-pyrrolo[2,3-b]pyridin-3-yl)pyridin-3-yl]-N-(2,2,2-trifluoroethyl)valinamide;

N~2~-(5-{5-[(butanoylamino)methyl]-1H-pyrrolo[2,3-b]pyridin-3-yl}pyridin-3-yl)-N-(2,2,2-trifluoroethyl)valinamide;

N-(2,2,2-trifluoroethyl)-N~2~-[5-(5-{[(3,3,3-trifluoropropanoyl)amino]methyl}-1H-pyrrolo[2,3-b]pyridin-3-yl)pyridin-3-yl]valinamide; and N~2~-[5-(5-{[(pyrrolidin-1-ylcarbonyl)amino]methyl}-1H-pyrrolo[2,3-b]pyridin-3-yl)pyridin-3-yl]-N-(2,2,2-trifluoroethyl)valinamide, or a pharmaceutically acceptable salt thereof.

5. A pharmaceutical composition comprising a compound of claim 1 or a pharmaceutically acceptable salt thereof and a pharmaceutically acceptable carrier.

6. A compound according to claim 1, wherein $R^1$ is hydrogen.

\* \* \* \* \*

UNITED STATES PATENT AND TRADEMARK OFFICE
CERTIFICATE OF CORRECTION

| | | |
|---|---|---|
| PATENT NO. | : 9,096,598 B2 | Page 1 of 1 |
| APPLICATION NO. | : 14/349377 | |
| DATED | : August 4, 2015 | |
| INVENTOR(S) | : John W. Butcher et al. | |

It is certified that error appears in the above-identified patent and that said Letters Patent is hereby corrected as shown below:

On the title page of the Patent, Item (72), listing the Inventors, delete "Raksha Archarya" and insert --Raksha Acharya--.

Signed and Sealed this
Thirty-first Day of May, 2016

Michelle K. Lee
*Director of the United States Patent and Trademark Office*